US006974898B2

(12) United States Patent
Green et al.

(10) Patent No.: US 6,974,898 B2
(45) Date of Patent: Dec. 13, 2005

(54) METHOD OF MODIFYING THE CONTENT OF COTTONSEED OIL

(75) Inventors: Allan Green, Braddon (AU); Surinder Singh, Downer (AU); Qing Liu, Latham (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 275 days.

(21) Appl. No.: 09/837,751

(22) Filed: Apr. 18, 2001

(65) Prior Publication Data

US 2002/0104124 A1 Aug. 1, 2002

Related U.S. Application Data

(60) Provisional application No. 60/198,124, filed on Apr. 18, 2000.

(51) Int. Cl.$^7$ ............................. A01H 5/00; C12N 15/82
(52) U.S. Cl. ......................... 800/314; 800/281; 800/286
(58) Field of Search ................................ 800/281, 314, 800/286, 285, 287; 435/320.1, 419, 468, 427, 430; 536/23.2, 23.6, 25.1

(56) References Cited

U.S. PATENT DOCUMENTS

| 5,443,974 | A |   | 8/1995 | Hitz et al. ................ 435/172.3 |
| 5,597,718 | A |   | 1/1997 | John et al. |
| 5,760,206 | A |   | 6/1998 | Hitz et al. ................. 536/23.6 |
| 5,856,157 | A |   | 1/1999 | Craig et al. .................. 435/189 |
| 5,952,546 | A | * | 9/1999 | Bedbrook et al. .......... 800/298 |
| 6,372,965 | B1 | * | 4/2002 | Lightner et al. ............ 800/298 |

FOREIGN PATENT DOCUMENTS

| EP | 0 561 569 A2 | 3/1993 | ........... C12N/15/82 |
| EP | 0 945 514 A1 | 9/1999 | ........... C12N/15/82 |
| WO | WO 91/18985 | 12/1991 | ........... C12N/15/53 |
| WO | 9411516 | 5/1994 | |
| WO | WO 97/10328 | 3/1997 | |
| WO | WO 99/50430 | 10/1999 | ........... C12N/15/82 |
| WO | 9953050 | 10/1999 | |

OTHER PUBLICATIONS

Stam et al, The Plant Journal 21(1): 27–42, 2000.*
Budziszewski et al., "Uses of Biotechnology In Modifying Plant Lipids", Lipids, Champaign, IL, vol. 31, No. 6, pp. 557–569, (1996) (Exhibit 3).
Cartea et al., "Comparison of Sense And Antisense Methodologies For Modifying The Fatty Acid Composition of Arabidopsis Thaliana Oilseed", Plant Science, Limerick, IE, vol 136, No. 2, pp. 181–194, (1998) (Exhibit 4).
Drew et al., "RNA Hairpin Loops repress Protein Snythesis More Strongly than Hammerhead Ribozymes", European Journal of Biochemistry, vol. 226, No. 1, pp. 260–273, (Nov. 1999) (Exhibit 5).
Hisamatsu et al., "Efficiency of the Hairpin Ribozyme on the Inhibition of Gene Expression", Plant Physiology, vol. 114, No. 3 Suppl., p. 246, (1997) (Exhibit 6).

Knutzon et al., "Modification of Brassica Seed Oil by Antisense Expression of a Steraroyl–Acyl Carrier Protein Desaturase Gene", Proceedings of The National Academy of Sciences of USA, National Academy of Science, Washington, US, vol. 89, pp. 2624–2628, (Apr. 1992) (Exhibit 7).
Smith et al., "Total Silencing by Intron–Spliced Hairpin RNAs", Nature, Macmillan Journals Ltd. London, GB, vol. 407, No. 6802, pp. 319–320, (Sep. 2000) (Exhibit 8).
Toepfer et al., "Modification of Plant Lipid Synthesis", Science, American Association For the Advancement of Science, US, vol. 268, pp. 681–685, (May 5, 1995) (Exhibit 9).
Kajiwara et al. (1996) Appl Envir Microbiol 62:4309–4313 (Exhibit 9).
Kinney et al. (1996a) J. Food Lipids 3:273–292 (Exhibit 10).
Kinney (1996b) Nature Biotechnol 14:946 (Exhibit 11).
Liu et al. (1997) pp 383–385 in William JP et al (eds) Physiology, Biochemistry and Molecular Biology of Plant Lipids, Kluwer Academic Publ. (Exhibit 12).
Liu, Qing, The isolation and characterisation of fatty acid desaturase genes in cotton, a Ph.D. thesis submitted to the University of Sydney, Mar. 1998. (Exhibit 13).
Liu et al. (1999a) Plant Physiol 120:340 (Exhibit 14).
Liu et al. (1999b) Aust J. Plant Physiol 26:101–106 (Exhibit 15).
Liu et al. (2000) Biochem Soc Transact 28:927–929 (Exhibit 16).
Liu et al. (2001) Amer J Bot 88:92–102 (Exhibit 17).
Liu et al. (2002a) J Amer Coll Nutr 21:205s–211s (Exhibit 18).
Liu et al. (2002b) Abstract, 15$^{th}$ Symp Plant Lipids, May 12–17, 2002 (Exhibit 19).
Liu et al. (2002c) Plant Physiology, vol. 129, pp. 1732–1743, www.plantphysiol.org (Exhibit 20).
Okuley et al. (1994) Plant Cell 6:147–158 (Exhibit 21).
Pirtle et al. (2001) Biochim Biophys Acta 1522:122–129 (Exhibit 22).
Scheffler et al. (1997) Theor Appl Genet 94:583–591 (Exhibit 23).
Singh et al. (2000) Biochem Soc Transact 28:925–927 (Exhibit 24).
Stoutjesdijk et al. (2000) Biochem Soc Transact 28:938–940 (Exhibit 25).
Stoutjesdijk et al. (2002) Plant Physiol 129:1723–1731 (Exhibit 26).
Thelen and Ohlrogge (2002) Metab Engin 4:12–21 (Exhibit 27).
Buhr et al. (2002) Plant J 30:155–163 (Exhibit 2).

(Continued)

*Primary Examiner*—Elizabeth F. McElwain
(74) *Attorney, Agent, or Firm*—John P. White, Esq.; Cooper & Dunham LLP

(57) ABSTRACT

The present invention provides novel gene constructs and methods for the production of transgenic cotton plants that produce oils having a range of desirable attributes, including improved oil quality, and modified fatty acid composition.

30 Claims, 16 Drawing Sheets

OTHER PUBLICATIONS

Covello et al. (1996) Plant Physiol 111:223–226 (Exhibit 3).

Falcone et al. (1994) Plant Physiol 106:1453–1459 (Exhibit 4).

Green et al. (2001) American Oil Chemists Society Ann. Meeting, May 2001, Abstract (Exhibit 7).

Heppard et al. (1996) Plant Physiol 110:311–319 (Exhibit 8).

Broun, P. et al., A bifunctional oleate 12–hydroxlase: desaturase from *Lesquerella fendleri*(Jan. 1998) The Plant Journal 13(2):201–210.

Merlo, A.O. et al., "Ribozymes Targeted to Stearoyl–ACP Δ9 Desaturase mRNA Produce Heritable Increases of Stearic Acid in Transgenic Maise Leaves" (Oct. 1998) The Plant Cell 10(10):1603–1621.

Napier, J.A. et al., "Plant desaturases: harvesting the fat of the land" (Apr. 1999) Current Opinion in Plant Biology 2(2):123–127.

Liu, et al., GenBank abstract accession No. AJ132636, Feb. 15, 2000.

Brubaker et al., GenBank abstract accession No. AJ244923, May 26, 1999.

Liu et al., GenBank abstract accession No. X97016, Oct. 29, 1997.

Liu et al., GenBank abstract accession No. X95988, Mar. 6, 1996.

* cited by examiner

```
CGAAAAGAAAAAATGGCTTTGAATTTTAATGCCATCGCCTCGAAATCTCAGAAGCTCCCT  60
              M  A  L  N  F  N  A  I  A  S  K  S  Q  K  L  P
TGCTTTGCTCTTCCACCAAAGGCCACCCTTAGATCTCCCAAGTTTTCCATGATCTCCACC 120
 C  F  A  L  P  P  K  A  T  L  R  S  P  K  F  S  M  I  S  T
ATTCCTTCTGGCTCCAAAGAGGTTGGGAATCTGAAAAAGCCTTTCACGCCTCCAAAGGAG 180
 I  P  S  G  S  K  E  V  G  N  L  K  K  P  F  T  P  P  K  E
GTGCCTGTTCAGATCACCCACTCCATGCCGCCTCACAAGATTGAGATCTTTAAATCTTTG 240
 V  P  V  Q  I  T  H  S  M  P  P  H  K  I  E  I  F  K  S  L
GAGGGCTGGCTGAGAACAACATTCTGACTCACCTCAAACCAGTTGAGAAATGTTGGCAA  300
 E  G  W  A  E  N  N  I  L  T  H  L  K  P  V  E  K  C  W  Q
CCCGCCGACTTTCTTCCAGATCCTAATTCTGATGGATTTCATGAGCAAGTCAAAGAGCTT 360
 P  A  D  F  L  P  D  P  N  S  D  G  F  H  E  Q  V  K  E  L
AGGGAAAGGGCAAAGGAGATCCCAGATGATTACTTTGTAGTTTTGGTTGGTGATATGATC 420
 R  E  R  A  K  E  I  P  D  D  Y  F  V  V  L  V  G  D  M  I
ACCGAGGAAGCCCTTTCAACTTATCAAACAATGCTTAATACCTTGGATGGAACTCGTGAT 480
 T  E  E  A  L  S  T  Y  Q  T  M  L  N  T  L  D  G  T  R  D
GAGACAGGTGCTAGCCTTACCCCTTGGGCCATTTGGACCAGGGCTTGGACTGCTGAAGAA 540
 E  T  G  A  S  L  T  P  W  A  I  W  T  R  A  W  T  A  E  E
AACAGGCATGGTGATCTGCTTAATAAGTATCTCTACTTGTCTGGGAGAGTGGACATGAGG 600
 N  R  H  G  D  L  L  N  K  Y  L  Y  L  S  G  R  V  D  M  R
CAAATTGAGAGGACAATCCAGTACTTGATTGGATCGGGAATGGATCCTCATACAGAGAAT 660
 Q  I  E  R  T  I  Q  Y  L  I  G  S  G  M  D  P  H  T  E  N
AGTCCTTACCGAGGATTCATATATACTTCGTTCCAAGAAAGGGCAACTTTTATTTCCCAT 720
 S  P  Y  R  G  F  I  Y  T  S  F  Q  E  R  A  T  F  I  S  H
GGGAATACAGGCAGGCTGGCTAAGGAGTATGGGGATATTAACTTGGCTCAAATTTGTGGT 780
 G  N  T  G  R  L  A  K  E  Y  G  D  I  N  L  A  Q  I  C  G
AGCATTGCCTCAGATGAGAAGCGCCACGAGACAGCCTATACCAAAATCGTTGAAAAGCTG 840
 S  I  A  S  D  E  K  R  H  E  T  A  Y  T  K  I  V  E  K  L
TTTGAGATTGATCCTGATGAAACAGTCCTGGCATTTGCTGACATGATGAAGAAGAAAATC 900
 F  E  I  D  P  D  E  T  V  L  A  F  A  D  M  M  K  K  K  I
GCCATGCCGGCTGAGTTCATCTATGATGGCAGAGATTATAACTTATTTGACCACTACTCA 960
 A  M  P  A  E  F  I  Y  D  G  R  D  Y  N  L  F  D  H  Y  S
GCTGTTGCCCAAAGAATCGGGGTTTACACTGCTAAGGACTATGTTGATATAGTAGAGCAC 1020
 A  V  A  Q  R  I  G  V  Y  T  A  K  D  Y  V  D  I  V  E  H
CTGGTGGATCGATGGAAGGTGAAGGAGCTAGCTGGGCTTTCAGCCGAGGGGCGTAAAGCT 1080
 L  V  D  R  W  K  V  K  E  L  A  G  L  S  A  E  G  R  K  A
CAGGACTACTTGTGTTCACTTCCTTCGAGAATTAGAAGGTTAGAGGAGAGAGCGCAAGAA 1140
 Q  D  Y  L  C  S  L  P  S  R  I  R  R  L  E  E  R  A  Q  E
AAGGCCAAGGAAGCACCCAGTGTCCCATTCAGTTGGATATTTGATAGAGAAGTGAAACTT 1200
 K  A  K  E  A  P  S  V  P  F  S  W  I  F  D  R  E  V  K  L
TAGGTCATGAAATACAGTTAAGACTCCTGCAATGCATTTGAGGAAACAAACACGAAGAAG 1260
 *
CTGAATGCCAACTTCTCTTTATATATCCGATGTAATAGAGGTTGTATATGTAACAGGAGG 1320
AATTGCGTGGCTTTGGTTAGGGTAGCACATGTTTTCTGGATGTGTTGTGTCCTTAAAAAA 1380
TAATGCCGATAGCGGCAGCTGTGATAGTTTAGATGTTTGTTTTCATAATGTCTGTTATA  1440
TCGTTGTACGAGTAGTATGTGTTGTTTTTGTTGAAACAATCTTCATATCTTAGTGATAAA 1500
TGATAATGCTGTGTAGTCATAGTTTTTAGTTTGCAATAAAAAAAAAAAAAAA         1553
```

FIGURE 2

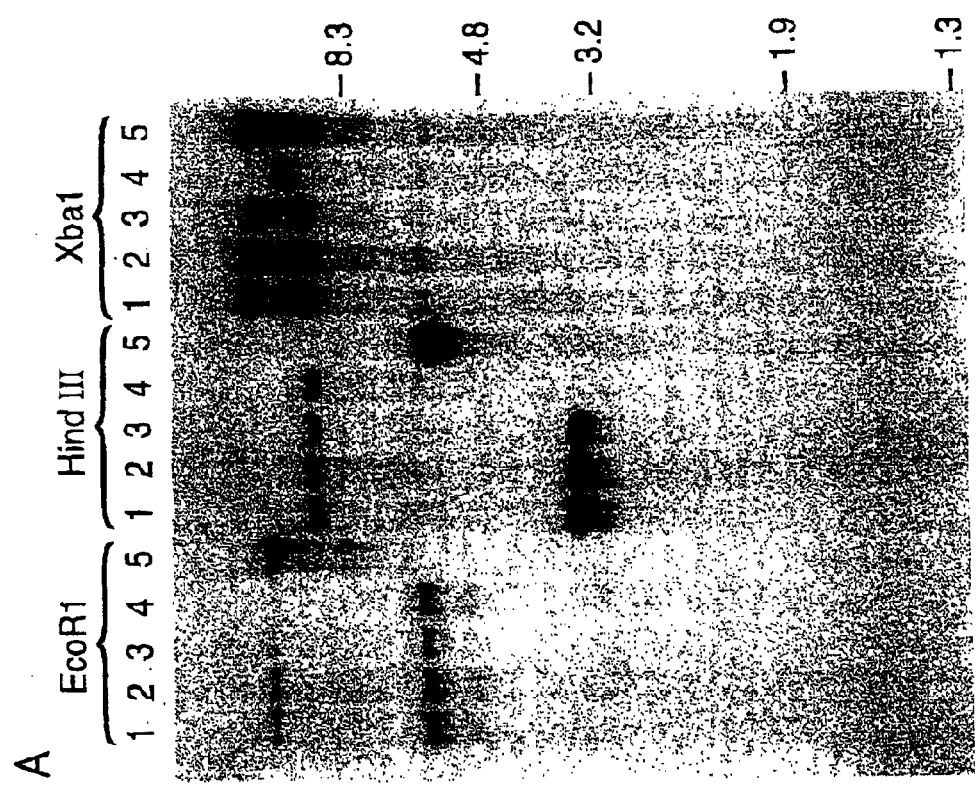

```
CTCGCCCAAAACCAACACGCCTTCTTTGCCTCGTGTTTCATCACCTGGCGTTAAACTGCT      60
TTCTTTAAAGCCAGCAAAATGGGTGCCGGTGGTAGGATGCCAATTGACGGTATAAAGGAG     120
                 M  G  A  G  G  R  M  P  I  D  G  I  K  E
GAAAATCGAGGCTCGGTCAATCGAGTTCCGATCGAGAAGCCTCCGTTTACGCTCGGTCAG     180
 E  N  R  G  S  V  N  R  V  P  I  E  K  P  P  F  T  L  G  Q
ATCAAGCAAGCCATTCCGCCCCACTGTTTTCGCCGCTCCCTCCTTCGATCCTTCTCCTAC     240
 I  K  Q  A  I  P  P  H  C  F  R  R  S  L  L  R  S  F  S  Y
GTGGTCCATGACCTATGCTTAGCCTCTTTCTTTTACTACATTGCAACATCATATTTTCAC     300
         d12A4 primer
 V  V  H  D  L  C  L  A  S  F  F  Y  Y  I  A  T  S  Y  F  H
TTTCTCCCACAACCCTTTTCCTACATTGCTTGGCCTGTCTATTGGGTTCTCCAAGGTTGC     360
 F  L  P  Q  P  F  S  Y  I  A  W  P  V  Y  W  V  L  Q  G  C
ATCCTCACCGGTGTTTGGGTCATCGCACACGAGTGGGGTCACCACGCTTTCAGAGACTAC    420
 I  L  T  G  V  W  V  I  A  H  E  W  G  H  H  A  F  R  D  Y
CAATGGGTTGACGACACCGTCGGGTTGATCCTTCATTCCGCCCTTTTAGTCCCGTACTTC    480
 Q  W  V  D  D  T  V  G  L  I  L  H  S  A  L  L  V  P  Y  F
TCGTGGAAAATCAGTCACCGCCGTCACCACTCGAACACCGGTTCCATGGAGCGTGACGAA    540
 S  W  K  I  S  H  R  R  H  H  S  N  T  G  S  M  E  R  D  E
GTATTCGTGCCCAAACCCAAGTCTAAATTATCATGCTTTGCGAAATACTTAAACAATCCA    600
 V  F  V  P  K  P  K  S  K  L  S  C  F  A  K  Y  L  N  N  P
CCCGGTCGAGTTCTATCTCTTGTAGTCACATTGACTCTTGGTTGGCCTATGTACTTAGCC    660
 P  G  R  V  L  S  L  V  V  T  L  T  L  G  W  P  M  Y  L  A
TTCAACGTTTCGGGTCGATACTATGATCGATTAGCTTCCCACTATAACCCTTATGGCCCC    720
 F  N  V  S  G  R  Y  Y  D  R  L  A  S  H  Y  N  P  Y  G  P
ATTTACTCCGATCGCGAGAGGCTACAAGTTTACATCTCCGATACTGGTATATTTGCGGTA    780
 I  Y  S  D  R  E  R  L  Q  V  Y  I  S  D  T  G  I  F  A  V
ATTTATGTACTTTATAAGATTGCTGCAACAAAAGGGCTGGCTTGGCTTTTATGCACTTAT    840
 I  Y  V  L  Y  K  I  A  A  T  K  G  L  A  W  L  L  C  T  Y
GGGGTGCCTCTACTTATTGTGAATGCCTTCCTTGTGTTGATCACCTACTTGCAACATACT    900
 G  V  P  L  L  I  V  N  A  F  L  V  L  I  T  Y  L  Q  H  T
CACTCGGCATTGCCGCATTATGACTCGTCCGAATGGGATTGGTTGCGAGGAGCATTGTCG    960
 H  S  A  L  P  H  Y  D  S  S  E  W  D  W  L  R  G  A  L  S
ACGATGGATCGAGATTTCGGGGTGTTGAACAAAGTGTTCCATAACATCACCGATACGCAT   1020
 T  M  D  R  D  F  G  V  L  N  K  V  F  H  N  I  T  D  T  H
GTTGCTCATCACCTCTTCTCAACGATGCCACATTATCATGCAATGGAGGCCACTAAAGCA   1080
 V  A  H  H  L  F  S  T  M  P  H  Y  H  A  M  E  A  T  K  A
ATCAAACCAATACTCGGCAAGTATTATCCTTTCGACGGGACACCGATTTACAAGGCAATG   1140
 I  K  P  I  L  G  K  Y  Y  P  F  D  G  T  P  I  Y  K  A  M
TGGAGGGAGGCAAAAGAGTGCCTTTACGTTGAGCCTGACGTTGGTGGTGGTGGTGGTGGT   1200
 W  R  E  A  K  E  C  L  Y  V  E  P  D  V  G  G  G  G  G  G
AGCAAAGGTGTTTTTTGGTATCGTAACAAGTTCTAAAGACCGACCAACTGCCTGATAGCT   1260
 S  K  G  V  F  W  Y  R  N  K  F  *
GGCCGGCGAAATCAACCTAAAACGTACTTATTAGACTAGTGTTAACTAGGGAAGTTAATA   1320
ATTAATGGTAGGAAAATGTGGAATAGTTGCCTAGTAGTTTTATGTATTAAGTGTTGTATT   1380
AATAAACTATATGGTAGAAAAAAAAAAAAAA                                1411
```

FIGURE 5

```
taaaaaaaaaaggcatttctttcatcttaaagagacagcgaggaagccacgaagataata
gagtgattttcaatctccattttaagggtgtggaacaatgggtgctggaggcagaatgtc
                                   M  G  A  G  G  R  M  S
ggttccaacgagtccaaaaaaacccgaattcaactcactgaagcgagttccatactcaaa
 V  P  T  S  P  K  K  P  E  F  N  S  L  K  R  V  P  Y  S  K
gccacccttcactctgagtgaaatcaagaaagccatcccaccacactgtttccagcgctc
 P  P  F  T  L  S  E  I  K  K  A  I  P  P  H  C  F  Q  R  S
cgttttacgctcattctcatatctcctttacgactttatattggcctctcttttttacca
 V  L  R  S  F  S  Y  L  L  Y  D  F  I  L  A  S  L  F  Y  H
tgtggccaccaattacttccctaaccttcctcaggctctctccaacgtggcttggcctct
 V  A  T  N  Y  F  P  N  L  P  Q  A  L  S  N  V  A  W  P  L
ttattgggccatgcaaggttgcattttgaccggcgtttgggtcatagcccatgaatgtgg
 Y  W  A  M  Q  G  C  I  L  T  G  V  W  V  I  A  H  E  C  G
ccaccatgctttcagtgattatcaatggcttgacgacaccgtgggccttatcctccactc
 H  H  A  F  S  D  Y  Q  W  L  D  D  T  V  G  L  I  L  H  S
ttctctcttagttccatatttctcttggaaatatagccaccggcgtcaccattctaacac
 S  L  L  V  P  Y  F  S  W  K  Y  S  H  R  R  H  H  S  N  T
cggttccctcgaaagggatgaagtgttcgttcccaagaaaaaatctggtttaagatggtg
 G  S  L  E  R  D  E  V  F  V  P  K  K  K  S  G  L  R  W  W
ggccaaacacttcaacaatccaccgggtcggtttctgtcaatcaccattcaacttaccct
 A  K  H  F  N  N  P  P  G  R  F  L  S  I  T  I  Q  L  T  L
tggttggccgctttacttagctttcaacgttgccggccggccttacgacaggttcgcttg
 G  W  P  L  Y  L  A  F  N  V  A  G  R  P  Y  D  R  F  A  C
ccactatgaccettacggccccatattttccgaccgggaacgactccaaatctatatctc
 H  Y  D  P  Y  G  P  I  F  S  D  R  E  R  L  Q  I  Y  I  S
tgacgccggcgtcctcgctgtcgcctatgcgctctaccgtctcgtgttggccaaaggggt
 D  A  G  V  L  A  V  A  Y  A  L  Y  R  L  V  L  A  K  G  V
aggttggggttattagcgtttatggggtgccattattggtggttaacgccttcttagtaat
 G  W  V  I  S  V  Y  G  V  P  L  L  V  V  N  A  F  L  V  M
gatcacgtatttgcaacacactcacccatctttgccgcactatgattcctcggagtggga
 I  T  Y  L  Q  H  T  H  P  S  L  P  H  Y  D  S  S  E  W  D
ctggatgagaggagctttatcaactgtggacagagattatgggatttttaaacaaggtttt
 W  M  R  G  A  L  S  T  V  D  R  D  Y  G  I  L  N  K  V  F
ccataacataaccgacactcatgtggctcatcatttgttttcgacaatgcctcactatca
 H  N  I  T  D  T  H  V  A  H  H  L  F  S  T  M  P  H  Y  H
tgccatggtggccaccaaggcgataaagcccatattgggggaatactatcagttcgatgg
 A  M  V  A  T  K  A  I  K  P  I  L  G  E  Y  Y  Q  F  D  G
gatgcctgtctataaggcgatatggagggaggcgaaggagtgtctctacgttgaaccaga
 M  P  V  Y  K  A  I  W  R  E  A  K  E  C  L  Y  V  E  P  D
tgagggcgacaaggataaaggtgtgttttggtttagaaacaagctttaaatatttgcatt
 E  G  D  K  D  K  G  V  F  W  F  R  N  K  L  *
ttaccttaggcatgttctagtcgttgatgttttaaggatatttagccgacatacttggt
tttccttttgggacttttagctttgtatttgcagacaataatcttgttcactattaaa
taatggtagaaataaatacacagcatggattggcaataaaaa
```

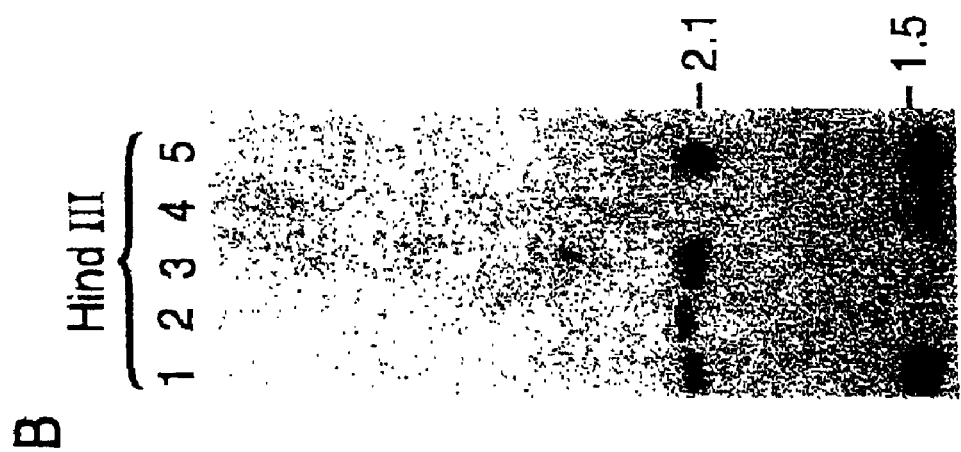

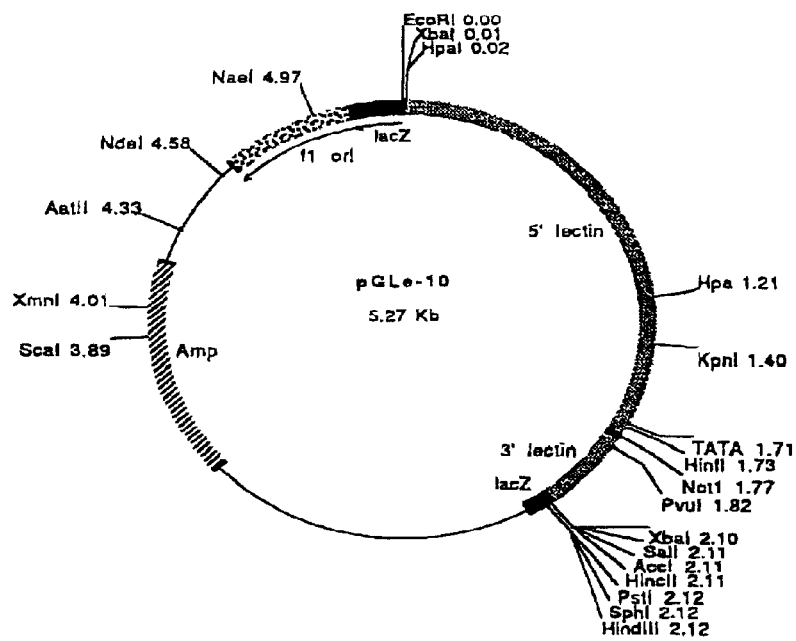
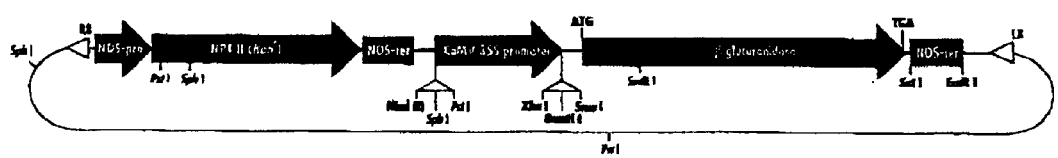
FIGURE 10

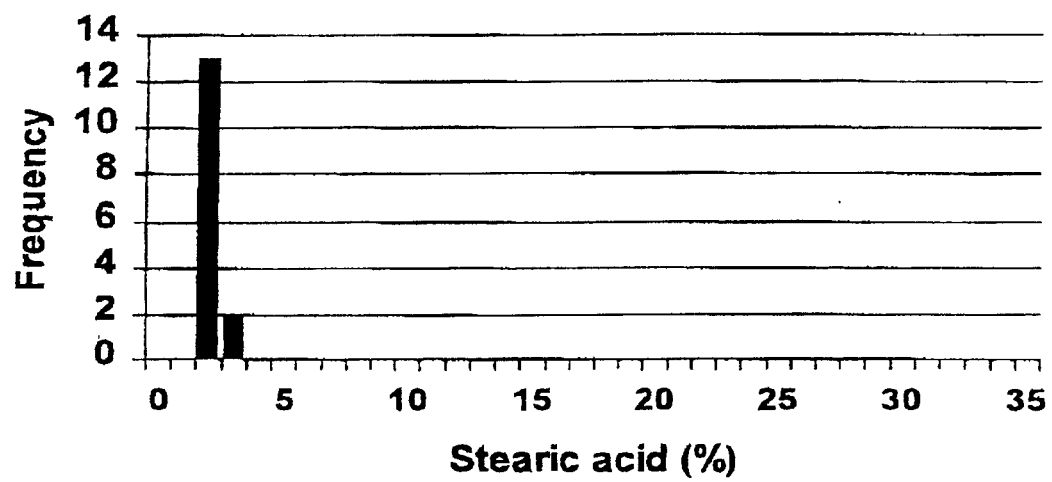
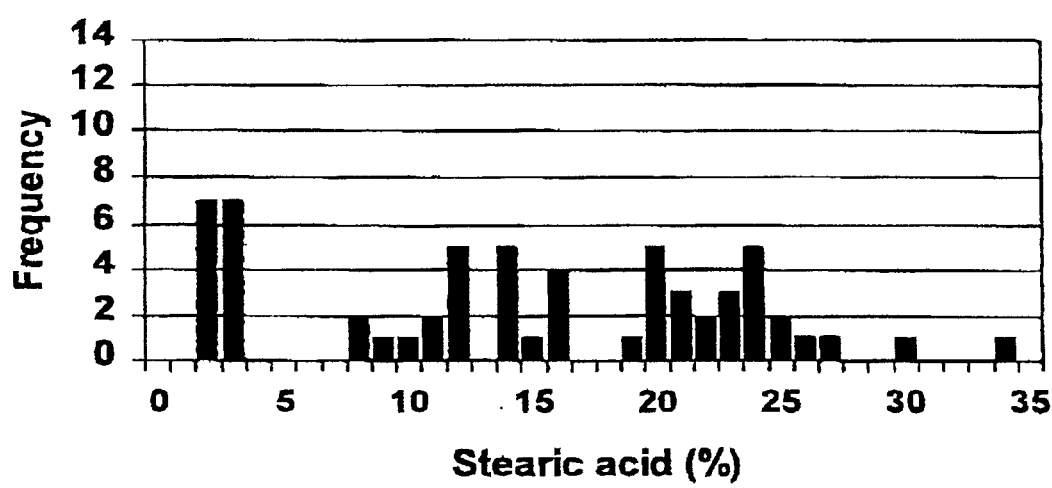
FIGURE 11

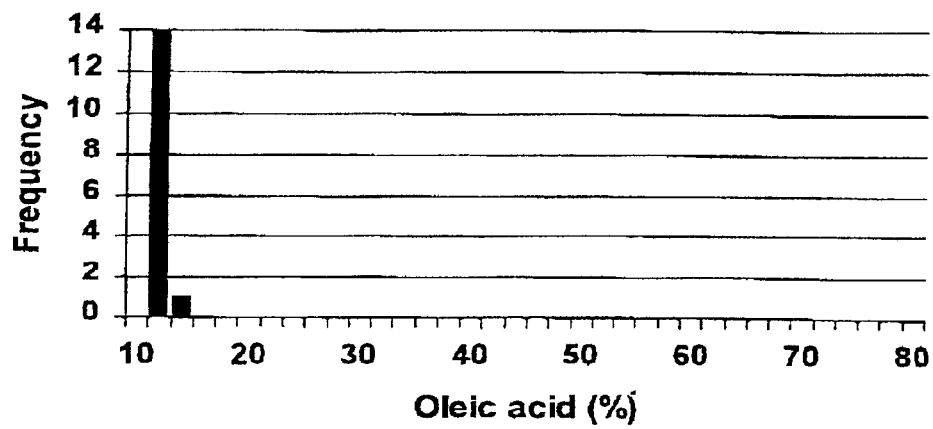
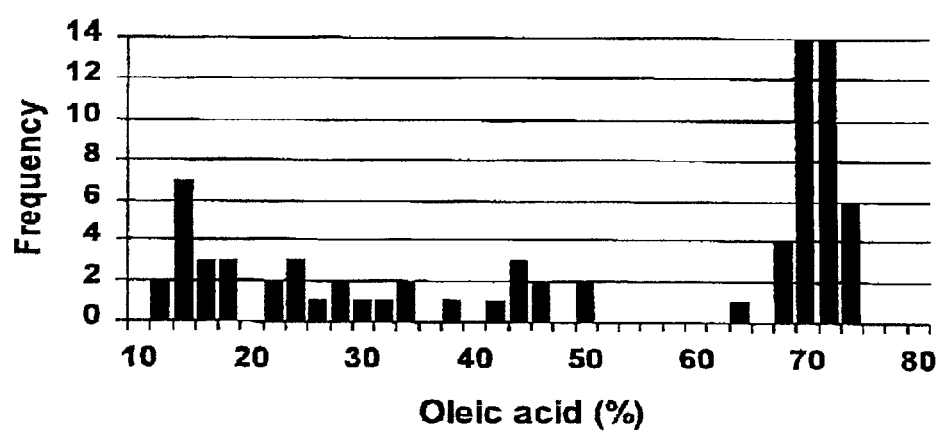
FIGURE 12

SEQUENCE LISTING

```
<160> NUMBER OF SEQ ID NOS: 35

<210> SEQ ID NO 1
<211> LENGTH: 1493
<212> TYPE: DNA
<213> ORGANISM: Gossypium sp.
<220> FEATURE:
<221> NAME/KEY: CDS
<222> LOCATION: (13)..(1200)

<400> SEQUENCE: 1
cgaaaagaaa aa atg gct ttg aat ttt aat gcc atc gcc tcg aaa tct cag      51
              Met Ala Leu Asn Phe Asn Ala Ile Ala Ser Lys Ser Gln
               1               5                  10 aag ctc cct tgc ttt gct ctt cca cca aag gcc acc ctt aga tct ccc        99
```

```
                Lys Leu Pro Cys Phe Ala Leu Pro Pro Lys Ala Thr Leu Arg Ser Pro
                    15                  20                  25 aag ttt tcc atg atc tcc acc att cct tct ggc tcc aaa gag gtt ggg         147
Lys Phe Ser Met Ile Ser Thr Ile Pro Ser Gly Ser Lys Glu Val Gly
                30                  35                  40                  45 aat ctg aaa aag cct ttc acg cct cca aag gag gtg cct gtt cag atc         195
Asn Leu Lys Lys Pro Phe Thr Pro Pro Lys Glu Val Pro Val Gln Ile
                    50                  55                  60 acc cac tcc atg ccg cct cac aag att gag atc ttt aaa tct ttg gag         243
Thr His Ser Met Pro Pro His Lys Ile Glu Ile Phe Lys Ser Leu Glu
                65                  70                  75 ggc tgg gct gag aac aac att ctg act cac ctc aaa cca gtt gag aaa         291
Gly Trp Ala Glu Asn Asn Ile Leu Thr His Leu Lys Pro Val Glu Lys
            80                  85                  90 tgt tgg caa ccc gcc gac ttt ctt cca gat cct aat tct gat gga ttt         339
Cys Trp Gln Pro Ala Asp Phe Leu Pro Asp Pro Asn Ser Asp Gly Phe
            95                  100                 105 cat gag caa gtc aaa gag ctt agg gaa agg gca aag gag atc cca gat         387
His Glu Gln Val Lys Glu Leu Arg Glu Arg Ala Lys Glu Ile Pro Asp
110                 115                 120                 125 gat tac ttt gta gtt ttg gtt ggt gat atg atc acc gag gaa gcc ctt         435
Asp Tyr Phe Val Val Leu Val Gly Asp Met Ile Thr Glu Glu Ala Leu
                130                 135                 140 tca act tat caa aca atg ctt aat acc ttg gat gga act cgt gat gag         483
Ser Thr Tyr Gln Thr Met Leu Asn Thr Leu Asp Gly Thr Arg Asp Glu
                    145                 150                 155 aca ggt gct agc ctt acc cct tgg gcc att tgg acc agg gct tgg act         531
Thr Gly Ala Ser Leu Thr Pro Trp Ala Ile Trp Thr Arg Ala Trp Thr
                160                 165                 170 gct gaa gaa aac agg cat ggt gat ctg ctt aat aag tat ctc tac ttg         579
Ala Glu Glu Asn Arg His Gly Asp Leu Leu Asn Lys Tyr Leu Tyr Leu
            175                 180                 185 tct ggg aga gtg gac atg agg caa att gag agg aca atc cag tac ttg         627
Ser Gly Arg Val Asp Met Arg Gln Ile Glu Arg Thr Ile Gln Tyr Leu
190                 195                 200                 205 att gga tcg gga atg gat cct cat aca gag aat agt cct tac cga gga         675
Ile Gly Ser Gly Met Asp Pro His Thr Glu Asn Ser Pro Tyr Arg Gly
                210                 215                 220 ttc ata tat act tcg ttc caa gaa agg gca act ttt att tcc cat ggg         723
Phe Ile Tyr Thr Ser Phe Gln Glu Arg Ala Thr Phe Ile Ser His Gly
                    225                 230                 235 aat aca ggc agg ctg gct aag gag tat ggg gat att aac ttg gct caa         771
Asn Thr Gly Arg Leu Ala Lys Glu Tyr Gly Asp Ile Asn Leu Ala Gln
                240                 245                 250 att tgt ggt agc att gcc tca gat gag aag cgc cac gag aca gcc tat         819
Ile Cys Gly Ser Ile Ala Ser Asp Glu Lys Arg His Glu Thr Ala Tyr
            255                 260                 265 acc aaa atc gtt gaa aag ctg ttt gag att gat cct gat gaa aca gtc         867
Thr Lys Ile Val Glu Lys Leu Phe Glu Ile Asp Pro Asp Glu Thr Val
270                 275                 280                 285 ctg gca ttt gct gac atg atg aag aag aaa atc gcc atg ccg gct gag         915
Leu Ala Phe Ala Asp Met Met Lys Lys Lys Ile Ala Met Pro Ala Glu
                290                 295                 300 ttc atc tat gat ggc aga gat tat aac tta ttt gac cac tac tca gct         963
Phe Ile Tyr Asp Gly Arg Asp Tyr Asn Leu Phe Asp His Tyr Ser Ala
                    305                 310                 315 gtt gcc caa aga atc ggg gtt tac act gct aag gac tat gtt gat ata         1011
Val Ala Gln Arg Ile Gly Val Tyr Thr Ala Lys Asp Tyr Val Asp Ile
            320                 325                 330
```

-continued

```
gta gag cac ctg gtg gat cga tgg aag gtg aag gag cta gct ggg ctt    1059
Val Glu His Leu Val Asp Arg Trp Lys Val Lys Glu Leu Ala Gly Leu
        335                 340                 345 tca gcc gag ggg cgt aaa gct cag gac tac ttg tgt tca ctt cct tcg    1107
Ser Ala Glu Gly Arg Lys Ala Gln Asp Tyr Leu Cys Ser Leu Pro Ser
350                 355                 360                 365 aga att aga agg tta gag gag aga gcg caa gaa aag gcc aag gaa gca    1155
Arg Ile Arg Arg Leu Glu Glu Arg Ala Gln Glu Lys Ala Lys Glu Ala
                370                 375                 380 ccc agt gtc cca ttc agt tgg ata ttt gat aga gaa gtg aaa ctt        1200
Pro Ser Val Pro Phe Ser Trp Ile Phe Asp Arg Glu Val Lys Leu
            385                 390                 395 taggtcatga aatacagtta agactcctgc aatgcatttg aggaaacaaa cacgaagaag   1260
aattgcgtgg ctttggttag ggtagcacat gttttctgga tgtgttgtgt ccttaaaaaa   1320
taatgccgat agcggcagct gtgatagttt tagatgtttg ttttcataat gtctgttata   1380
tcgttgtacg agtagtatgt gttgttttg ttgaaacaat cttcatatct tagtgataaa   1440
tgataatgct gtgtagtcat agtttttagt ttgcaataaa aaaaaaaaaa aaa          1493
```

```
<210> SEQ ID NO 2
<211> LENGTH: 396
<212> TYPE: PRT
<213> ORGANISM: Gossypium sp.

<400> SEQUENCE: 2

Met Ala Leu Asn Phe Asn Ala Ile Ala Ser Lys Ser Gln Lys Leu Pro
1               5                   10                  15

Cys Phe Ala Leu Pro Pro Lys Ala Thr Leu Arg Ser Pro Lys Phe Ser
            20                  25                  30

Met Ile Ser Thr Ile Pro Ser Gly Ser Lys Glu Val Gly Asn Leu Lys
        35                  40                  45

Lys Pro Phe Thr Pro Pro Lys Glu Val Pro Val Gln Ile Thr His Ser
    50                  55                  60

Met Pro Pro His Lys Ile Glu Ile Phe Lys Ser Leu Glu Gly Trp Ala
65                  70                  75                  80

Glu Asn Asn Ile Leu Thr His Leu Lys Pro Val Glu Lys Cys Trp Gln
                85                  90                  95

Pro Ala Asp Phe Leu Pro Asp Pro Asn Ser Asp Gly Phe His Glu Gln
            100                 105                 110

Val Lys Glu Leu Arg Glu Arg Ala Lys Glu Ile Pro Asp Asp Tyr Phe
        115                 120                 125

Val Val Leu Val Gly Asp Met Ile Thr Glu Glu Ala Leu Ser Thr Tyr
    130                 135                 140

Gln Thr Met Leu Asn Thr Leu Asp Gly Thr Arg Asp Glu Thr Gly Ala
145                 150                 155                 160

Ser Leu Thr Pro Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Arg Thr Ile Gln Tyr Leu Ile Gly Ser
        195                 200                 205

Gly Met Asp Pro His Thr Glu Asn Ser Pro Tyr Arg Gly Phe Ile Tyr
    210                 215                 220

Thr Ser Phe Gln Glu Arg Ala Thr Phe Ile Ser His Gly Asn Thr Gly
225                 230                 235                 240
```

```
Arg Leu Ala Lys Glu Tyr Gly Asp Ile Asn Leu Ala Gln Ile Cys Gly
                245                 250                 255

Ser Ile Ala Ser Asp Glu Lys Arg His Glu Thr Ala Tyr Thr Lys Ile
            260                 265                 270

Val Glu Lys Leu Phe Glu Ile Asp Pro Asp Glu Thr Val Leu Ala Phe
        275                 280                 285

Ala Asp Met Met Lys Lys Lys Ile Ala Met Pro Ala Glu Phe Ile Tyr
290                 295                 300

Asp Gly Arg Asp Tyr Asn Leu Phe Asp His Tyr Ser Ala Val Ala Gln
305                 310                 315                 320

Arg Ile Gly Val Tyr Thr Ala Lys Asp Tyr Val Asp Ile Val Glu His
                325                 330                 335

Leu Val Asp Arg Trp Lys Val Lys Glu Leu Ala Gly Leu Ser Ala Glu
            340                 345                 350

Gly Arg Lys Ala Gln Asp Tyr Leu Cys Ser Leu Pro Ser Arg Ile Arg
        355                 360                 365

Arg Leu Glu Glu Arg Ala Gln Glu Lys Ala Lys Glu Ala Pro Ser Val
370                 375                 380

Pro Phe Ser Trp Ile Phe Asp Arg Glu Val Lys Leu
385                 390                 395

<210> SEQ ID NO 3
<211> LENGTH: 1411
<212> TYPE: DNA
<213> ORGANISM: Gossypium sp.
<220> FEATURE:
<221> NAME/KEY: CDS
<222> LOCATION: (79)..(1233)

<400> SEQUENCE: 3
ctcgcccaaa accaacacgc cttctttgcc tcgtgtttca tcacctggcg ttaaactgct      60
ttctttaaag ccagcaaa atg ggt gcc ggt ggt agg atg cca att gac ggt      111
                    Met Gly Ala Gly Gly Arg Met Pro Ile Asp Gly
                     1               5                      10 ata aag gag gaa aat cga ggc tcg gtc aat cga gtt ccg atc gag aag      159
Ile Lys Glu Glu Asn Arg Gly Ser Val Asn Arg Val Pro Ile Glu Lys
            15                  20                  25 cct ccg ttt acg ctc ggt cag atc aag caa gcc att ccg ccc cac tgt      207
Pro Pro Phe Thr Leu Gly Gln Ile Lys Gln Ala Ile Pro Pro His Cys
        30                  35                  40 ttt cgc cgc tcc ctc ctt cga tcc ttc tcc tac gtg gtc cat gac cta      255
Phe Arg Arg Ser Leu Leu Arg Ser Phe Ser Tyr Val Val His Asp Leu
    45                  50                  55 tgc tta gcc tct ttc ttt tac tac att gca aca tca tat ttt cac ttt      303
Cys Leu Ala Ser Phe Phe Tyr Tyr Ile Ala Thr Ser Tyr Phe His Phe
60                  65                  70                  75 ctc cca caa ccc ttt tcc tac att gct tgg cct gtc tat tgg gtt ctc      351
Leu Pro Gln Pro Phe Ser Tyr Ile Ala Trp Pro Val Tyr Trp Val Leu
                80                  85                  90 caa ggt tgc atc ctc acc ggt gtt tgg gtc atc gca cac gag tgg ggt      399
Gln Gly Cys Ile Leu Thr Gly Val Trp Val Ile Ala His Glu Trp Gly
            95                  100                 105 cac cac gct ttc aga gac tac caa tgg gtt gac gac acc gtc ggg ttg      447
His His Ala Phe Arg Asp Tyr Gln Trp Val Asp Asp Thr Val Gly Leu
        110                 115                 120 atc ctt cat tcc gcc ctt tta gtc ccg tac ttc tcg tgg aaa atc agt      495
Ile Leu His Ser Ala Leu Leu Val Pro Tyr Phe Ser Trp Lys Ile Ser
    125                 130                 135
```

```
cac cgc cgt cac cac tcg aac acc ggt tcc atg gag cgt gac gaa gta    543
His Arg Arg His His Ser Asn Thr Gly Ser Met Glu Arg Asp Glu Val
140             145                 150                 155 ttc gtg ccc aaa ccc aag tct aaa tta tca tgc ttt gcg aaa tac tta    591
Phe Val Pro Lys Pro Lys Ser Lys Leu Ser Cys Phe Ala Lys Tyr Leu
            160                 165                 170 aac aat cca ccc ggt cga gtt cta tct ctt gta gtc aca ttg act ctt    639
Asn Asn Pro Pro Gly Arg Val Leu Ser Leu Val Val Thr Leu Thr Leu
        175                 180                 185 ggt tgg cct atg tac tta gcc ttc aac gtt tcg ggt cga tac tat gat    687
Gly Trp Pro Met Tyr Leu Ala Phe Asn Val Ser Gly Arg Tyr Tyr Asp
    190                 195                 200 cga tta gct tcc cac tat aac cct tat ggc ccc att tac tcc gat cgc    735
Arg Leu Ala Ser His Tyr Asn Pro Tyr Gly Pro Ile Tyr Ser Asp Arg
205                 210                 215 gag agg cta caa gtt tac atc tcc gat act ggt ata ttt gcg gta att    783
Glu Arg Leu Gln Val Tyr Ile Ser Asp Thr Gly Ile Phe Ala Val Ile
220                 225                 230                 235 tat gta ctt tat aag att gct gca aca aaa ggg ctg gct tgg ctt tta    831
Tyr Val Leu Tyr Lys Ile Ala Ala Thr Lys Gly Leu Ala Trp Leu Leu
                240                 245                 250 tgc act tat ggg gtg cct cta ctt att gtg aat gcc ttc ctt gtg ttg    879
Cys Thr Tyr Gly Val Pro Leu Leu Ile Val Asn Ala Phe Leu Val Leu
            255                 260                 265 atc acc tac ttg caa cat act cac tcg gca ttg ccg cat tat gac tcg    927
Ile Thr Tyr Leu Gln His Thr His Ser Ala Leu Pro His Tyr Asp Ser
        270                 275                 280 tcc gaa tgg gat tgg ttg cga gga gca ttg tcg acg atg gat cga gat    975
Ser Glu Trp Asp Trp Leu Arg Gly Ala Leu Ser Thr Met Asp Arg Asp
    285                 290                 295 ttc ggg gtg ttg aac aaa gtg ttc cat aac atc acc gat acg cat gtt    1023
Phe Gly Val Leu Asn Lys Val Phe His Asn Ile Thr Asp Thr His Val
300                 305                 310                 315 gct cat cac ctc ttc tca acg atg cca cat tat cat gca atg gag gcc    1071
Ala His His Leu Phe Ser Thr Met Pro His Tyr His Ala Met Glu Ala
                320                 325                 330 act aaa gca atc aaa cca ata ctc ggc aag tat tat cct ttc gac ggg    1119
Thr Lys Ala Ile Lys Pro Ile Leu Gly Lys Tyr Tyr Pro Phe Asp Gly
            335                 340                 345 aca ccg att tac aag gca atg tgg agg gag gca aaa gag tgc ctt tac    1167
Thr Pro Ile Tyr Lys Ala Met Trp Arg Glu Ala Lys Glu Cys Leu Tyr
        350                 355                 360 gtt gag cct gac gtt ggt ggt ggt ggt ggt agc aaa ggt gtt ttt        1215
Val Glu Pro Asp Val Gly Gly Gly Gly Gly Ser Lys Gly Val Phe
    365                 370                 375 tgg tat cgt aac aag ttc taaagaccga ccaactgcct gatagctggc           1263
Trp Tyr Arg Asn Lys Phe
380             385 cggcgaaatc aacgtaaaac gtacttatta gactagtgtt aactagggaa gttaataatt  1323
aatggtagga aatgtggaa tagttgccta gtagttttat gtattaagtg ttgtattaat   1383
aaactatatg gtagaaaaaa aaaaaaaa                                     1411

<210> SEQ ID NO 4
<211> LENGTH: 385
<212> TYPE: PRT
<213> ORGANISM: Gossypium sp.

<400> SEQUENCE: 4

Met Gly Ala Gly Gly Arg Met Pro Ile Asp Gly Ile Lys Glu Glu Asn
```

```
            1               5                10               15
Arg Gly Ser Val Asn Arg Val Pro Ile Glu Lys Pro Pro Phe Thr Leu
                    20              25                30

Gly Gln Ile Lys Gln Ala Ile Pro Pro His Cys Phe Arg Arg Ser Leu
                35              40                  45

Leu Arg Ser Phe Ser Tyr Val His Asp Leu Cys Leu Ala Ser Phe
        50              55              60

Phe Tyr Tyr Ile Ala Thr Ser Tyr Phe His Phe Leu Pro Gln Pro Phe
65              70              75                          80

Ser Tyr Ile Ala Trp Pro Val Tyr Trp Val Leu Gln Gly Cys Ile Leu
                    85              90                  95

Thr Gly Val Trp Val Ile Ala His Glu Trp Gly His His Ala Phe Arg
                100             105             110

Asp Tyr Gln Trp Val Asp Asp Thr Val Gly Leu Ile Leu His Ser Ala
                115             120             125

Leu Leu Val Pro Tyr Phe Ser Trp Lys Ile Ser His Arg Arg His His
        130             135             140

Ser Asn Thr Gly Ser Met Glu Arg Asp Glu Val Phe Val Pro Lys Pro
145             150             155                         160

Lys Ser Lys Leu Ser Cys Phe Ala Lys Tyr Leu Asn Asn Pro Pro Gly
                165             170             175

Arg Val Leu Ser Leu Val Val Thr Leu Thr Leu Gly Trp Pro Met Tyr
                180             185             190

Leu Ala Phe Asn Val Ser Gly Arg Tyr Tyr Asp Arg Leu Ala Ser His
            195             200             205

Tyr Asn Pro Tyr Gly Pro Ile Tyr Ser Asp Arg Glu Arg Leu Gln Val
    210             215             220

Tyr Ile Ser Asp Thr Gly Ile Phe Ala Val Ile Tyr Val Leu Tyr Lys
225             230             235                         240

Ile Ala Ala Thr Lys Gly Leu Ala Trp Leu Leu Cys Thr Tyr Gly Val
                245             250             255

Pro Leu Leu Ile Val Asn Ala Phe Leu Val Leu Ile Thr Tyr Leu Gln
            260             265             270

His Thr His Ser Ala Leu Pro His Tyr Asp Ser Ser Glu Trp Asp Trp
        275             280             285

Leu Arg Gly Ala Leu Ser Thr Met Asp Arg Asp Phe Gly Val Leu Asn
        290             295             300

Lys Val Phe His Asn Ile Thr Asp Thr His Val Ala His His Leu Phe
305             310             315                         320

Ser Thr Met Pro His Tyr His Ala Met Glu Ala Thr Lys Ala Ile Lys
                325             330             335

Pro Ile Leu Gly Lys Tyr Tyr Pro Phe Asp Gly Thr Pro Ile Tyr Lys
            340             345             350

Ala Met Trp Arg Glu Ala Lys Glu Cys Leu Tyr Val Glu Pro Asp Val
            355             360             365

Gly Gly Gly Gly Gly Ser Lys Gly Val Phe Trp Tyr Arg Asn Lys
    370             375             380

Phe
385

<210> SEQ ID NO 5
<211> LENGTH: 1422
<212> TYPE: DNA
<213> ORGANISM: Gossypium sp.
```

<220> FEATURE:
<221> NAME/KEY: CDS
<222> LOCATION: (98)..(1246)

<400> SEQUENCE: 5

```
taaaaaaaaa aggcatttct ttcatcttaa agagacagcg aggaagccac gaagataata      60
gagtgatttt caatctccat tttaagggtg tggaaca atg ggt gct gga ggc aga     115
                                        Met Gly Ala Gly Gly Arg
                                          1               5 atg tcg gtt cca acg agt cca aaa aaa ccc gaa ttc aac tca ctg aag      163
Met Ser Val Pro Thr Ser Pro Lys Lys Pro Glu Phe Asn Ser Leu Lys
         10                  15                  20 cga gtt cca tac tca aag cca ccc ttc act ctg agt gaa atc aag aaa      211
Arg Val Pro Tyr Ser Lys Pro Pro Phe Thr Leu Ser Glu Ile Lys Lys
             25                  30                  35 gcc atc cca cca cac tgt ttc cag cgc tcc gtt tta cgc tca ttc tca      259
Ala Ile Pro Pro His Cys Phe Gln Arg Ser Val Leu Arg Ser Phe Ser
 40                  45                  50 tat ctc ctt tac gac ttt ata ttg gcc tct ctt ttt tac cat gtg gcc      307
Tyr Leu Leu Tyr Asp Phe Ile Leu Ala Ser Leu Phe Tyr His Val Ala
 55                  60                  65                  70 acc aat tac ttc cct aac ctt cct cag gct ctc tcc aac gtg gct tgg      355
Thr Asn Tyr Phe Pro Asn Leu Pro Gln Ala Leu Ser Asn Val Ala Trp
                 75                  80                  85 cct ctt tat tgg gcc atg caa ggt tgc att ttg acc ggc gtt tgg gtc      403
Pro Leu Tyr Trp Ala Met Gln Gly Cys Ile Leu Thr Gly Val Trp Val
             90                  95                 100 ata gcc cat gaa tgt ggc cac cat gct ttc agt gat tat caa tgg ctt      451
Ile Ala His Glu Cys Gly His His Ala Phe Ser Asp Tyr Gln Trp Leu
            105                 110                 115 gac gac acc gtg ggc ctt atc ctc cac tct tct ctc tta gtt cca tat      499
Asp Asp Thr Val Gly Leu Ile Leu His Ser Ser Leu Leu Val Pro Tyr
120                 125                 130 ttc tct tgg aaa tat agc cac cgg cgt cac cat tct aac acc ggt tcc      547
Phe Ser Trp Lys Tyr Ser His Arg Arg His His Ser Asn Thr Gly Ser
135                 140                 145                 150 ctc gaa agg gat gaa gtg ttc gtt ccc aag aaa aaa tct ggt tta aga      595
Leu Glu Arg Asp Glu Val Phe Val Pro Lys Lys Lys Ser Gly Leu Arg
                155                 160                 165 tgg tgg gcc aaa cac ttc aac aat cca ccg ggt cgg ttt ctg tca atc      643
Trp Trp Ala Lys His Phe Asn Asn Pro Pro Gly Arg Phe Leu Ser Ile
            170                 175                 180 acc att caa ctt acc ctt ggt tgg ccg ctt tac tta gct ttc aac gtt      691
Thr Ile Gln Leu Thr Leu Gly Trp Pro Leu Tyr Leu Ala Phe Asn Val
        185                 190                 195 gcc ggc cgg cct tac gac agg ttc gct tgc cac tat gac cct tac ggc      739
Ala Gly Arg Pro Tyr Asp Arg Phe Ala Cys His Tyr Asp Pro Tyr Gly
200                 205                 210 ccc ata ttt tcc gac cgg gaa cga ctc caa atc tat atc tct gac gcc      787
Pro Ile Phe Ser Asp Arg Glu Arg Leu Gln Ile Tyr Ile Ser Asp Ala
215                 220                 225                 230 ggc gtc ctc gct gtc gcc tat gcg ctc tac cgt ctc gtg ttg gcc aaa      835
Gly Val Leu Ala Val Ala Tyr Ala Leu Tyr Arg Leu Val Leu Ala Lys
                235                 240                 245 ggg gta ggt tgg gtt att agc gtt tat ggg gtg cca tta ttg gtg gtt      883
Gly Val Gly Trp Val Ile Ser Val Tyr Gly Val Pro Leu Leu Val Val
            250                 255                 260 aac gcc ttc tta gta atg atc acg tat ttg caa cac act cac cca tct      931
Asn Ala Phe Leu Val Met Ile Thr Tyr Leu Gln His Thr His Pro Ser
        265                 270                 275
```

```
ttg ccg cac tat gat tcc tcg gag tgg gac tgg atg aga gga gct tta      979
Leu Pro His Tyr Asp Ser Ser Glu Trp Asp Trp Met Arg Gly Ala Leu
    280                 285                 290 tca act gtg gac aga gat tat ggg att tta aac aag gtt ttc cat aac     1027
Ser Thr Val Asp Arg Asp Tyr Gly Ile Leu Asn Lys Val Phe His Asn
295                 300                 305                 310 ata acc gac act cat gtg gct cat cat ttg ttt tcg aca atg cct cac     1075
Ile Thr Asp Thr His Val Ala His His Leu Phe Ser Thr Met Pro His
                315                 320                 325 tat cat gcc atg gtg gcc acc aag gcg ata aag ccc ata ttg ggg gaa     1123
Tyr His Ala Met Val Ala Thr Lys Ala Ile Lys Pro Ile Leu Gly Glu
            330                 335                 340 tac tat cag ttc gat ggg atg cct gtc tat aag gcg ata tgg agg gag     1171
Tyr Tyr Gln Phe Asp Gly Met Pro Val Tyr Lys Ala Ile Trp Arg Glu
        345                 350                 355 gcg aag gag tgt ctc tac gtt gaa cca gat gag ggc gac aag gat aaa     1219
Ala Lys Glu Cys Leu Tyr Val Glu Pro Asp Glu Gly Asp Lys Asp Lys
    360                 365                 370 ggt gtg ttt tgg ttt aga aac aag ctt taaatatttg cattttacct           1266
Gly Val Phe Trp Phe Arg Asn Lys Leu
375                 380 taggcatgtt ctagtcgttg atgttttaag gatattttag ccgacatact tggttttcct   1326
ttttgggact tttagctttt gtatttgcag acaataatct tgttcactat taaataatgg   1386
tagaaataaa tacacagcat ggattggcaa taaaaa                             1422

<210> SEQ ID NO 6
<211> LENGTH: 383
<212> TYPE: PRT
<213> ORGANISM: Gossypium sp.

<400> SEQUENCE: 6

Met Gly Ala Gly Gly Arg Met Ser Val Pro Thr Ser Pro Lys Lys Pro
1               5                   10                  15

Glu Phe Asn Ser Leu Lys Arg Val Pro Tyr Ser Lys Pro Pro Phe Thr
            20                  25                  30

Leu Ser Glu Ile Lys Lys Ala Ile Pro Pro His Cys Phe Gln Arg Ser
        35                  40                  45

Val Leu Arg Ser Phe Ser Tyr Leu Leu Tyr Asp Phe Ile Leu Ala Ser
    50                  55                  60

Leu Phe Tyr His Val Ala Thr Asn Tyr Phe Pro Asn Leu Pro Gln Ala
65                  70                  75                  80

Leu Ser Asn Val Ala Trp Pro Leu Tyr Trp Ala Met Gln Gly Cys Ile
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Leu His Ser
        115                 120                 125

Ser Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Gly Leu Arg Trp Trp Ala Lys His Phe Asn Asn Pro Pro
                165                 170                 175

Gly Arg Phe Leu Ser Ile Thr Ile Gln Leu Thr Leu Gly Trp Pro Leu
            180                 185                 190
```

-continued

```
Tyr Leu Ala Phe Asn Val Ala Gly Arg Pro Tyr Asp Arg Phe Ala Cys
        195                 200                 205

His Tyr Asp Pro Tyr Gly Pro Ile Phe Ser Asp Arg Glu Arg Leu Gln
    210                 215                 220

Ile Tyr Ile Ser Asp Ala Gly Val Leu Ala Val Ala Tyr Ala Leu Tyr
225                 230                 235                 240

Arg Leu Val Leu Ala Lys Gly Val Gly Trp Val Ile Ser Val Tyr Gly
                245                 250                 255

Val Pro Leu Leu Val Val Asn Ala Phe Leu Val Met Ile Thr Tyr Leu
            260                 265                 270

Gln His Thr His Pro Ser Leu Pro His Tyr Asp Ser Ser Glu Trp Asp
        275                 280                 285

Trp Met Arg Gly Ala Leu Ser Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Val Ala Thr Lys Ala Ile
                325                 330                 335

Lys Pro Ile Leu Gly Glu Tyr Tyr Gln Phe Asp Gly Met Pro Val Tyr
            340                 345                 350

Lys Ala Ile Trp Arg Glu Ala Lys Glu Cys Leu Tyr Val Glu Pro Asp
        355                 360                 365

Glu Gly Asp Lys Asp Lys Gly Val Phe Trp Phe Arg Asn Lys Leu
    370                 375                 380

<210> SEQ ID NO 7
<211> LENGTH: 5006
<212> TYPE: DNA
<213> ORGANISM: Gossypium sp.
<220> FEATURE:
<221> NAME/KEY: 5'UTR
<222> LOCATION: (3785)..(5006)
<221> NAME/KEY: intron
<222> LOCATION: (3889)..(4998)

<400> SEQUENCE: 7
ttatttaggc ttttataggc atttaatagg gaggaatttt gaaaaatttc atgaataaag      60
atacaaatct actgagaaaa aattaaaata cgtattggac taaaacatcc ataagcctaa     120
aaaggcccaa ctaatccaaa caaaacttga gtgttacaat ctaaccctag tctggcaacg     180
gatacgggtt aagggtgtta caacctttac agtgatcaac gaacaaacct tgagtggatt     240
tggatttgac cccctaccc cactacacac aaggaagaat gttagtttag ttattcaata     300
gctactaagt tggtttacat atatatacaa gttccacact tgattctcaa tcaatgtgag     360
actaatgctt ttcatttctc tcaacataat tcacaagtag cttactttga gtatcaattt     420
ttcattcatc actcaatcat tttgagcata tgatatattg ttgtaaatgt ctaatggagt     480
agaatataaa attataattt tatgattcaa cttttcacct ttaccaatag aaaatatgcc     540
tcaaagtttt caaaaaatca tatttttct aatagaaata actttagaca tcaagaatct     600
acgaataaaa tttaaataac ttttttctcc aatcttcgat acttgctatt aaattaactt     660
aaattcttct acttgagatt tgatgcatg cgacaaaaat tgagattaga atccatgatg     720
tggaaagcaa aacaaatatg taagcaaata ttgtcttgtc gtaaaaccat ttgatttttt     780
ttttcaatca ttcattgaaa ttgaagtccc tcaatgaagc catcacataa tatgttacat     840
aaaagttaga aacttaaacg tgatgatgca tgaacctctc taatttcact ctccaaaatt     900
```

-continued

```
catacagcaa gcgatacttc caatgaccca aaattattga aaccaatgtg cttttcctat    960
cattgaaaat cgtgatggag ccacttgtaa cattgtttgc gtacatactt attattatta   1020
ttattattaa tattttattg ataaaagtat tagaaattt tgtattaaaa gtcagattat    1080
attttatatt ttaaaaataa ataagttagt cattctgtgt tagatcaaat agcaaaacaa  1140
tagaaataga tgaaattttc aataaaaaag gaccagttta ctctttgaac taacgcacaa  1200
tgactaattt accattttta gtagatgagg taaaatataa tctagctcct tgtacagggg  1260
cttccgtgat acttttaccc tattgtatct cttctcaacg ataaataaaa atatgtttta  1320
gaaaattttg tttccaaaga taattacaaa gttaagtcaa acaagcagta acattgtttc  1380
acttaatttc cctttcgaaa gaaaaactct tatttagaat aattgtcatt caaagtaact  1440
attttttta gaacagctat gcttggaaca atcatgttta gaacatggct ccattttaga   1500
atatggttgt cgtttgagaa caactcctgc aaaggataac gaatgtttgg aacagttctt   1560
atttagaata actgcgtttc aagaataatc atatttagaa caacctccat ttaaaacaat   1620
agtggttttt tttaaaaaga agagatatta ttcaaaatta gctctttcaa gaaaagcatc   1680
accatagaac aactattatt aaaaataaag ctaaattcac aatttggccc ttgaagtata   1740
ctcattttt gactttggta tctaaacttt tctttgcctc aatttgatac ctaaaatact   1800
ctcaaattcc attttttgac agacattaaa aaaataatct tatagccaat cacaaagcgc  1860
cacgtggcgt ctttatgtaa aaagaaatat tttgtttaat taaatgtata tacacattaa  1920
aaaataaaaa aatatagaac aacatataaa ttataaacaa atctataaaa ataaaattta  1980
caaaaataca ataattgaaa aaaaattagt tgaaattaat aatattatta aaaaatgtaa  2040
aacatttgta aaaattataa aaagtttta aaaataattt tctttataaa attctaaaat  2100
atataattct aaaattgtaa aaaggtatat aaatttcatt tttttcaatt actcgaaatt  2160
taaatacttt ttcaatttttt ataacacttt tttaattttt atatattatt ttggatttt    2220
aaaatttata attatatatt tcaaaatttt ataaattttt ttatatgtta tatatgatt    2280
tttacattt taatcaatat aatataaaat actaaatttt tttaaaaaaa tgatacgtgg   2340
catgttctaa tatcgccaca tgaccggtga acgctcggtc aatggccagt caaagccaaa  2400
agtatttttt taatatttaa ataattaatt ttatacttct attttttaatt ttaattaat  2460
atttttattt taaataaact taattgttat gtgatatttt ttcactgacc caaaacatgc  2520
tatgtggagc ttttcccatt agccaaagtt gccaaataga tttttcaac gtgtgttaca    2580
aaatggaccg aaaatagagg aaattgatac tttaggtatc aagttgggat aaaaaaagtt  2640
taggtaccaa agtaaaaaat ttggtatact ttaggggcta aatcataaat taagcctaaa  2700
gacaattata ttgagaataa attaggttta gaacgggtca aaataattct tattcagtaa  2760
caacttttgt tcaagaacaa ctcttcaata acaaaagttt gtatttcacg agatgctctt  2820
atttttgtt caatatattt atttgtgcac tgtaatgatc gattttaatc aaacataaat  2880
aaatgtcttg attgtgattg taattttttc ttagttgtac aaatatattg attataattg  2940
tgatggaaaa aaataaaaaa aattaaattt tagatgaata aagagtacat gggctataat  3000
tagaattaac ctaaatttgt ttggttataa ctagaggttt tggttcaaag aattaatttc  3060
taaatccgag tccaacccgc tttgatcag ccaaaggttc ttttaaatta ttttaattat   3120
ttatatttaa attaaataat aaaatatata aatataatat aatttcatca tttattgaat  3180
cgagttaatc caaaattgaa gaatataaac tcaaactcga ctcaagatga atcgaaccgc  3240
ttgactaaac tgacccaacc caacttgttt ttgagctaag tttgagttta atattttcaa  3300
```

```
cttcacgttg gcttgaccca gactgattaa ttattaaaca actaaaagaa ttttaatata    3360
catttgaatt taaatttaaa taaaaagtat taatataaga tctgtgaaaa gtcgtattta    3420
gtgattatat gatttatgtt taatttaaat gttaattatt tatatttact tcaacaatag    3480
tagtaacatt ctgtaatatg aatatgaatc cgatgattga gaagtgagag gtgttacata    3540
tttactaccg aggaatacct ttccttccac gatgaagtcc ttatcgttgc aacaggtgtt    3600
tgggagatat caaaagagg cggggtaatg atgatgatga aagcgagaat catcagaatc     3660
agaaaaaagg gaaagggtg attaaagaaa agactctcat cctcactgat tctggtcttg     3720
cttcccaaca cgtagcatct aaccataacg cctcaaatcc gctgctcctc tatttatttc    3780
aaaaccactt gattaagctc cccctccgct ccataccact cgcccaaaac caacacgcct    3840
tctttgcctc gtgtttcatc acctggcgtt aaactgcttt ctttaaaggt acatttctct    3900
ttaatttcct ttttttttca tttcatgttt ttcatgttaa tgttgcattg aagtgataaa    3960
tttgagtgaa tgatgtttgg tatatcttct tagtaactga ccttttgaaa atactagcat    4020
tttttttaat atcaagtgaa agaagaagaa gaatttcgcc atgcaaaagc ttttaaggc    4080 tttttctttt ccttagatca aaatttattt gtttacttat actgttcttt taagcccgaa    4140
gaaagaagcc atggtttcaa tttttgagag ttttaaatcc caaataccag agagcttcat    4200
cgtttattca tatatttta aacatttttt aaagcaagaa cttgtgattt gtttttaata    4260
aaatatgcaa taaattttta tattttcgt aaatttaaaa tttaattttt ctacttttaa    4320
aatttaaaaa agtaaatttt aaaatatacc tttcattaaa ttaaattatt ataagtaatt    4380
gagtattttt aattttaaaa tttcacacat caaattaaaa aaaaagttaa cacttgcact    4440
tgattttgaa aagtaaaagg attaaatttc aaattttcag taaaaggact aaatttcaaa    4500
tttttaaaga gtatagagac tcctctacat tttagatttt aaaatttaaa tctaacagtt    4560
aacactttct taattacttt acgataaatt taactaaaaa attacaatat taatggttaa    4620
aattaaattt tgaaaagtat aaagattaaa ttgtaaattt tcaaaaagca taggaagtta    4680
tagtatattt taacctttat ttattttata tctggtgagg ttcctgcatg caccgaagat    4740
gtcacctttt gccagtattt tccagtggct tgtttctctc aaaactacct tgaatcttga    4800
gacagaatta aatatatttt tggccttttc ttcattttct ctctctctat tttcttttaa    4860
aaattgcttt agagaattca gaaaaaatac tttccaacac gaaaatttct tcaaatttat    4920
tgtttatatc taataaatgg ttgcttaatt ttggaaaaca aaagttattg tagttagttt    4980
tgcttcttgc gtgtccagcc agcaaa                                         5006
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:synthetic
    oligonucleotide useful as a primer

<400> SEQUENCE: 8
atggckctsa rgctbcatsc                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:synthetic oligonucleotide useful as a primer

<400> SEQUENCE: 9
tcasagyttm acytgyctat                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 10
gcataggtca tggaccacgt                                                    20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 11
gtaaaacgac ggccagt                                                       17

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 12
ggaaacagct atgaccatg                                                     19

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 13 ggcccggg                                                                  8

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 14 ggccccg                                                                   8

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 15
ttttaatgcc atcgcctcg                                          19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 16
cttcagcagt ccaagccctg                                         20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 17
cctggcgtta aactgctttc                                         20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 18
ccatatagtt tattaatata acac                                    24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 19
tatgttgcaa gtaggtgatc                                         20

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 20
acgcgtcgac gtgtgttaca aaatggaccg aa                           32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence:synthetic
      oligonucleotide useful as a primer -continued

```
<400> SEQUENCE: 21
cgcggatccg ctggctggac acgcaagaag ca                                32

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 22
cgagctcccc ctccgctcca taccact                                      27

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 23
cgcggatccg ctggctttaa agaaagcagt t                                 31

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 24
catgtgacag atcgaaggaa                                              20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:synthetic
      oligonucleotide useful as a primer

<400> SEQUENCE: 25
atctaattat tctattcaga c                                            21

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:synthetic
      peptide
<221> NAME/KEY: UNSURE
<222> LOCATION: (1)..(6)
<223> OTHER INFORMATION: Xaa at  position 3 is either Trp or Cys

<400> SEQUENCE: 26

His Glu Xaa Gly His His
  1               5

<210> SEQ ID NO 27
<211> LENGTH: 5
<212> TYPE: PRT
<213> ORGANISM: Artificial Sequence
<220> FEATURE:
```

```
<223> OTHER INFORMATION: Description of Artificial Sequence:synthetic
      peptide

<400> SEQUENCE: 27

His Arg Arg His His
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 28

His Val Ala His His
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:synthetic
      peptide
<221> NAME/KEY: UNSURE
<222> LOCATION: (1)..(5)
<223> OTHER INFORMATION: Xaa at position 2  is any amino acid; Xaa at
      position 3 is any amino acid

<400> SEQUENCE: 29

His Xaa Xaa His His
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:synthetic
      peptide
<221> NAME/KEY: UNSURE
<222> LOCATION: (1)..(6)
<223> OTHER INFORMATION: Xaa at position 2 is any amino acid; Xaa at
      position 3 is any amino acid; Xaa at position 4 is
      any amino acid

<400> SEQUENCE: 30

His Xaa Xaa Xaa His His
 1               5

<210> SEQ ID NO 31
<211> LENGTH: 383
<212> TYPE: PRT
<213> ORGANISM: Glycine max

<400> SEQUENCE: 31

Met Gly Ala Gly Gly Arg Thr Asp Val Pro Pro Ala Asn Arg Lys Ser
 1               5                  10                  15

Glu Val Asp Pro Leu Lys Arg Val Pro Phe Glu Lys Pro Gln Phe Ser
                20                  25                  30

Leu Ser Gln Ile Lys Lys Ala Ile Pro Pro His Cys Phe Gln Arg Ser
             35                  40                  45

Val Leu Arg Ser Phe Ser Tyr Val Val Tyr Asp Leu Thr Ile Ala Phe
         50                  55                  60
```

-continued

```
Cys Leu Tyr Tyr Val Ala Thr His Tyr Phe His Leu Pro Gly Pro
 65                  70                  75                  80

Leu Ser Phe Arg Gly Met Ala Ile Tyr Trp Ala Val Gln Gly Cys Ile
                 85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
                165                 170                 175

Gly Arg Val Leu Thr Leu Ala Val Thr Leu Thr Leu Gly Trp Pro Leu
            180                 185                 190

Tyr Leu Ala Leu Asn Val Ser Gly Arg Pro Tyr Asp Arg Phe Ala Cys
        195                 200                 205

His Tyr Asp Pro Tyr Gly Pro Ile Tyr Ser Asp Arg Glu Arg Leu Gln
    210                 215                 220

Ile Tyr Ile Ser Asp Ala Gly Val Leu Ala Val Val Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
            260                 265                 270

Gln His Thr His Pro Ala Leu Pro His Tyr Thr Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val
            340                 345                 350

Lys Ala Met Trp Arg Glu Ala Arg Glu Cys Ile Tyr Val Glu Pro Asp
        355                 360                 365

Gln Ser Thr Glu Ser Lys Gly Val Phe Trp Tyr Asn Asn Lys Leu
    370                 375                 380
```

<210> SEQ ID NO 32
<211> LENGTH: 383
<212> TYPE: PRT
<213> ORGANISM: Arabidopsis thaliana

<400> SEQUENCE: 32

```
Met Gly Ala Gly Gly Arg Met Pro Val Pro Thr Ser Ser Lys Lys Ser
 1               5                  10                  15

Glu Thr Asp Thr Thr Lys Arg Val Pro Cys Glu Lys Pro Pro Phe Ser
                 20                  25                  30

Val Gly Asp Leu Lys Lys Ala Ile Pro Pro His Cys Phe Lys Arg Ser
            35                  40                  45

Ile Pro Arg Ser Phe Ser Tyr Leu Ile Ser Asp Ile Ile Ile Ala Ser
        50                  55                  60
```

```
Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380

<210> SEQ ID NO 33
<211> LENGTH: 387
<212> TYPE: PRT
<213> ORGANISM: Glycine max

<400> SEQUENCE: 33

Met Gly Leu Ala Lys Glu Thr Thr Met Gly Gly Arg Gly Arg Val Ala
 1               5                  10                  15

Lys Val Glu Val Gln Gly Lys Lys Pro Leu Ser Arg Val Pro Asn Thr
                 20                  25                  30

Lys Pro Pro Phe Thr Val Gly Gln Leu Lys Lys Ala Ile Pro Pro His
             35                  40                  45

Cys Phe Gln Arg Ser Leu Leu Thr Ser Phe Ser Tyr Val Val Tyr Asp
```

```
             50                  55                  60
Leu Ser Phe Ala Phe Ile Phe Tyr Ile Ala Thr Thr Tyr Phe His Leu
 65                  70                  75                  80

Leu Pro Gln Pro Phe Ser Leu Ile Ala Trp Pro Ile Tyr Trp Val Leu
                 85                  90                  95

Gln Gly Cys Leu Leu Thr Gly Val Trp Val Ile Ala His Glu Cys Gly
                100                 105                 110

His His Ala Phe Ser Lys Tyr Gln Trp Val Asp Asp Val Val Gly Leu
            115                 120                 125

Thr Leu His Ser Thr Leu Leu Val Pro Tyr Phe Ser Trp Lys Ile Ser
130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
            195                 200                 205

Ser Phe Ala Ser His Tyr His Pro Tyr Ala Pro Ile Tyr Ser Asn Arg
210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
            275                 280                 285

Ser Glu Trp Asp Trp Leu Lys Gly Ala Leu Ala Thr Met Asp Arg Asp
290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
            355                 360                 365

Val Glu Pro Asp Glu Gly Thr Ser Glu Lys Gly Val Tyr Trp Tyr Arg
370                 375                 380

Asn Lys Tyr
385

<210> SEQ ID NO 34
<211> LENGTH: 377
<212> TYPE: PRT
<213> ORGANISM: Brassica napus

<400> SEQUENCE: 34

Met Val Val Ala Met Asp Gln Arg Ser Asn Ala Asn Gly Asp Glu Arg
  1               5                  10                  15

Phe Asp Pro Ser Ala Gln Pro Pro Phe Lys Ile Gly Asp Ile Arg Ala
                 20                  25                  30
```

Ala Ile Pro Lys His Cys Trp Val Lys Ser Pro Leu Arg Ser Met Ser
          35                  40                  45

Tyr Val Ala Arg Asp Ile Phe Ala Val Val Ala Leu Ala Val Ala Ala
 50                  55                  60

Val Tyr Phe Asp Ser Trp Phe Phe Trp Pro Leu Tyr Trp Ala Ala Gln
 65                  70                  75                  80

Gly Thr Leu Phe Trp Ala Ile Phe Val Leu Gly His Asp Cys Gly His
                 85                  90                  95

Gly Ser Phe Ser Asp Ile Pro Leu Leu Asn Thr Ala Val Gly His Ile
             100                 105                 110

Leu His Ser Phe Ile Leu Val Pro Tyr His Gly Trp Arg Ile Ser His
         115                 120                 125

Arg Thr His His Gln Asn His Gly His Val Glu Asn Asp Glu Ser Trp
 130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                 165                 170                 175

Leu Trp Tyr Arg Ser Pro Gly Lys Glu Gly Ser His Tyr Asn Pro Tyr
             180                 185                 190

Ser Ser Leu Phe Ala Pro Ser Glu Arg Lys Leu Ile Ala Thr Ser Thr
         195                 200                 205

Thr Cys Trp Ser Ile Met Leu Ala Thr Leu Val Tyr Leu Ser Phe Leu
 210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His Gly His
                 245                 250                 255

Asp Asp Lys Leu Pro Trp Tyr Arg Gly Lys Glu Trp Ser Tyr Leu Arg
             260                 265                 270

Gly Gly Leu Thr Thr Ile Asp Arg Asp Tyr Gly Ile Phe Asn Asn Ile
         275                 280                 285

His His Asp Ile Gly Thr His Val Ile His His Leu Phe Pro Gln Ile
 290                 295                 300

Pro His Tyr His Leu Val Asp Ala Thr Lys Ser Ala Lys His Val Leu
305                 310                 315                 320

Gly Arg Tyr Tyr Arg Glu Pro Lys Thr Ser Gly Ala Ile Pro Ile His
                 325                 330                 335

Leu Val Glu Ser Leu Val Ala Ser Ile Lys Lys Asp His Tyr Val Ser
             340                 345                 350

Asp Thr Gly Asp Ile Val Phe Tyr Glu Thr Asp Pro Asp Leu Tyr Val
         355                 360                 365

Tyr Ala Ser Asp Lys Ser Lys Ile Asn
 370                 375

<210> SEQ ID NO 35
<211> LENGTH: 424
<212> TYPE: PRT
<213> ORGANISM: Glycine max

<400> SEQUENCE: 35

Met Ala Cys Thr Leu Ala Asp Ser Leu Leu Leu Phe Lys Gly Ser Tyr
  1               5                  10                  15

Gln Lys Pro Val Leu Arg Arg Asp Ile Ala Ala Arg Tyr Ser Pro Gly
             20                  25                  30

-continued

```
Ile Phe Ser Leu Asn Ser Asn Gly Leu Ile Gln Lys Arg Phe Arg Arg
         35                  40                  45
Gln Arg Asn Phe Val Thr Arg Asn Lys Val Thr Val Ile His Ala Val
     50                  55                  60
Ala Ile Pro Val Gln Pro Ala Pro Val Glu Ser Ala Glu Tyr Arg Lys
 65                  70                  75                  80
Gln Leu Ala Glu Asp Tyr Gly Phe Arg Gln Val Gly Glu Pro Leu Ser
                 85                  90                  95
Asp Asp Val Thr Leu Lys Asp Val Ile Asn Pro Leu Pro Lys Glu Val
            100                 105                 110
Phe Glu Ile Asp Asp Val Lys Ala Trp Lys Ser Val Leu Ile Ser Val
            115                 120                 125
Thr Ser Tyr Ala Leu Gly Leu Phe Met Ile Ser Lys Ala Pro Trp Tyr
        130                 135                 140
Leu Leu Pro Leu Ala Trp Val Trp Thr Gly Thr Ala Ile Thr Gly Phe
145                 150                 155                 160
Phe Val Ile Gly His Asp Cys Ala His Arg Ser Phe Ser Ser Asn Lys
                165                 170                 175
Leu Val Glu Asp Ile Val Gly Thr Leu Ala Phe Met Pro Leu Ile Tyr
            180                 185                 190
Pro Tyr Glu Pro Trp Arg Phe Lys His Asp Arg His His Ala Lys Thr
        195                 200                 205
Asn Met Leu Arg Glu Asp Thr Ala Trp His Pro Val Trp Lys Asp Glu
    210                 215                 220
Phe Glu Ser Thr Pro Leu Leu Arg Lys Ala Ile Ile Tyr Gly Tyr Gly
225                 230                 235                 240
Pro Phe Arg Cys Trp Met Ser Ile Ala His Trp Leu Met Trp His Phe
                245                 250                 255
Asp Leu Lys Lys Phe Arg Pro Ser Glu Val Pro Arg Val Lys Ile Ser
            260                 265                 270
Leu Ala Cys Val Phe Ala Phe Ile Ala Ile Gly Trp Pro Leu Ile Ile
        275                 280                 285
Tyr Lys Thr Gly Ile Met Gly Trp Ile Lys Phe Trp Leu Met Pro Trp
    290                 295                 300
Leu Gly Tyr His Phe Trp Met Ser Thr Phe Thr Met Val His His Thr
305                 310                 315                 320
Ala Pro Tyr Ile Pro Phe Lys Tyr Ser Glu Glu Trp Asn Arg Ala Gln
                325                 330                 335
Ala Gln Leu Asn Gly Thr Val His Cys Asp Tyr Pro Lys Trp Ile Glu
            340                 345                 350
Ile Leu Cys His Asp Ile Asn Val His Ile Pro His His Ile Ser Pro
        355                 360                 365
Arg Ile Pro Ser Tyr Asn Leu Arg Ala Ala His Lys Ser Leu Gln Glu
    370                 375                 380
Asn Trp Gly Gln Tyr Leu Asn Glu Ala Ser Trp Asn Trp Arg Leu Met
385                 390                 395                 400
Lys Thr Ile Met Thr Val Cys Gln Val Tyr Asp Lys Glu Lys Ser Leu
                405                 410                 415
Cys Cys Leu Arg Arg Thr Cys Pro
            420
```

METHOD OF MODIFYING THE CONTENT OF COTTONSEED OIL

RELATED APPLICATION DATA

This application claims priority from U.S. Ser. No. 60/198,124 filed on Apr. 18, 2000.

FIELD OF THE INVENTION

The invention relates to a novel method of modifying the fatty acid composition of cottonseed oils to improve their nutritional and functional characteristics and to the plants, plant parts and metabolites produced therefrom.

BACKGROUND OF THE INVENTION

Cottonseed is a valuable product of cotton. Cottonseed contains approximately 25% of cottonseed oil, a well-established commodity vegetable oil because of its use as either a food ingredient or as a cooking oil for food preparation (Cherry, 1984). The world production of cottonseed oil in 1997/98 was around 4 million tonnes, making it sixth in importance behind the oils of soybean, oil-palm, rapeseed, sunflower and groundnut (Oil World Annual, 1998).

Globally, cotton crops consist of four domesticated *Gossypium* spp., including the allotetraploid species *G. barbadense L.* and *G. hirsutum L.*, and the diploid species *G. arboreum L.* and *G. herbaceum L.* Of these four species, *G. hirsutum* (upland cotton) is the predominant species, accounting for the overwhelming majority of cotton production worldwide. Currently, most cottonseed oil is derived from *G. hirsutum*, possibly as a consequence of the fact that this species is the major worldwide source of cotton fibre, and, cotton crops are primarily grown for their fibre.

The major components of cottonseed oil are the saturated fatty acids, palmitic acid (C16:0) and stearic acid (C18:0); the monounsaturated fatty acid, oleic acid (C18:1); and the polyunsaturated fatty acids, linoleic acid (C18:2) and α-linolenic acid (C18:3). A typical cottonseed fatty acid profile contains high levels of palmitic acid (24%) and linoleic acid (54%), a moderate level of oleic acid (18%), and a very low level of stearic acid (3%) and α-linolenic acid (1%).

The number, position, and conformation of a double bond in each fatty acid present in the cottonseed influences the physical properties (such as melting temperature), chemical properties and nutritional value of the cottonseed oil, and the applications to which it may be put, particularly in the food industry.

For example, the presence of a carbon double bond in a monounsaturated fatty acid or polyunsaturated fatty acid lowers its melting temperature, compared to the melting temperature of a saturated fatty acid of the same carbon chain length, such that the C-18 unsaturated fatty acids, oleic acid, linoleic acid, and linolenic acid, are all liquid at ambient temperature.

Additionally, the susceptibility of a fatty acid to oxidation increases proportionately with the number of carbon double bonds present in the fatty acid molecule, dramatically reducing the suitability of oils containing polyunsaturated fatty acids to applications involving the use of prolonged heat in the presence of oxygen, such as cooking and other food service applications.

For applications that require solid fat components such as in solid cooking fats, shortenings, or margarines, it is necessary to have moderately high levels of saturated fatty acids, or the functionally equivalent trans-fatty acids. Trans-fatty acids have carbon double bonds in the trans-orientation rather than the naturally-occurring cis-orientation.

Currently, the unsaturated fatty acids are subjected to chemical hydrogenation, to improve their suitability in cooking and food service applications. Hydrogenated cottonseed oil is a valuable product, because cottonseed oil has a naturally-high level of palmitic acid, and desired melting properties can be readily achieved by the hydrogenation process. In this process, trans-fatty acids are produced as an artifact.

The nutritional quality of natural cottonseed oil, and hydrogenated cottonseed oil, has been questioned because of the reported adverse effects of both saturated fatty acids, and trans fatty acids (Wollett 1994). The contribution of high levels of some saturated fatty acids in the diet, particularly palmitic acid, to increased blood cholesterol, and more particularly to increased low density lipoprotein (LDL), is well-established. Elevated LDL in the blood has been associated with an enhanced risk of cardiovascular disease in humans. Moreover, trans-fatty acids also elevate LDL cholesterol in a manner similar to palmitic acid. Because of the proven association with risk of cardiovascular disease, nutritionists and health authorities generally recommend limiting the dietary intake of palmitic acid, and trans-fatty acids, to at least below 30% of total fat intake. Natural oils high in palmitic acid, and hydrogenated oils high in trans-fatty acids, are expected to lose favour as a consequence of these recommendations.

However, not all saturated fatty acids are associated with elevated cholesterol. For example, stearic acid is reported to have neutral effects on blood cholesterol (Wollett 1994). in this respect, the high melting temperature of stearic acid (approximately 70° C.) also makes it particularly suitable in solid fat applications. Accordingly, because of its neutral effects on blood cholesterol levels, a high stearic acid-containing oil is a desirable substitute for partially-hydrogenated plant oils currently used in margarine production. Because of its physicochemical properties, stearic acid is also suitable for use in the production of cosmetics, pharmaceuticals and candles (Topfer, 1995). Furthermore, novel cottonseed oil having approximately equal proportions of palmitic, stearic and oleic and therefore having considerable potential for use as a cocoa butter substitute.

Although polyunsaturated fatty acids are beneficial in terms of lipoprotein metabolism and cardiovascular health, they are highly susceptible to peroxidation.

In summary, because the major use of cotton seed oil is as a foodstuff, there is a need to develop improved oils that have enhanced human nutritional value, such as, for example, oils that have reduced palmitic acid and/or are high in stearic acid. Furthermore, there is also a need to improve the potential applications of cottonseed oil in the food industry, without the adverse health risks associated with using oils rich in many saturated fatty acids, by providing oils having novel unsaturated fatty acid profiles. For example, oils having high oleic acid content and/or low linoleic acid content have the desired physicochemical properties of a cooking oil, and do not require hydrogenation (Kinney 1996).

Furthermore, triacylglycerol composed of approximately equal proportions of palmitic acid, oleic acid, and stearic acid (i.e. POS-type triacylglycerol) has a very sharp melting temperature at around body temperature, making it particularly suitable as a substitute for cocoa butter in the manufacture of chocolate and other confectionery. (Fincke, 1976;

Gunstone et al., 1986). Currently, the seeds of the cocoa tree, *Theobroma cacao* L., are the sole source of cocoa butter, and, as a consequence, cocoa butter is often in short supply and costly. The development of cocoa butter substitutes is of considerable economic importance.

In some cases, plant breeders have been able to modify the fatty acid content or composition of seed-derived oils, by inducing mutations in fatty acid biosynthesis genes. Exposure of plant material, generally seeds, to certain mutagenic agents, such as radiation or chemical mutagens, combined with traditional plant breeding approaches, has successfully produced a wide range of novel fatty acid profiles in many oilseed crops, including mutants of rapeseed (Auld et al., 1992), sunflower (Soldatov, 1976) and soybean (Rahman et al., 1994), having increased oleic acid; mutants of soybean (Erickson et al., 1988), linseed (Rowland and Bhatty, 1990), and sunflower (Osorio et al., 1995), having increased palmitic acid: mutants of soybean (Fehr et al., 1991) having lowered palmitic acid; mutants of soybean (Graef et al., 1985: Rahman et al., 1996) and sunflower (Osorio et al., 1995) having increased stearic acid; and mutants of linseed (Green, 1986), soybean (Wilcox et al., 1984), and rapeseed (Robbelen and Nitsch, 1975) having lowered linolenic acid. In several cases this has led to the commercial exploitation of these mutants, such as in the development of commercial varieties of high-oleate sunflower (Miller et al., 1987) and low-linolenic linseed (Green et al., 1991) and rapeseed (Scarth et al., 1988) oils. However, in spite of such notable successes in most other oilseed crops, there are no reports of substantial genetic modification of fatty acid composition in cottonseed oil using induced mutagenesis.

As a result of extensive basic biochemical research over a number of decades, the pathway for synthesis of the predominant fatty acids and their subsequent assembly into the seed storage triglycerides (oils) is now well understood for many plant species. Nearly all of the enzymes involved in fatty acid metabolism have been identified, the biosynthetic steps catalysed therefor characterised, and the genes encoding said enzymes cloned. In particular, the genes encoding stearoyl-ACP Δ9-desaturases, and oleoyl-ACP Δ12 desaturases have been cloned from several oilseed species, as follows.

The cDNAs encoding fatty acid Δ9-desaturase (Δ9 stearoyl-ACP desaturase) enzymes from approximately 22 plant species, including castor bean (Shanklin and Somerville 1991), safflower (Thompson et al., 1991), and cotton (Liu et al., 1996) have been cloned, and the nucleotide sequences thereof made publicly available from the GenBank database. Antisense gene constructs comprising a nucleotide sequence complementary to the *Brassica rapa* stearoyl-ACP Δ9-desaturase cDNA have been used to decrease expression of the endogenous *B. napus* and *B. rapa* stearoyl-ACP Δ9-desaturase genes (Knutzon 1992), thereby increasing stearic acid at the expense of oleic acid in the seed oil. In this case, stearic acid was increased to 40% of total fatty acid in the seed.

With regard to fatty acid Δ12-desaturase genes, a cDNA containing the open reading frame of the *Arabidopsis thaliana* FAD2 gene has been isolated, and shown to complement the fad2 mutation of *A. thaliana*, which mutation produces a deficiency in the activity of the oleoyl-PC Δ12-desaturase enzyme (Miquel and Browse, 1992), indicating that the FAD2 gene encodes an oleoyl-PC Δ12-desaturase (Okuley et al., 1994). Kinney (1997) decreased expression of endogenous rapeseed and soybean fatty acid Δ12-desaturase genes, by using sense-suppression (cosuppression) and antisense-suppression gene constructs, to produce high oleic acid-containing oils. In that work, Kinney (1997) also reported the decreased expression of fatty acid Δ15-desaturase genes, to produce low linolenic acid-containing oils in both rapeseed and soybean. Cosuppression to reduce expression of an endogenous fatty acid Δ12-desaturase gene has also been reported to produce high oleic acid oils in *Brassica napus* and *Brassica juncea* (Stoutjesdijk et al., 1999).

U.S. Pat. No. 5,850,026 (Cargill, Inc.), dated 15 Dec., 1998, also reports the production of high oleic acid-containing oilseed in *Brassica* sp., by using antisense or cosuppression gene constructs directed simultaneously against microsomal fatty acid Δ12-desaturase and microsomal fatty acid Δ-15 desaturase gene expression. The oilseed reported by these workers was also low in erucic acid and α-linolenic acid.

U.S. Pat. No. 5,981,781 (E.I. du Pont de Nemours and Company), dated 9 Nov., 1999, teaches the use of cosuppression, to reduce expression of the soybean GmFAD2-1 gene, which encodes a fatty acid Δ12-desaturase (oleoyl-PC Δ12-desaturase) in that species. A high oleic acid-containing soybean oil, having high oxidative stability, was produced by this cosuppression.

More recently, Liu et al. (1999a, 1999b) have described a fatty acid Δ12-desaturase (oleoyl-PC Δ12-desaturase) gene from cotton.

Notwithstanding the considerable number of publicly-available plant fatty acid biosynthesis genes which have been cloned and characterised, and the reported modification of fatty acid levels in the oils of *Brassica* spp. and soybean using said genes, there is no reported modification of fatty acid metabolism in cotton, using either traditional plant breeding, mutational breeding, or recombinant DNA approaches. The tetraploid nature of cotton, and the existence of large families of specific fatty acid biosynthesis genes makes it difficult to determine those genes which, by virtue of being expressed in a seed-specific manner are suitable targets for silencing with a view to modifying oil seed composition.

Additionally, gene silencing is not a straightforward procedure as applied to cotton. There are only a few reports in the literature of the transformation of cotton using gene silencing gene constructs, and these reports are restricted to the use of antisense technology. For example, antisense technology has been used to reduce the expression of genes involved in fibre synthesis, however in that report the transgenic plants did not exhibit a detectable phenotype notwithstanding a reduction in enzyme biosynthesis, suggesting that the silencing of genes in cotton is unpredictable.

GENERAL

Those skilled in the art will be aware that the invention described herein is subject to variations and modifications other than those specifically described. It is to be understood that the invention described herein includes all such variations and modifications The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps. The present invention is not to be limited in scope by the specific embodiments described herein, which are intended for the purposes of exemplification only Functionally-equivalent products, compositions and methods are clearly within the scope of the invention, as described herein.

Bibliographic details of the publications referred to by author in this specification are collected at the end of the description. Reference herein to prior art, including any one or more prior art documents, is not to be taken as an acknowledgment, or suggestion, that said prior art is common general knowledge in Australia or forms a part of the common general knowledge in Australia.

As used herein, the term "derived from" shall be taken to indicate that a particular integer or group of integers has originated from the species specified, but has not necessarily been obtained directly from the specified source.

This specification contains nucleotide sequence information prepared using the program PatentIn Version 3.0, presented herein after the claims. Each nucleotide sequence is identified in the sequence listing by the numeric indicator <210> followed by the sequence identifier [e.g. <210>1, <210>2, etc]. The length, type of sequence [DNA, protein (PRT), etc] and source organism for each nucleotide sequence are indicated by information provided in the numeric indicator fields <211>, <212> and <213>, respectively. Nucleotide sequences referred to in the specification are defined by the term "SEQ ID NO:", followed by the sequence identifier [e.g. SEQ ID NO: 1 refers to the sequence in the sequence listing designated as <400>1].

The designation of nucleotide residues referred to herein are those recommended by the IUPAC-IUB Biochemical Nomenclature Commission, wherein A represents Adenine, C represents Cytosine, G represents Guanine, T represents thymidine, Y represents a pyrimidine residue, R represents a purine residue, M represents Adenine or Cytosine, K represents Guanine or Thymidine, S represents Guanine or Cytosine, W represents Adenine or Thymidine, H represents a nucleotide other than Guanine, B represents a nucleotide other than Adenine, V represents a nucleotide other than Thymidine, D represents a nucleotide other than Cytosine and N represents any nucleotide residue.

SUMMARY OF THE INVENTION

In work leading up to the present invention, the inventors sought to develop a modified cottonseed oil having improved nutritional and physicochemical characteristics, such as, for example, oils having improved oxidative stability and melting characteristics, without the need for hydrogenation, and oils having improved nutritional characteristics, by virtue of their modified fatty acid composition. More particularly, the inventors sought to develop specialty cottonseed oils which are low in palmitic acid and/or linoleic acid, and/or which are high in stearic acid and/or oleic acid, using a combination of recombinant DNA technology and classical plant breeding approaches. To achieve this objective, the inventors found it necessary to develop the means to reproducibly apply gene silencing approaches to cotton, and to identify specific fatty acid biosynthesis genes in cotton that are expressed in a seed-specific manner.

Accordingly, one aspect of the invention provides a method of modifying the endogenous oil of a cotton plant comprising producing a transgenic cotton plant having a gene construct which comprises a nucleotide sequence of a fatty acid biosynthesis gene or a gene fragment thereof, wherein said gene or gene fragment is placed operably in connection with a promoter sequence capable of conferring expression of said gene or gene fragment in the seed of a cotton plant, and wherein said fatty acid biosynthesis gene is selected from the group consisting of fatty acid Δ9-desaturase (Δ9 stearoyl-ACP desaturase) genes, and fatty acid Δ12-desaturase (Oleoyl-PC Δ12-desaturase) genes.

In accordance with this aspect of the invention, the inventors have isolated nucleic acid molecules which comprise nucleotide sequences encoding these fatty acid biosynthesis genes, such as, for example the nucleotide sequences of cotton exemplified herein as SEQ ID NOs: 1, 3, and 5. These nucleotide sequences have been used to develop novel gene constructs capable of producing overexpression, sense-suppression, cosuppression, antisense suppression, and post-transcriptional gene silencing (PTGS) of the various fatty acid genes of cotton.

The inventors have also isolated the genomic ghFAD2-1 gene of cotton encoding the Δ12-desaturase (oleoyl-PC Δ12desaturase) enzyme (Example 10). SEQ ID NO: 7 shows the nucleotide sequence of the ghFAD2-1 promoter. In this respect, SEQ ID NO: 7 contains sufficient nucleotide sequence to confer expression on a structural gene to which it is operably connected in the cottonseed. In particular, the 5006 nucleotides of SEQ ID NO: 7 includes 3784 nucleotides upstream of the transcription start site of the FAD2 gene (position 3785), the first intron of the gene (nucleotides 3889 to 4998) and the entire 5'-untranslated region (UTR) of the ghFAD2-1 gene (nucleotides 3785 to 5006).

In particular, the inventors developed gene constructs to facilitate the silencing or reduced seed-specific expression of cotton fatty acid Δ9-desaturase (Δ9 stearoyl-ACP desaturase) genes and cotton fatty acid Δ12-desaturase (Oleoyi-PC Δ12-desaturase) genes. The gene constructs have been introduced into cotton explants to produce transformed cells that have subsequently been regenerated into whole plants. Surprisingly, the cottonseed oil produced by transgenic lines containing any one of the introduced gene constructs is low in palmitic acid compared to the oil of isogenic non-transformed lines. As exemplified herein, the level of palmitic acid in the seed oil of transformed cotton lines, is reduced to approximately 50% of the level of palmitic acid detected for non-transformed plants. Moreover, the transformed lines containing gene silencing constructs which are targeted against the cotton fatty acid Δ9-desaturase (Δ9 stearoyl-ACP desaturase) genes, and cotton fatty acid Δ12-desaturase (Oleoyl-PC Δ12-desaturase) genes, have high stearic acid, and high oleic acid, respectively, in the cottonseed oil, compared to isogenic non-transformed lines. As exemplified herein, silencing of the cotton fatty acid Δ9-desaturase (Δ9 stearoyl-ACP desaturase) gene has produced cotton plants having as much as 15-fold the stearic acid content of non-transformed lines, with stearic acid accounting for up to approximately 40% of the total lipid of the oil. In elite lines having high oleic acid, this fatty acid accumulated at the expense of linoleic acid, with oleic acid accounting for as much as approximately 80% of total seed lipid.

Intermediate levels of these fatty acids may be obtained by modification of the strength of promoter used to regulate expression of the introduced fatty acid biosynthesis gene, and/or by the selection of specific transgenic lines having desired levels of a particular fatty acid in the oil, and/or by recombination of the phenotypes of particular plants such as by standard sexual hybridisation. Such procedures are well within the ken of a skilled person.

The inventors have further shown that it is possible to combine the high oleic acid and high stearic acid traits, and to obtain intermediate levels of these fatty acids, by conventional plant breeding of elite lines, preferably without compromise of the low palmitic acid characteristic.

Accordingly, a further aspect of the invention provides a cotton plant having increased oleic acid and stearic acid in the seed wherein said plant is produced by sexual hybridisation between a first cotton plant having increased oleic acid in the seed compared to an isogenic non-transformed cotton plant and a second cotton plant having increased stearic acid in the seed compared to an isogenic non-transformed cotton plant, and wherein said first cotton plant and/or said second cotton plant is/are produced in accordance with the inventive method of down-regulating expression of a gene selected from the group consisting of; cotton fatty acid Δ9-desaturase (Δ9 stearoyl-ACP desaturase) genes; and cotton fatty acid Δ12-desaturase (Oleoyl-PC Δ12-desaturase) genes.

In an alternative embodiment, this invention provides a cotton plant having decreased palmitic acid in the seed, wherein said plant is produced by sexual hybridisation between a first cotton plant and a second cotton plant, and wherein said first cotton plant and/or said second cotton plant is/are produced in accordance with the inventive method of down-regulating expression of a gene selected from the group consisting of: cotton fatty acid Δ9-desaturase (Δ9 stearoyl-ACP desaturase) gene and cotton fatty acid Δ12-desaturase (Oleoyl-PC Δ12-desaturase) genes.

A further aspect of the invention provides a transgenic cotton plant produced in accordance with the inventive method and having a fatty acid biosynthesis gene or a gene fragment thereof introduced into its genome, wherein said fatty acid biosynthesis gene is selected from the group consisting of fatty acid Δ9-desaturase (Δ9 stearoyl-ACP desaturase) genes and fatty acid Δ12-desaturase (Oleoyl-PC Δ12-desaturase) genes. This aspect of the invention clearly extends to cotton plants consisting of the progeny of the primary transformant plants which comprise the introduced fatty acid biosynthesis gene or gene fragment. This aspect of the invention further extends to all plant parts, and, in particular, to seed derived from the primary transformed plant or its progeny. Preferably, the seed will comprise the introduced fatty acid biosynthesis gene or gene fragment and, more preferably, such seed will have an oil having a modified fatty acid composition in accordance with the invention (i.e. low palmitic acid and/or high oleic acid and/or high stearic acid and/or low linoleic acid).

This invention clearly extends to any and all of the gene constructs used in the performance of the inventive method as described herein. In particular, this aspect of the invention provides a gene construct comprising the nucleotide sequence of a fatty acid biosynthesis gene, or a gene fragment thereof, placed operably in connection with a promoter sequence that is operable in cotton seed, wherein said gene is selected from the group consisting of fatty acid Δ9-desaturase (Δ9 stearoyl-ACP desaturase) genes, and fatty acid Δ12-desaturase (Oleoyl-PC Δ12-desaturase) genes.

Data provided herein indicate that gene silencing constructs comprising inverted repeats of both coding and noncoding regions of fatty acid desaturase genes can be used to effectively modulate cottonseed oil composition. Additionally, the gene construct may comprise an inverted repeat sequence that is disrupted, such as, for example, by the inclusion of an intron sequence between the inverted repeats, to effectively modulate cottonseed oil composition. Moreover, gene constructs comprising inverted repeats of non-coding sequences, particularly 5'-non-coding sequences, disrupted (i.e. interrupted) by an intervening sequence are particularly useful because they produce an enhanced number of primary transformants having modified fatty acid composition relative to untransformed controls.

Data provided herein show further that the invention can be performed using diverse promoter sequences to regulate expression of the gene silencing construct in cottonseed. The ghFAD2-1 gene promoter and the soybean lectin gene promoter are particularly preferred.

BRIEF DESCRIPTION OF THE DRAWINGS

FIG. 2 is a schematic representation showing the nucleotide and deduced amino acid sequences of the ghSAD-1 cDNA clone encoding the cotton stearoyl-ACP Δ9-desaturase polypeptide (SEQ ID NO: 1) The translation start site ATG is underlined. An asterisk indicates the stop codon. Two iron-binding motifs, separated by about 100 amino acids, are indicated in bold type. The arrow indicates a putative transit peptide cleavage site. The fatty acid desaturase family II signature motif is also underlined.

FIG. 5 is a schematic representation showing the nucleotide and deduced amino acid sequences of the ghFAD2-1 cDNA clone encoding the cotton oleoyl-PC Δ12-desaturase polypeptide (SEQ ID NO: 3). The translation start site (ATG) is in bold type. The priming site for the oligonucleotide Δ12A4, which was used as a PCR primer to amplify the 5' end of the gene, is underlined, and the arrow indicates the 5' to 3' direction of the primer. The asterisk indicates the stop codon.

FIG. 6 is a schematic representation showing the nucleotide and deduced amino acid sequences of the 1422 bp-long ghFAD2-2 cDNA clone encoding the cotton oleoyl-PC Δ12-desaturase polypeptide. The translation start site (ATG) is in bold type. The asterisk indicates a stop codon.

FIG. 7 is a schematic representation of an amino acid sequence alignment between ghFAD2-1 (SEQ ID NO: 4), *Glycine max* microsomal ω-6 desaturase (gmFAD2-2; SEQ ID NO: 31), *A. thaliana* microsomal ω-6 desaturase (atFAD2; SEQ ID NO: 32), *G.max* microsomal ω-6 desaturase (gmFAD2-1; SEQ ID NO: 33), *B. napus* microsomal ω-3 desaturase (bnFAD3; SEQ ID NO: 34), and *G. max* plastid ω-6 desaturase (gmFAD6; SEQ ID NO: 35). Residues indicated in bold type are amino acids that are conserved among all sequences. Shaded areas indicate homologous residues in one or more of the different desaturase sequences. Dots indicate spaces introduced to maximise alignments. Three histidine boxes proposed to be important in iron binding are underlined. Six glycine repeats in relative C-terminus of the ghFAD2-1 polypeptide are also underlined.

FIG. 10 is a schematic representation of the binary vector pBl121, and the soybean lectin gene promoter and terminator of pGLe-10 which were used to produce the pBl-Lectin binary vector.

FIG. 11 is a graphical representation showing the frequency distribution of stearic acid in 15 individual seeds of Coker cotton (upper panel) and 60 individual T2 seeds derived from 4 T1 transgenic cotton plants comprising an inverted repeat of the 5'-end of the ghSAD-1 cDNA clone (lower panel).

FIG. 12 is a graphical representation showing the frequency distribution of oleic acid in 15 individual seeds of Coker cotton (upper panel) and 75 individual T2 seeds derived from 5 T1 transgenic cotton plants comprising an inverted repeat of the 5'-end of the ghFAD2-1 cDNA clone (lower panel).

DETAILED DESCRIPTION OF THE PREFERRED EMBODIMENTS

Figure 1:
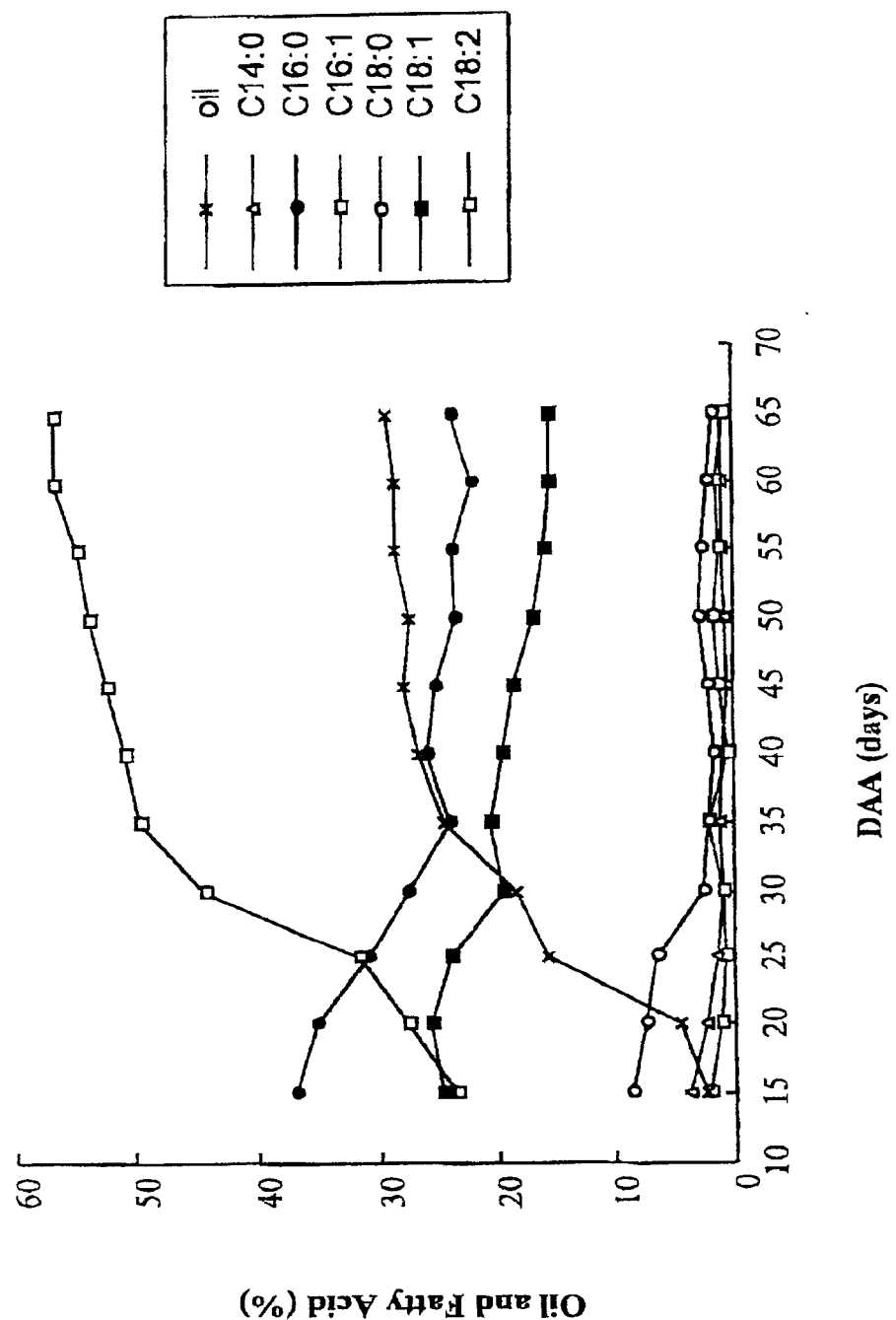
FIG. 1 is a graphical representation showing cotton seed oil content, and fatty acid composition, in developing cotton seed embryos. Samples of cottonseed embryos at 15 to 65 DAA were collected and analysed

One aspect of the invention provides a method of modifying the endogenous oil of a cotton plant comprising producing a transgenic cotton plant having a gene construct which comprises a nucleotide sequence of a fatty acid biosynthesis gene or a gene fragment thereof, wherein said gene or gene fragment is placed operably in connection with a promoter sequence capable of conferring expression of said gene or gene fragment in the seed of a cotton plant, and wherein said fatty acid biosynthesis gene is selected from the group consisting of fatty acid $\Delta$9-desaturase ($\Delta$9 stearoyl-ACP desaturase) genes, and fatty acid $\Delta$12-desaturase (Oleoyl-PC $\Delta$12-desaturase) genes.

For the present purpose, "cotton" is to taken as referring to any plant belonging to the genus *Gossypium* and to any wild relatives, progenitor species, germplasm, cultivar or variety thereof, and to any derivative germplasm, cultivar or variety therefrom.

Without limiting the scope of the present invention, the cotton species to which the inventive method is applicable can be any species selected from the group consisting of: *G. anapoides, G. anomalum, G. arboreum, G. areysianum, G. aridum, G. armourianum, G. australe, G. barbadense, G. barbosanum, G. benadirense, G. hickii, G. briccetti, G. capitis-viridis, G. cosfulatum, G. cunninghamii, G. darwinii, G. davidsonii, G. enthyle, G. exiguum, G. gossypioides, G. harknessli, G. herbaceum, G. hirsutum, G. incanum, G. klotzschianum, G. laxum, G. lobatum, G. londonderriense, G. longicalyx, G. marchantii, G. mustelinum, G. nandewarense, G. nelsonii, G. nobile, G. pilosum, G. populifolium, G. pulchellum, G raimondii, G. robinsonii, G. rotundifolium, G. schwendimantii, G. somalense, G. soudanense, G. stocksii, G. sturtianum, G. thurberi, G. timorense, G. tomentosum, G. trilobum, G. triphyllum,* and *G. viridis.*

Those skilled in the art will be aware that a cotton "variety" is a cotton plant that is contained within a single botanical taxon of the lowest known rank, such as, for example, a plant belonging to a particular species, or a hybrid of two species, wherein said plant expresses one or more stable characteristics that distinguish it from any other group or grouping. By "cultivar" is meant a cultivated variety. In the present context, "germplasm" shall be taken to mean one or more phenotypic characteristics, or one or more genes encoding said one or more phenotypic characteristics, capable of being transmitted between generations.

As the inventive method relates to the modification of cotton oils, it is not necessary for the cotton to be a variety which is commercially successful or of economic utility by virtue of its oil content and/or composition. Conveniently, the cotton upon which the inventive method is applied is a cultivated variety or cultivar or germplasm belonging to a *Gossypium* sp. selected from the group consisting of *G. barbadense, G. hirsutum, G. tomentosum, G. arboreum* and *G. herbaceum,* or a derivative species, germplasm or variety therefrom.

As used herein, the term "progenitor" shall be taken to refer to any of the species, varieties, cultivars, or germplasm, from which a plant is derived. As will be known to those skilled in the art, most commercially useful cotton is a naturally-occurring allotetraploid derived by sexual hybridisation between ancient diploid progenitor parents. Based upon the teaching provided herein, those skilled in the art can readily perform the inventive method on one or more diploid or allotetraploid cottons and produce sexual hybrids between the transgenic plants produced therefrom. The present invention clearly encompasses such alternatives.

As used herein, the term "derivative species, germplasm or variety" shall be taken to mean any plant species, germplasm or variety that is produced using a stated cotton species, variety, cultivar, or germplasm, using standard procedures of sexual hybridisation, recombinant DNA technology, tissue culture, mutagenesis, or a combination of any one or more said procedures. For example, those skilled in the art are aware that there is compatibility between varieties or cultivars within the species *G. barbadense, G. hirsutum*, and *G. tomentosum*, of which *G. barbadense*, and *G. hirsutum* are of particular economic significance. In particular, interspecific hybrids have been produced between *G. barbadense*, and *G. hirsutum*, and between certain diploid species, and the production of such interspecific hybrids is routine to those skilled in the art.

Preferred elite cultivars of cotton include any of the major Australian and United States cultivars, such as, for example, Siokra L22, Siokra L23, Siokra L23i, Siokra V15i, Sicala V2, Sicala V2i, Sicala 33, Sicala 34, Sicot 189i, CSSO, Acala R, Suregrow125, Suregrow501, Suregrow404, Deltapine50, Deltapine51, DES56, DES119, DES24, Delcott277, Auburn 257-202, Stoneville 603, Stoneville 213, PD2164, Frego25, and Arkot 8110, amongst others, or a derivative thereof. Of these cultivars, at least Siokra L22, Siokra L23, Sicala 33, and Sicala 34 normally contain relatively high levels of palmitic acid and linoleic acid, and moderate amounts of mono-unsaturated fatty acids. Accordingly, it is a particularly preferred object of the present invention to reduce the level of palmitic acid, and/or to increase the level of stearic acid and/or oleic acid, in these cultivars.

It is a routine matter for those skilled in the art to produce sexual hybrids between two or more of cotton species, varieties, cultivars, or germplasms, and to subsequently modify the oil composition of said sexual hybrids based upon the teaching provided herein. Accordingly, the inventive method clearly includes the further first step of producing such sexual hybrids.

In accordance with the inventive concept, the transgenic cotton plant has a modified endogenous oil. This means that the total endogenous oil content of the cotton plant, in particular the oil content of the seed, is increased or decreased relative to an isogenic non-transformed plant, or that the composition of said oil is modified relative to an isogenic non-transformed plant, such as, for example, by increasing or decreasing the content of any particular fatty acid in the oil.

Preferably, the relative content of one or more fatty acids in cotton seed oil is increased or decreased, and, more preferably, the content of one or more C16:0 and/or C18:0 fatty acids is modified.

Even more preferably, the inventive method provides the means for modifying (i.e. increasing or decreasing) the content of a fatty acid selected from the group consisting of palmitic acid, oleic acid, linoleic acid, and stearic acid.

In a particularly preferred embodiment of the invention, the inventive method provides the means for modifying the composition of cotton seed oil wherein the modification consists of a modified fatty acid composition selected from the group consisting of:

(i) decreased palmitic acid content of the oil relative to the oil of a non-transformed isogenic cotton plant;

(i) increased stearic acid content of the oil relative to the oil of a non-transformed isogenic cotton plant;

(i) increased oleic acid content of the oil relative to the oil of a non-transformed isogenic cotton plant: and (i) decreased linoleic acid content of the oil relative to the oil of a non-transformed isogenic cotton plant.

The present invention clearly extends to any and all effects on oil content and/or composition which are derived from producing a transgenic cotton plant having one or more fatty acid biosynthesis genes or gene fragments introduced into its genome, and, in particular, to those effects which include a reduction in the level of palmitic acid in the cotton seed oil. As exemplified herein, transgenic cotton having a cotton fatty acid Δ9-desaturase (Δ9 stearoyl-ACP desaturase) gene or gene fragment introduced into its genome produces an oil having decreased palmitic acid and increased stearic acid relative to the oil of a non-transformed isogenic cotton plant, whilst transgenic cotton having a single cotton fatty acid Δ12-desaturase (Oleoyl-PC Δ12-desaturase) gene or gene fragment introduced into its genome produces an oil having decreased palmitic acid, decreased linoleic acid, and increased oleic acid relative to the oil of a non-transformed isogenic cotton plant. Accordingly, the present invention clearly extends to any and all combinations of the modified fatty acid compositions listed hereinabove.

As used herein, the term "relative to a non-transformed isogenic cotton plant", or similar term, shall be taken to mean that a stated integer has a value attributed to it by virtue of a comparison with the value of that integer obtained under similar or identical conditions from a non-transformed cotton plant of the same species as that from which the transgenic cotton plant was derived. Preferably, such a comparison is made by reference to starting plant material from which the transgenic cotton plant was derived or plant material that has the same oil content and composition as said starting plant material.

The oil content of cotton seed, or the content of any fatty acid in the oil of a cotton seed, can be conveniently determined as a proportion of the total lipid of the seed. Procedures for determining the lipid content of cotton seed, and for determining the content and/or composition of fatty acids in cotton seed oil, are well-known to those skilled in the art. For example, the total lipid content of cottonseed or seed oil may be determined using the procedure described by Folsch et al. (1957) or the modification of that procedure described herein. The fatty acid content and/or composition of cotton seed oil may be conveniently determined using gas liquid chromatography against known standard fatty acids, by comparing the fatty acid methyl ester peaks and retention times of the standards with the sample being tested, and by standard integration of the peaks obtained. However, the present invention is not to be limited by the method of determining the content and/or composition of cotton seed oil, in particular the means for determining fatty acid or other lipid components.

In accordance with the inventive concept, a cotton plant as described hereinabove, including any progenitor or derivative species, is modified by the introduction of a fatty acid biosynthesis gene or a fragment thereof, to produce a transgenic plant. It will be apparent from the preceding discussion that, for the purposes of the modification of cotton seed oil in accordance with the inventive concept, the fatty acid biosynthesis gene is selected from the group consisting of fatty acid Δ9-desaturase (Δ9 stearoyl-ACP desaturase) genes and fatty acid Δ12-desaturase (Oleoyl-PC Δ12-desaturase) genes.

For the purposes of nomenclature, the terms "fatty acid Δ9-desaturase" and "Δ9 stearoyl-ACP desaturase" shall be taken to refer to refer to a peptide, polypeptide, protein or enzyme which is capable of producing a carbon double bond at the C-9 position of a saturated C18:0 fatty acid, to form a C18:1-ACP (i.e. oleoyl-ACP) fatty acid.

The terms "fatty acid Δ12-desaturase", and "oleoyl-PC Δ12-desaturase" shall be taken to refer to refer to a peptide, polypeptide, protein or enzyme which is capable of producing a carbon double bond at the C-12 position of a monounsaturated C18:1 fatty acid (i.e. oleoyl-PC), to form a C18:2-PC (i.e. linoleoyl-PC) fatty acid.

Reference herein to a "gene" is to be taken in its broadest context and includes:
(i) a classical genomic gene consisting of transcriptional and/or translational regulatory sequences and/or a coding region and/or non-translated sequences (i.e. introns, 5'- and 3'-untranslated sequences); or
(ii) mRNA or cDNA corresponding to the coding regions (i.e. exons) and 5'- and 3'-untranslated sequences of the gene; or
(iii) amplified single-stranded or double-stranded DNA which is derived from sub-paragraph (i) or sub-paragraph (ii).

The term "gene" is also used to describe synthetic or fusion molecules encoding all or part of a functional product, which may be derived from a naturally-occurring gene, mRNA, or cDNA, by standard recombinant techniques, including any additional nucleotide sequences derived from a homologous or heterologous source which may added to (i) or (ii) or (iii) or said synthetic or fusion molecules.

In the present context, the term "fatty acid biosynthesis gene" or similar term refers to any gene which, in its native context at least, comprises a nucleotide sequence which is capable of encoding a fatty acid Δ9-desaturase (Δ9 stearoyl-ACP desaturase), or fatty acid Δ12-desaturase (Oleoyl-PC Δ12-desaturase) as hereinbefore defined.

In the present context, the term "gene fragment" shall be taken to mean a part of a full-length fatty acid biosynthesis gene as hereinbefore defined, wherein said part is of a suitable length, orientation, and conformation, to be capable of modulating the expression of an endogenous cotton fatty acid biosynthesis gene when introduced into, and preferably expressed in, a cotton oil-producing organ, such as, for example, the seed, including any direct or inverted repeat sequences derived from said gene. Accordingly, the term "part" clearly includes any single fragment of the full-length gene in the sense or antisense orientation, and any inverted repeat sequences having partial or complete self-complementarity, the only requirement being that such parts are capable of modulating the expression of an endogenous fatty acid biosynthesis gene when introduced to cotton. With particular regard to inverted repeat sequences, such sequences will further qualify as parts of the full-length gene whether or not the repeated sequences are contiguous, or alternatively, whether or not the repeated sequences are interrupted by one or more intervening nucleotide sequences, such as, for example, one or more intron sequences. Those skilled in the art will readily be capable of determining whether or not a partial gene or gene fragment is of a suitable length, orientation, and conformation for the purposes of modifying cotton seed oil, without undue experimentation, by empirical means following the teaching provided herein.

For the purposes of further defining the fatty acid biosynthesis gene and gene fragments thereof which are used in performing the inventive method, there are provided herein nucleotide sequences which encode, or are complementary to nucleotide sequences which encode fatty acid biosynthesis enzymes, and gene fragments of said nucleotide sequences and complementary nucleotide sequences, wherein said fatty acid biosynthesis enzymes are selected from the group consisting of fatty acid Δ9-desaturase (Δ9 stearoyl-ACP desaturase) and fatty acid Δ12-desaturase (Oleoyl-PC Δ12-desaturase) enzymes as hereinbefore defined.

Wherein it is desired to increase expression of an endogenous cotton fatty acid biosynthesis gene in order to modify oil composition of the seed, such as, for example, by ectopically-expressing a heterologous or foreign cotton fatty acid biosynthesis gene in cotton seed, the introduced nucleotide sequence is preferably capable of being expressed in cotton at the protein level. Accordingly, in such an embodiment of the invention, it is particularly preferred that the introduced nucleotide sequence will have a codon usage in any protein-encoding part thereof which is suitable for translation in a cotton plant. In those embodiments of the invention wherein it is desired to decrease expression of an endogenous cotton fatty acid biosynthesis gene in order to modify oil composition of the seed, it is preferred that there is sufficient complementarity between the mRNAs encoded by the introduced gene and the endogenous gene so as to hinder, prevent, or reduce the expression of the endogenous gene in the cotton seed, such as, for example, by hybridisation between said mRNAs in the nucleus and/or cytoplasm. As will be apparent to those skilled in the art, any improvements which flow from using introduced fatty acid biosynthesis genes having the codon usage preferences of cotton, and/or high nucleotide sequence identity with an endogenous cotton gene, can be conveniently provided by using nucleotide sequences derived from cotton. However, the present invention is not to be limited by the use of cotton fatty acid biosynthesis genes and gene fragments thereof.

For the purposes of nomenclature, the nucleotide sequence set forth in SEQ ID NO: 1 relates to a cotton fatty acid Δ9-desaturase (Δ9 stearoyl-ACP desaturase) gene, designated ghSAD-1, comprising a 1553 bp cDNA clone obtained by the present inventors, and encoding the fatty acid Δ9-desaturase (Δ9 stearoyl-ACP desaturase) polypeptide set forth herein as SEQ ID NO: 2.

The nucleotide sequence set forth in SEQ ID NO: 3 relates to a first cotton fatty acid Δ12-desaturase (Oleoyl-PC Δ12-desaturase) gene, designated ghFAD2-1, comprising a 1411 bp cDNA clone obtained by the present inventors, and encoding the fatty acid Δ12-desaturase (Oleoyl-PC Δ12-desaturase) polypeptide set forth herein as SEQ ID NO: 4.

The nucleotide sequence set forth in SEQ ID NO: 5 relates to a second cotton fatty acid Δ12-desaturase (Oleoyl-PC Δ12-desaturase) gene, designated ghFAD2-2, comprising a 1422 bp cDNA clone obtained by the present inventors, and encoding the fatty acid Δ12-desaturase (Oleoyl-PC Δ12-desaturase) polypeptide set forth herein as SEQ ID NO: 6.

The nucleotide sequence set forth in SEQ ID NO: 7 relates to the nucleotide sequence of the genomic ghFAD2-1 gene that extends upstream 5006 bp from the translation start site of the gene, but not including said translation start site.

Accordingly, in a particularly preferred embodiment, the present invention encompasses the use of a nucleotide sequence selected from the group consisting of SEQ ID NO: 1, SEQ ID NO: 3, SEQ ID NO: 5 and SEQ ID NO: 7, or any homologous nucleotide sequences, or degenerate nucleotide sequence thereto, or a complementary nucleotide sequence thereto or a gene fragment thereof, to modify oil in cotton.

For the present purpose, "homologues" of a nucleotide sequence shall be taken to refer to an isolated nucleic acid molecule which encodes a polypeptide having the same enzyme activity as that encoded by a stated nucleotide sequence, notwithstanding the occurrence within said homologous sequence, of one or more nucleotide substitutions, insertions, deletions, or rearrangements relative to the stated nucleotide sequence. Accordingly, the present invention clearly extends to the use of homologues of the nucleotide sequences set forth herein, including any homologues of complementary nucleotide sequences and homologues of any degenerate nucleotide sequences thereto. Particularly preferred homologues are those fatty acid biosynthesis genes and gene fragments derived from species other than cotton.

For example, there are numerous examples of nucleotide and amino acid sequences for cloned plant Δ9-desaturase genes lodged in the GenBank database (Table 1), and the sequence similarity between these genes (Shanklin, 1998; Mekhedov et al., 2000) is sufficient to facilitate the isolation of the equivalent homologous genes from other plant species by heterologous probing and/or amplification. To determine putative homologues of cotton Δ9-desaturase genes, a multiple alignment is performed between the derived amino acid sequences encoded by cloned plant Δ9-desaturase genes, such as, for example, the genes listed in Table 1, to identify regions of maximum conservation. Degenerate oligonucleotides are then reverse-engineered based upon the consensus amino acid sequence of one or more of such highly-conserved amino acid sequences. In one approach to isolate cotton homologues, cotton gene libraries (eg seed-specific cDNA or genomic DNA libraries) are probed directly using the oligonucleotides under low stringency hybridisation conditions. Alternatively, the oligonucleotides are used as PCR primers to amplify putative Δ9-desaturase fragments from seed mRNA, or from an equivalent seed-specific cDNA library of cotton. Partial Δ9-desaturase gene fragments obtained in this way are then used as probes to isolate full-length gene sequences from the cDNA library. Alternatively, or in addition, a partial or full-length nucleotide sequence obtained from an already-cloned plant Δ9-desaturase gene can be used to directly probe a cotton gene library. In the case of a multigene family, such as the cotton Δ9-desaturase gene family, the major seed-expressed gene(s) is then determined by analysing the expression pattern of the gene in a range of tissues, including the seed, using RT-PCR, northern hybridisation analysis, nuclear run-on, or nuclear run-off methods, amongst others.

Similar approaches are used to isolate seed-expressed homologues of known cloned plant Δ12-desaturase genes lodged in the GenBank database (Table 2).

By "degenerate nucleotide sequence" is meant a nucleotide sequence having the same protein-encoding capacity as a nucleotide sequence set forth in SEQ ID NO: 1, SEQ ID NO: 3, or SEQ ID NO: 5.

Preferred gene fragments suitable for use in the performance of the inventive method comprise at least about 50 nucleotides derived from the full-length gene sequence, more preferably at least about 100 nucleotides in length, and even more preferably at least about 350 nucleotides in length. In a particularly preferred embodiment, the fatty acid biosynthesis gene used in performing the inventive method comprises the protein-encoding nucleotide sequence of a naturally-occurring fatty acid biosynthesis gene, or a complementary nucleotide sequence thereto Such gene fragments may comprise about 500 to about 850 nucleotides in length, for example, derived from the protein-encoding region of a fatty acid biosynthesis gene.

Additional gene fragments are not excluded, the only requirement being that such gene fragments are capable of being used to successfully modulate the expression of an endogenous cotton fatty acid biosynthesis gene.

TABLE 1

List of microsomal Δ9-desaturase genes and related sequences

| Plant Species | Accession No. | Reference |
|---|---|---|
| Arabidopsis thaliana | X93461 | GenBank X93461 |
| Arachis hypogaea | AF172728 | Tate et al., 1999 |
| Brassica napus | X63364 | Slocombe et al., 1992 |
| Brassica juncea | AF153420 | Vageeshbau et al., 1999 |
| Bressica rapa | X60978 | Knutzon et al., 1992 |
| Elaeis guineensis | U68756 | Shah and Rashid, 1996 |
| Sesamum indicum | D42086 | Yukawa et al., 1994 |
| Carthamus tinctorius | M61109 | Thompson et al., 1991 |
| Coriandrum sativum | M93115 | Cahoon et al., 1992 |
| Cucumis sativa | M59858 | Shanklin et al, 1991 |
| G. hirsutum | AJ132636 | Liu et al. 2000 |
| G. hirsutum | AI730379 | Blewitt et al., 1999 |
| Glycine max | L34346 | Chen and Moon, 1995 |
| Helianthus annuus | U70374 | GenBank U70374 |
| Linum usitatissimum | X90762 | Singh et al., 1994 |
| Linum usitatissimum | AJ006957 | Jain, 1998 |
| Linum usitatissimum | AJ0069578 | Jain, 1998 |
| Asclepias syriaca | U60277 | Cahoon et al, 1997 |
| Olea europaea | U58141 | Baldoni et al., 1996 |
| Pelargonium xhortorum | U40344 | Schultz et al., 1996 |
| Persea americana | AF116861 | Madi and Pruskey, 1999 |
| Oryza sativa | D38953 | Akagi et al., 1995 |
| Ricinus communis | M59857 | Shanklin et al, 1991 |
| Sesamum indicum | D42086 | Yukawa et al., 2000 |
| Solanum commersonii | X78935 | GenBank X78935 |
| Simmondsia chinensis | M83199 | Sato et al., 1992 |
| Spinacia oleracea | X62898 | Nishida et al., 1992 |
| Solanum tuberosum | M91238 | Taylor et al., 1992 |
| T. alata pTAD2 | U07597 | Cahoon et al., 1994 |
| T. alata pTAD3 | U07605 | Cahoon et al., 1994 |
| T. alata Δ6-desaturase | U09269 | Cahoon et al., 1994 |

TABLE 2

List of microsomal Δ12-desaturase genes and related sequences

| Plant species | cDNA or gene | Accession Number | Reference |
|---|---|---|---|
| Arabidopsis thaliana | cDNA | L26296 | Okuley et al., 1994 |
| Arachis hypogaea | cDNA | AF030319 | Jeong et al., 1997 |
| Arachis hypogea | cDNA | AF030319 | Jeong et al., 1994 |
| Borago officinalis | cDNA | AF074324 | Sayenova et al 1998 |
| Brassica carinata | cDNA | AF124360 | Marillia et al., 1999 |
| Brassica juncea | cDNA | X91139 | Singh et al., 1995 |
| Brassica oleracea | cDNA | AF181726 | Fourmann et al 1999 |

TABLE 2-continued

List of microsomal Δ12-desaturase genes and related sequences

| Plant species | cDNA or gene | Accession Number | Reference |
|---|---|---|---|
| Brassica rapa | cDNA | AF042841 | Tanhuanpaa 1999 |
| Crepis alpina | cDNA | Y16285 | Lee et al., 1998 |
| Crepis palaestina | cDNA | CPY16284 | Lee et al., 1998 |
| Glycine max | cDNA | L43920 | Heppard et al., 1996 |
| Glycine max | cDNA | L43921 | Heppard et al., 1996 |
| G. hirsutum | cDNA | X97016 | Liu et al., 1999 |
| G. hirsutum | cDNA | Y10112 | Liu et al., 1999 |
| Helianthus annuus | cDNA | U91341 | Hongtrakul et al 1997 |
| Impatiens balsamina | cDNA | AF182520 | Cahoon et al., 1999 |
| Lactuca sativa | cDNA | AF162199 | Lee et al., 1999 |
| Lesquerella fendleri | cDNA | AF016104 | Broun et al., 1998 |
| Momordica charantia | cDNA | AF182521 | Cahoon et al., 1999 |
| Mucor rouxii | cDNA | AF161219 | Passorn et al., 1999 |
| Petroselinum crispum | cDNA | U86072 | Somssich et al., 1997 |
| Prunus armeniaca | cDNA | AF071892 | Mbeguie-A-Mbeguie |
| Richnus communis | cDNA | U22378 | Van der Loo, 1995 |
| Solanum commersonii | cDNA | X92847 | Grillo, 1995 |
| Vernonia galamensis | cDNA | AF188263 | Hage et al., 1999 |
| Vernonia galamensis | cDNA | AF188264 | Hage et al., 1999 |
| G. arboreum | gene | AJ244914 | Liu et al., 2000 |
| G. australe | gene | AJ244901 | Liu et al., 2000 |
| G. australe | gene | AJ244902 | Liu et al., 2000 |
| G. australe | gene | AJ244903 | Liu et al., 2000 |
| G. barbadense | gene | AJ244918 | Liu et al., 2000 |
| G. barbadense | gene | AJ244919 | Liu et al., 2000 |
| G. bickii | gene | AJ244904 | Liu et al., 2000 |
| G. bickii | gene | AJ244905 | Liu et al., 2000 |
| G. bickii | gene | AJ244906 | Liu et al., 2000 |
| G. costulatum | gene | AJ244889 | Liu et al., 2000 |
| G. cunningharnii | gene | AJ244890 | Liu et al., 2000 |
| G. darwinii (A) | gene | AJ244920 | Liu et al., 2000 |
| G. darwinii (D) | gene | AJ244921 | Liu et al., 2000 |
| G. enthyle | gene | AJ244891 | Liu et al., 2000 |
| G. exiguum | gene | AJ244892 | Liu et al., 2000 |
| G. gossypioides | gene | AJ244912 | Liu et al., 2000 |
| G. herbaceum | gene | AJ244915 | Liu et al., 2000 |
| G. hirsutum (A) | gene | AJ244922 | Liu et al., 2000 |
| G. hirsutum (D) | gene | AJ244923 | Liu et al., 2000 |
| G. klotzschianum | gene | AJ244910 | Liu et al., 2000 |
| G. londonderriense | gene | AJ244893 | Liu et al., 2000 |
| G. marchantii | gene | AJ244894 | Liu et al., 2000 |
| G. mustelinum (A) | gene | AJ244924 | Liu et al., 2000 |
| G. mustelinum(D) | gene | AJ244925 | Liu et al., 2000 |
| G. nelsonii | gene | AJ244907 | Liu et al., 2000 |
| G. nelsonii | gene | AJ244908 | Liu et al., 2000 |
| G. nobile | gene | AJ244895 | Liu et al., 2000 |
| G. pilosum | gene | AJ244896 | Liu et al., 2000 |
| G. populifolium | gene | AJ244897 | Liu et al., 2000 |
| G. pulchellum | gene | AJ244898 | Liu et al., 2000 |
| G. raimondii | gene | AJ244913 | Liu et al., 2000 |
| G. robinsonii | gene | AJ244884 | Liu et al., 2000 |
| G. robinsonii | gene | AJ244885 | Liu et al., 2000 |
| G. rotundifolium | gene | AJ244899 | Liu et al., 2000 |
| G. somalense | gene | AJ244916 | Liu et al., 2000 |
| G. species novum | gene | AJ244900 | Liu et al., 2000 |
| G. stocksii | gene | AJ244917 | Liu et al., 2000 |
| G. sturtianum | gene | AJ244886 | Liu et al., 2000 |
| G. sturtianum | gene | AJ244887 | Liu et al., 2000 |
| G. sturtianum | gene | AJ244888 | Liu et al., 2000 |
| G. tomentosum (A) | gene | AJ244926 | Liu et al., 2000 |
| G. tomentosum (D) | gene | AJ244927 | Liu et al., 2000 |
| G. trilobum | gene | AJ244909 | Liu et al., 2000 |
| G. turneri | gene | AJ244911 | Liu et al., 2000 |

By "expression" is meant transcription and/or translation, with or without subsequent post-translational events which modify the biological activity, cellular or sub-cellular localization, turnover or steady-state level of the peptide, polypeptide, oligopeptide, protein or enzyme molecule.

As used herein, the term "modulate the expression", or similar term, shall be taken to mean that the expression of a stated integer is enhanced, increased or decreased, or that the expression of a stated integer is delayed, inhibited or activated. Such a modulation of expression may be evidenced by direct assay of the integer, such as, for example, by comparison of signals obtained in a northern hybridisation, RT-PCR, or other means to measure steady state levels of mRNA, or alternatively, by comparing protein levels in the cell using ELISA or other immunoassay, SDS/PAGE, or enzyme assay. Alternatively, the modulation of expression may be evidenced by a modificaiton in the phenotype associated with the stated integer, such as, for example, by determining the fatty acid composition of the oil.

In the present context, the term "modulate the expression of an endogenous cotton fatty acid biosynthesis gene" shall be taken to mean that the expression of a fatty acid biosynthesis gene present in a cotton plant is modified, and/or that the enzyme activity of a fatty acid biosynthesis enzyme in cotton is modified, notwithstanding that such an effect may be produced by the ectopic expression of a heterologous (i.e. foreign) or introduced nucleotide sequence in cotton, or by increasing the copy number of cotton fatty acid biosynthesis genes, the only requirement being that such effects are directly or indirectly attributable to the presence of an introduced fatty acid biosynthesis gene or gene fragment thereof.

Those skilled in the art will be aware of whether gene expression has been modified by performance of the invention in cotton, without undue experimentation. For example, the level of expression of a particular gene may be determined by polymerase chain reaction (PCR) following reverse transcription of an mRNA template molecule, essentially as described by McPherson et al. (1991).

Alternatively, the expression level of a genetic sequence may be determined by northern hybridisation analysis or dot-blot hybridisation analysis or in situ hybridisation analysis or similar technique, wherein mRNA is transferred to a membrane support and hybridised to a probe" molecule which comprises a nucleotide sequence complementary to the nucleotide sequence of the mRNA transcript encoded by the gene-of-interest, labelled with a suitable reporter molecule such as a radioactively-labelled dNTP (eg [$\alpha$-$^{32}$P] dCTP or [$\alpha$-$^{35}$S]dCTP) or biotinylated dNTP, amongst others. Expression may then be determined by detecting the appearance of a signal produced by the reporter molecule bound to the hybridised probe molecule. Alternatively, the rate of transcription of a particular gene may be determined by nuclear run-on and/or nuclear run-off experiments, wherein nuclei are isolated from a particular cell or tissue and the rate of incorporation of rNTPs into specific mRNA molecules is determined. Alternatively, expression of a particular gene may be determined by RNase protection assay, wherein a labelled RNA probe or riboprobe" which is complementary to the nucleotide sequence of mRNA encoded by said gene is annealed to said mRNA for a time and under conditions sufficient for a double stranded mRNA molecule to form, after which time the sample is subjected to digestion by RNase to remove single-stranded RNA molecules and in particular, to remove excess unhybridised riboprobe. Such approaches are described in detail by Sambrook et al. (1989) and Ausubel (1987). Those skilled in the art will also be aware of various immunological and enzymatic methods for detecting the level of expression of a particular gene at the protein level, for example using rocket immunoelectrophoresis, ELISA, radioimmunoassay and western blot immunoelectrophoresis techniques, amongst others.

Preferably, the fatty acid biosynthesis gene or gene fragment is in a format suitable for the ectopic expression of a fatty acid biosynthesis polypeptide in cotton, or alternatively, for the silencing or down-regulation of expression of an endogenous fatty acid biosynthesis gene in cotton.

As will be known to those skilled in the art, to ectopically express a polypeptide, the structural gene region which encodes said polypeptide is placed in the sense orientation in operable connection with a suitable promoter sequence so as to provide for transcription and translation in the cell. In the present context, as such ectopic expression is intended to lead to an increase in the activity of a fatty acid biosynthesis polypeptide, it is essential for the structural gene region to encode a polypeptide having enzymatic activity in cotton seed. Accordingly, the present invention encompasses the use of the nucleotide sequences set forth herein or any fragments thereof which encode functional enzymes, and any degenerate nucleotide sequences thereto, or homologous gene sequences derived from other species.

Whilst not being bound by any theory or mode of action, means for silencing or otherwise reducing the expression of an endogenous fatty acid biosynthesis gene in cotton include means which target transcription and/or mRNA stability and/or mRNA turnover and/or accessibility of mRNA to ribosomes or polysomes. Such means include sense suppression, cosuppression, antisense suppression, ribozyme-mediated gene silencing, and post-transcriptional gene silencing (PTGS). As with the ectopic expression of genes, it is preferred to introduce the nucleic acid in operable connection with a promoter sequence for the purposes of silencing or otherwise reducing the expression of an endogenous fatty acid biosynthesis gene in cotton.

Sense suppression and cosuppression of gene expression utilise nucleotide sequences which are positioned in the sense orientation in an expressible format (i.e. "sense molecules") As used herein, the term "sense molecule" shall be taken to refer to an isolated nucleic acid molecule which encodes or is complementary to an isolated nucleic acid molecule which is capable of encoding a fatty acid biosynthesis polypeptide, including full-length polypeptides having enzyme activity and fragments thereof lacking enzyme activity, wherein said nucleic acid molecule is provided in a format suitable for expression when introduced into a cotton plant by transfection or transformation.

As used herein, the term "co-suppression" shall be taken to mean a reduction in expression of an endogenous cotton fatty acid biosynthesis gene that occurs when one or more copies of said gene, or one or more copies of a substantially similar gene are introduced into the cell. The present invention clearly extends to the use of co-suppression to inhibit the expression of an endogenous fatty acid biosynthesis gene in cotton.

In "sense suppression", expression of the endogenous fatty acid biosynthesis gene is decreased by virtue of expressing in the cell a dominant-negative sense molecule. For example, a sense molecule, which encodes an enzymatically-inactive fatty acid biosynthesis polypeptide, may be expressed in the seed. Alternatively, a sense molecule which encodes a partial or full-length mRNA species may be introduced to the cotton genome such that transgene insertion events lead to a reduction in expression of both the endogenous gene and the transgene. Preferred dominant-negative sense molecules will comprise at least one or more functional protein domains of the wild-type protein, such as, for example, a domain which is involved in dimerisation with other polypeptide subunits of a functional holoenzyme.

In the context of the present invention, the term "antisense suppression" shall be taken to mean a suppression of gene expression which is mediated by expressing an antisense molecule in the cotton plant. An "antisense molecule" is an RNA molecule which is produced by transcription of the DNA strand which is complementary to that which is normally transcribed to produce a "sense" mRNA molecule capable of being translated into a fatty acid biosynthesis polypeptide. The antisense molecule is therefore complementary to the sense mRNA, or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a functional fatty acid biosynthesis polypeptide.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852. The present invention extends to ribozymes which target a sense mRNA encoding an endogenous cotton fatty acid biosynthesis polypeptide, such that it is no longer capable of being translated to synthesise a functional polypeptide product.

In the context of the present invention, post-transcriptional gene silencing (PTGS) is a reduction in gene expression which is produced by introducing nucleic acid to the cell which comprises a first nucleotide sequence capable of being transcribed into sense mRNA, linked in head-to-head or tail-to-tail configuration, with or without any intervening nucleotide sequences, to a second nucleotide sequence capable of being transcribed into antisense mRNA such that the complete mRNA molecule which is transcribed from said nucleic acid comprises an inverted repeat sequence having self-complementarity. Whilst not being bound by any theory or mode of action, the transcript has the potential to form a secondary structure, such as, for example, a hairpin loop, in the nucleus and/or cytosol of a cell, and to sequester sense mRNA which is transcribed therein, such that single-stranded regions of the sequestered mRNA are rapidly degraded and/or a translationally-inactive complex is formed. The nucleotide sequences comprising the inverted repeat may include the full-length sequence of the target gene, or a gene fragment thereof, including both coding and/or untranslated nucleotide sequences.

As exemplified herein, highly-efficient PTGS may be performed using gene fragments of about 90 nucleotides in length, or longer, derived from the 5'-coding or non-coding end of the target gene, linked in head-to-head or tail-to-tail configuration. However, the present invention clearly encompasses the use of inverted repeat sequences derived from fragments of less than 90 nucleotides in length, and derived from regions other than the 5'-end of the target gene. In particular, the present invention contemplates the use of gene fragments of only about 25 nucleotides in length or longer, derived from the 5'-end or 3'-end of the target nucleotide sequence, such as, for example, 25 bp derived from the 5'-UTR or 3'-UTR of the ghSAD-1 or ghFAD2-1 cDNA. As will be apparent to the skilled person, sequences longer than 90 nucleotides in length are also useful in performing the invention.

Moreover, the present invention clearly extends to the use of inverted repeats which are either contiguous inverted repeats of gene fragments, or alternatively, wherein each gene fragment comprising the inverted repeat is separated, or interrupted, by the insertion of one or more intervening nucleotide sequences. The use of intron sequences to space or interrupt each of the gene fragments comprising the inverted repeat is particularly encompassed by the invention. The intron sequence which is used in this embodiment may be any intron sequence, and preferably, albeit not necessarily, a plant intron sequence. As exemplified herein, the inventors have utilized an inverted repeat of about 90 nucleotides from the 5'-untranslated region of the endogenous ghFAD2-1 gene wherein the repeat is disrupted by the complete intron-1 sequence of the gene.

The present invention clearly extends to the use of other gene fragments in performing the inventive method than those specifically exemplified herein. Preferred gene fragments for use in antisense and/or PTGS approaches will comprise a nucleotide sequence consisting of at least about 10 to 20 nucleotides of the target fatty acid biosynthesis gene, more preferably at least about 50–100 nucleotides, or a full-length or substantially full-length mRNA transcript encoded by said target gene.

It is understood in the art that certain modifications, including nucleotide substitutions, may be made to the genes and gene fragments used in performing the inventive method, without destroying the efficacy of said molecules in modulating the expression of an endogenous fatty acid biosynthesis gene. It is therefore within the scope of the present invention to include any nucleotide sequence variants, homologues, or analogues of the said genes and gene fragments. The genes and gene fragments having utility in the inventive method will preferably comprise a nucleotide sequence having at least about 60–70% identity, more preferably at least about 70–80% identity, still more preferably at least about 80–90% identity or at least about 95–99% identity to the nucleotide sequence of a fatty acid biosynthesis gene which is set forth in any one or more of SEQ ID NOs: 1, 3, or 5 or 7, or a gene fragment thereof, or a complementary nucleotide sequence thereto.

Reference herein to a percentage identity or percentage similarity between two or more nucleotide or amino acid sequences shall be taken to refer to the number of identical or similar residues in a nucleotide or amino acid sequence alignment, as determined using any standard algorithm known by those skilled in the art. In particular, nucleotide and/or amino acid sequence identities and similarities may be calculated using the GAP program, which utilises the algorithm of Needleman and Wunsch (1970) to maximise the number of residue matches and minimise the number of sequence gaps. The GAP program is part of the Sequence and Analysis Software Package of the Computer Genetics Group Inc., University Research Park, Madison, Wis., United States of America (Devereux et al., 1984). In nucleotide and amino acid sequence comparisons which contain no gaps, the percentage identity may be calculated from a direct comparison of the number of identical nucleotides or amino acids there between, as the case may be, expressed as a percentage of the total number of nucleotides or amino acids in the sequences.

In an alternative embodiment, the genes and gene fragments used in performing the inventive method will preferably comprise a nucleotide sequence which is capable of hybridizing under at least low stringency conditions, more preferably under at least moderate stringency conditions and even more preferably under at least high stringency conditions, to any one or more of SEQ ID NOs: 1, 3, 5 or 7, or a gene fragment thereof, or a complementary nucleotide sequence thereto.

For the purposes of defining the level of stringency, those skilled in the art will be aware that several different hybridisation conditions may be employed For example, a low stringency may comprise a hybridisation and/or a wash carried out in 6×SSC buffer, 0.1% (w/v) SDS at 28° C. or room temperature. A moderate stringency may comprise a hybridisation and/or wash carried out in 2×SSC buffer, 0.1% (w/v) SDS at a temperature in the range 45° C. to 65° C. A high stringency may comprise a hybridisation and/or wash carried out in 0.1×SSC buffer, 0.1% (w/v) SDS or Church Buffer at a temperature of at least 65° C. Variations of these conditions will be known to those skilled in the art.

Generally, the stringency is increased by reducing the concentration of SSC buffer, and/or increasing the concentration of SDS in the hybridisation buffer or wash buffer and/or increasing the temperature at which the hybridisation and/or wash are performed. Conditions for hybridisations and washes are well understood by one normally skilled in the art. For the purposes of clarification of parameters affecting hybridisation between nucleic acid molecules, reference can conveniently be made to pages 2.10.8 to 2.10.16, of Ausubel et al. (1987), which is herein incorporated by reference.

The introduction of a fatty acid biosynthesis gene, or a gene fragment thereof, into cotton and expression may be facilitated by providing said gene or gene fragment in operable connection with a suitable promoter sequence, in the form of a gene construct or vector molecule. Accordingly, the present invention clearly extends to the use of gene constructs and vectors designed to facilitate the introduction and/or expression of the introduced genes and gene fragments in cotton, and particularly, in cotton seed.

In the present context, the term "gene construct" refers to any nucleic acid molecule that comprises one or more foreign nucleic acid molecules comprising the nucleotide sequence of the fatty acid biosynthesis gene and/or a fragment thereof, in a form suitable for introducing into a plant cell, tissue, organ, or plant part, including a plantlet, and preferably which is capable of being integrated into the genome of a plant.

As used herein, the word "vector" shall be taken to refer to a linear or circular DNA sequence which includes a gene construct as hereinbefore defined, and which includes any additional nucleotide sequences to facilitate replication in a host cell and/or integration and/or maintenance of said gene construct or a part thereof in the host cell genome.

Preferred vectors include plasmids, cosmids, plant viral vectors, and the like, such as, for example, a plasmid or cosmid containing T-DNA to facilitate the integration of the foreign nucleic acid into the plant genome, such as, for example, binary transformation vectors, super-binary transformation vectors, co-integrate transformation vectors, Ri-derived transformation vectors, suitable for use in any known method of transforming cotton.

The term "vector" shall also be taken to include any recombinant virus particle or cell, in particular a bacterial cell or plant cell, which comprises the gene construct of the invention. For example, a plant virus, such as a gemini virus, amongst others, may be engineered to contain the fatty acid biosynthesis gene or gene fragment thereof, or alternatively, a gene construct containing the fatty acid biosynthesis gene or gene fragment may be introduced into *Agrobacterium tumefaciens* or *Agrobacterium rhizogenes*, for subsequent transfer to cotton as described hereinabove.

In a particularly preferred embodiment, the gene construct contains the fatty acid biosynthesis gene or gene fragment thereof cloned within a binary transformation vector, such as, for example, the binary transformation vector pBI121 which is well-known to those skilled in the art to be suitable for *Agrobacterium*-mediated transformation by virtue of the presence of the T-DNA left and right border sequences, and the NPTII structural gene placed operably in connection with the nopaline synthase promoter sequence which confers resistance on plant cells carrying the plasmid to the antibiotic kanamycin.

Reference herein to a "promoter" is to be taken in its broadest context and includes the transcriptional regulatory sequences of a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner, the only requirement being that said promoter sequence is capable of conferring expression on a fatty acid biosynthesis gene or gene fragment as described herein, in a cotton plant, and more particularly, in cotton seed.

In the present context, the term "promoter" is also used to describe a synthetic or fusion molecule, or derivative which confers, activates or enhances expression of said sense molecule in cotton. Preferred promoters may contain additional copies of one or more specific regulatory elements, to further enhance expression and/or to alter the spatial expression and/or temporal expression of a nucleic acid molecule to which it is operably connected.

Placing a nucleic acid molecule under the regulatory control of a promoter sequence means positioning said molecule such that expression is controlled by the promoter sequence. A promoter is usually, but not necessarily, positioned upstream or 5' of a nucleic acid molecule which it regulates. Furthermore, the regulatory elements comprising a promoter are usually positioned within 2 kb of the start site of transcription of the gene or gene fragment the expression of which it regulates. In the construction of heterologous promoter/structural gene combinations, it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Promoters suitable for use in genetic constructs of the present invention include promoters derived from the genes of viruses, yeasts, moulds, bacteria, insects, birds, mammals and plants which are capable of functioning in cotton. The promoter may confer expression constitutively throughout the plant, or differentially with respect to the cotton seed, or differentially with respect to the developmental stage of the seed at which expression occurs, or in response to external stimuli such as physiological stresses, pathogens, or metal ions, amongst others.

Exemplary promoters suitable for use in the inventive method are listed in Table 3. The promoters listed in Table 3 are provided for the purposes of exemplification only and the present invention is not to be limited by the list provided therein. Those skilled in the art will readily be in a position to provide additional promoters that are useful in performing the present invention, and, in particular, the promoter of any fatty acid biosynthesis gene of a plant, and preferably a dicotyledonous plant. The present invention particularly contemplates the use of promoters derived from genes encoding fatty acid desaturases; fatty acid hydroxylases; fatty acid epoxygenases; fatty acid acetylenases, fatty acid conjugases; acyl carrier protein (ACP); acyl-ACP thioesterases; acyl transferases, acyl elongases; and fatty acid keto-acyl synthases. In a particularly preferred embodiment, the promoter sequence is the promoter region of the soybean lectin gene (Vodkin et al., 1983: Cho et al., 1995: GenBank Accession No. K00821) or the promoter of the cotton Δ12 desaturase gene (i.e. ghFAD2-1 gene promoter) set forth in SEQ ID NO: 7, or a fragment of said promoter that is operable in cottonseed.

In addition to the fatty acid biosynthesis gene or gene fragment, and the promoter sequence, the gene constructs used in performing the inventive method will generally comprise a terminator sequence. The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the nopaline synthase (NOS) gene terminator of *Agrobacterium tumefaciens*, the terminator of the Cauliflower mosaic virus (CaMV) 35S gene, the soybean lectin gene terminator, the Rubisco small subunit (SSU) gene terminator sequences and subclover stunt virus (SCSV) gene sequence terminators, amongst others. In a particularly preferred embodiment of the invention, the fatty acid biosynthesis gene or gene fragment thereof is placed upstream of the soybean lectin gene terminator. Those skilled in the art will be aware of additional terminator sequences which may readily be used without any undue experimentation.

TABLE 3

EXEMPLARY PROMOTERS FOR USE IN THE PERFORMANCE OF THE PRESENT INVENTION

| GENE SOURCE | EXPRESSION PATTERN | REFERENCE |
| --- | --- | --- |
| I: CELL-SPECIFIC, TISSUE-SPECIFIC, AND ORGAN-SPECIFIC PROMOTERS | | |
| seed-specific genes | seed | Simon et al,, 1985; Scofield et al., 1987; Baszczynski et al., 1990. |
| Brazil Nut albumin | seed | Pearson et al., 1992. |
| legumin | seed | Ellis et al., 1988. |
| glutelin (rice) | seed | Takaiwa et al., 1986; Takaiwa et al., 1987. |
| zein | seed | Malzke et al, 1990 |
| napA | seed | Slalberg et al, 1996. |
| wheat LMW and HMW glutenin-1 | endosperm | Mol Gen Genet 216:81–90, 1989; NAR 17:461–2, 1989 |
| wheat SPA | seed | Albani et al, 1997 |
| wheat α, β, γ-gliadins | endosperm | EMBO 3:1409–15, 1984 |
| barley Itr1 promoter | endosperm | |
| barley B1, C, D, hordein | endosperm | Theor Appl Gen 98:1253–62, 1999; Plant J 4:343–55, 1993; Mol Gen Genet 250:750–60, 1996 |
| barley DOP | endosperm | Mena et al, 1998 |
| blz2 | endosperm | EP99106056.7 |
| synthetic promoter | endosperm | Vicente-Carbajosa et al, 1998. |
| rice prolamin NRP33 | endosperm | Wu et al, 1998 |
| rice α-globulin Glb-1 | endosperm | Wu et al, 1998 |
| rice OSH1 | embryo | Sato et al, 1996 |
| rice α-globulin REB/OHP-1 | endosperm | Nakase et al., 1997 |
| rice ADP-glucose PP | endosperm | Trans Res 6:157–68, 1997 |
| maize ESR gene family | endosperm | Plant J 12:235–46, 1997 |
| sorghum γ-kafirin | endosperm | PMB 32:1029–35, 1996 |
| KNOX | embryo | Postma-Haarsma et al, 1999 |
| rice oleosin | embryo and aleurone | Wu et al, 1998 |
| sunflower oleosin | seed (embryo and dry seed) | Cummins et al., 1992 |
| soybean lectin | seed | Vodkin et al., 1983; Cho et al., 1995; GenBank Accession No. K00821 |
| oleate Δ12-hydroxylase:desaturase | seed | Broun et al., 1998 |
| linseed promoters | seed | Jain et al., 1999 |
| palmiloyl-ACP thioesterase | cotton seed | Yoder et al., 1999 |
| II: EXEMPLARY CONSTITUTIVE PROMOTERS | | |
| Actin | constitutive | McElroy et al, 1990 |
| CaMV 35S | constitutive | Odell et al, 1985 |
| CaMV 19S | constitutive | Nilsson et al., 1997 |
| GOS2 | constitutive | de Pater et al, 1992 |
| ubiquitin | constitutive | Christensen et al, 1992 |
| rice cyclophilin | constitutive | Buchholz et al, 1994 |
| maize H3 histone | constitutive | Lepetit et al, 1992 |
| actin 2 | constitutive | An et al, 1996 |

The gene constructs of the invention may further include an origin of replication sequence required for replication in a specific cell type, for example a bacterial cell, when said gene construct is required to be maintained as an episomal genetic element (eg. plasmid or cosmid molecule) in said cell.

Preferred origins of replication include, but are not limited to, the f1-ori and co/E1 origins of replication.

The gene construct may further comprise a selectable marker gene or genes that are functional in a cell into which said gene construct is introduced.

As used herein, the term "selectable marker gene" includes any gene which confers a phenotype on a cell in which it is expressed to facilitate the identification and/or selection of cells which are transfected or transformed with a gene construct of the invention or a derivative thereof.

Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

To facilitate the *Agrobacterium*-mediated introduction of the fatty acid biosynthesis gene or gene fragment into cotton, it is particularly preferred for the introduced gene sequences including any promoter and terminator sequences, and with or without any selectable marker gene sequences or prokaryotic origins of replication, to be flanked by one or more T-DNA sequences. Preferred T-DNA sequences include one or more left and/or right border sequences derived from the *Agrobacterium tumefaciens* Ti plasmid.

The gene constructs are introduced into a cotton cell using standard procedures, and the transfected or transformed cell is subsequently regenerated to produce a transgenic cotton plant. By "transgenic plant" is meant a plant having foreign DNA introduced thereto by means of transfection or transformation. In the present context, the term "transgenic plant" shall be taken to include a cell, tissue or organ which is derived from a transgenic plant, and/or a cell, tissue or organ which capable of clonal propagation to produce a transgenic plant.

By "transfection" is meant that the process of introducing a gene construct or vector or an active fragment thereof which comprises foreign nucleic acid into a cell, tissue or organ derived from a plant, without integration into the cell's genome.

By "transformation" is meant the process of introducing a gene construct or vector or an active fragment thereof which comprises foreign nucleic acid into a cell, tissue or organ derived from a plant, wherein said foreign nucleic acid is stably integrated into the genome.

In the present context, "foreign nucleic acid" means any nucleic acid that is not present in the genome of the cell, tissue, or organ into which the gene construct or vector is introduced, and, in particular nucleic acid comprising the nucleotide sequence of a fatty acid biosynthesis gene or a fragment thereof in a format suitable for modifying the oil of cotton in accordance with the inventive method.

Means for introducing recombinant DNA into cotton tissue or cells will be known to those skilled in the art, and include, but are not limited to, direct DNA uptake into protoplasts (Krens et al., 1982; Paszkowski et al., 1984), PEG-mediated uptake to protoplasts (Armstrong et al. 1990), microparticle bombardment, electroporation (Fromm et al., 1985), microinjection of DNA (Crossway et al. 1986), microparticle bombardment of tissue explants or cells (Christou et al., 1988; Sanford, 1988), vacuum-infiltration of tissue with nucleic acid, T-DNA-mediated transfer of *Agrobacterium* to the plant tissue as described essentially by An et. al. (1985), Herrera-Estrella et al. (1983a, 1983b, 1985), or by Cousins et al. (1991).

For microparticle bombardment of cells, a microparticle is propelled into a cell to produce a transformed plant cell, tissue or organ. Any suitable ballistic cell transformation methodology and apparatus can be used in performing the present invention. Exemplary apparatus and procedures are disclosed by Stomp et al., (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole cotton plant may be regenerated from the transformed or transfected cell, in accordance with procedures well known in the art. Plant tissue capable of subsequent clonal propagation, whether by organogenesis or embryogenesis, may be transformed and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (eg., apical meristem, axillary buds, and root meristems), and induced meristem tissue (eg., cotyledon meristem and hypocotyl meristem).

The term "organogenesis", as used herein, means a process by which shoots and roots are developed sequentially from meristematic centres.

The term "embryogenesis", as used herein, means a process by which shoots and roots develop together in a concerted fashion (not sequentially), whether from somatic cells or gametes.

A particularly preferred method of producing a transgenic cotton plant is by *Agrobacterium*-mediated transformation of cotyledons, followed by the induction of callus formation, and the subsequent induction of embryogenic callus, and regeneration into plants, essentially as exemplified herein.

The regenerated transformed cotton plants described herein may take a variety of forms, such as, for example, chimeras of transformed cells and non-transformed cells; or clonal transformants (eg., all cells transformed to contain the expression cassette). They may be propagated by a variety of means, such as by clonal propagation or classical breeding techniques, For example, a first generation (or T1) transformed plant may be selfed to give homozygous second generation (or T2) transformant, and the T2 plants further propagated through classical breeding techniques.

Preferably, the introduced fatty acid biosynthesis gene or gene fragment is capable of being expressed in the cotton seed so as to modify (i.e. increase or decrease) the level of expression of an endogenous cotton fatty acid biosynthesis gene to a level that is sufficient to modify the content and/or composition of the oil produced in said seed.

The activity of a fatty acid biosynthesis enzyme in cotton seed oil may be determined using procedures known to those skilled in the art. For example, the enzyme activity may be calculated by direct enzyme assay, or alternatively, by indirect means involving the determination of substrate and product levels, such as, for example, by an appropriate algorithm which calculates the proportion of the fatty acid product of the enzyme as a proportion of the combined content of all such fatty acid products and remaining fatty acid substrate.

In a preferred embodiment, the activity of the fatty acid Δ12-desaturase (Oleoyl-PC Δ12-desaturase) enzyme in cotton seed oil is determined using the Oleic Desaturation Proportion (ODP) algorithm, which determines the proportion of unsaturated polyunsaturated C18 fatty acids relative to the total unsaturated C18 fatty acids in cotton seed oil, as follows:

$$ODP=(C18:2+C18:3)/(C18:1+C18:2+C18:3).$$

The ODP measures the proportion of total unsaturated C18 fatty acid that is desaturated by the fatty acid Δ12-desaturase (Oleoyi-PC Δ12-desaturase) enzyme.

Alternatively or in addition, the activity of the fatty acid Δ9-desaturase (Δ9 stearoyl-ACP desaturase) enzyme in cotton seed oil is determined using the Stearic Desaturation Proportion (SDP) algorithm, which determines the proportion of unsaturated C18 fatty acids relative to the total C18 fatty acids in cotton seed oil, as follows:

$$SDP=(C18:1+C18:2+C18:3)/(C18:0+C18:1+C18:2+C18:3).$$

The SDP measures the proportion of total C18 fatty acid that is desaturated by the fatty acid Δ9-desaturase (Δ9 stearoyl-ACP desaturase) enzyme.

It will be apparent from the preceding discussion that there are several steps involved in producing a transgenic plant, including production of gene constructs, transformation of a cotton cell with the gene constructs, the production of embryogenic callus from the transformed cotton cells, selection of transformed cells, regeneration into whole plants, and propagation of the transgenic plants by asexual or sexual means. The present invention clearly encompasses any and all of these steps collectively or individually, by the term "producing a transgenic cotton plant".

The inventive method described herein may further include the sexual hybridisation of the transgenic plant produced as described with any other transgenic or non-transgenic cotton species, variety, cultivar or germplasm, such as, for example, for the purpose of combining the desirable characteristics of both parents in the progeny of that sexual hybridisation. The present invention encompasses the use of the primary transgenic cotton plant, or the progeny thereof produced by self-fertilisation or out-crossing, as both a pollen parent or a seed parent.

Accordingly, the present invention clearly extends to a method of modifying the endogenous oil of a cotton plant comprising:

(i) producing a transgenic cotton plant having a gene construct which comprises a nucleotide sequence of a fatty acid biosynthesis gene or a gene fragment thereof, wherein said gene or gene fragment is placed operably in connection with a promoter sequence capable of conferring expression of said gene or gene fragment in the seed of a cotton plant, and wherein said fatty acid biosynthesis gene is selected from the group consisting of fatty acid Δ9-desaturase (Δ9 stearoyl-ACP desaturase) genes and fatty acid Δ12-desaturase (Oleoyl-PC Δ12-desaturase) genes; and (ii) sexually hybridising said transgenic cotton plant with a second cotton plant to produce a progeny plant.

In accordance with this embodiment of the invention, the second cotton plant may be a transgenic cotton plant which produces a high level of stearic acid in the seed, by virtue of the presence and/or expression of one or more introduced fatty acid biosynthesis genes or gene fragments, such as, for example, an introduced fatty acid Δ9-desaturase (Δ9 stearoyl-ACP desaturase) gene or gene fragment in the antisense orientation, or alternatively, an inverted repeat of a fatty acid Δ9-desaturase (Δ9 stearoyl-ACP desaturase) gene or gene fragment which is capable of self-complementarity.

In an alternative embodiment, the second cotton plant is a transgenic cotton plant which produces a high level of oleic acid in the seed, by virtue of the presence and/or expression of one or more introduced fatty acid biosynthesis genes or gene fragments, such as, for example, an introduced fatty acid Δ12-desaturase (Oleoyl-PC Δ12-desaturase) gene or gene fragment in the antisense orientation, or alternatively, an inverted repeat of a fatty acid Δ12-desaturase (Oleoyl-PC Δ12-desaturase) gene or gene fragment which is capable of self-complementarity.

In a still further embodiment, the second cotton plant is a transgenic cotton plant which produces a low level of palmitic acid in the seed, by virtue of the presence and/or expression of one or more introduced fatty acid biosynthesis genes or gene fragments thereof, such as, for example:

(i) an introduced fatty acid Δ9-desaturase (Δ9 stearoyl-ACP desaturase) gene or gene fragment in the antisense orientation; or alternatively, (ii) an introduced fatty acid Δ12-desaturase (Oleoyl-PC ,12-desaturase) gene or gene fragment in the antisense orientation: or alternatively, (iii) an inverted repeat of a fatty acid Δ9-desaturase (Δ9 stearoyl-ACP desaturase) gene or gene fragment which is capable of self-complementarity; or alternatively, (iv) an inverted repeat of a fatty acid Δ12-desaturase (Oleoyl-PC Δ12-desaturase) gene or gene fragment which is capable of self-complementarity.

In a particularly preferred embodiment of the invention, sexual hybridisation is performed between a first cotton plant having increased oleic acid in the seed compared to an isogenic non-transformed cotton plant and a second cotton plant having increased stearic acid in the seed compared to an isogenic non-transformed cotton plant. Preferably, the progeny of such a crossing produces a seed oil which is high in oleic acid and stearic acid compared to an isogenic non-transformed cotton plant.

In an alternative embodiment, sexual hybridisation is performed between a first cotton plant having increased stearic acid in the seed compared to an isogenic non-transformed cotton plant and a second cotton plant having decreased palmitic acid in the seed compared to an isogenic non-transformed cotton plant. Preferably, the progeny of such a crossing produces a seed oil which is high in stearic acid and low in palmitic acid compared to an isogenic non-transformed cotton plant.

In a further alternative embodiment, sexual hybridisation is performed between a first cotton plant having increased oleic acid in the seed compared to an isogenic non-transformed cotton plant and a second cotton plant having decreased palmitic acid in the seed compared to an isogenic non-transformed cotton plant. Preferably, the progeny of such a crossing produces a seed oil which is high in oleic acid and low in palmitic acid compared to an isogenic non-transformed cotton plant.

In yet a further alternative embodiment, sexual hybridisation is performed between a first cotton plant having increased oleic acid and low palmitic acid in the seed compared to an isogenic non-transformed cotton plant and a second cotton plant having increased oleic acid and decreased palmitic acid in the seed compared to an isogenic non-transformed cotton plant. Preferably, the progeny of such a crossing produces a seed oil which is high in oleic acid and stearic acid, and low in palmitic acid, compared to an isogenic non-transformed cotton plant.

In yet a further alternative embodiment, sexual hybridisation is performed between a first cotton plant having decreased linoleic acid in the seed compared to an isogenic non-transformed cotton plant, and a second cotton plant having increased stearic acid in the seed compared to an isogenic non-transformed cotton plant. Preferably, the progeny of such a crossing produces a seed oil which is high in stearic acid and low in linoleic acid, compared to an isogenic non-transformed cotton plant. More preferably, the progeny is also low in palmitic acid and/or high in oleic acid, compared to an isogenic non-transformed cotton plant.

The present invention clearly extends to all such alternatives. Other sexual hybridisations are not excluded.

The present invention clearly contemplates a sexual hybridisation between the transgenic cotton plant produced in accordance with the inventive method, and a naturally occurring cotton species, variety, cultivar, or germplasm which exhibits desirable oil-producing attributes, the only requirement being that said naturally occurring plant is compatible with the transgenic plant. For example, *G. arboreum* contains high levels of oleic acid in the seed, and reduced linoleic acid, of which both characteristics are desirable attributes.

The inventive method described herein further contemplates the genetic modification of a primary transgenic cotton plant or the progeny thereof to further modify the cotton seed oil. As with the use of sexual hybridisation, additional genetic modification may be used to introduce additional oil-modifying characteristics to the cotton plant, to further enhance its oil quality compared to the primary transgenic plant. In a particularly preferred embodiment, the present invention contemplates a method of modifying the endogenous oil of a cotton plant comprising:

(i) producing a first transgenic cotton plant having a gene construct which comprises a nucleotide sequence of a first fatty acid biosynthesis gene or a gene fragment thereof, wherein said gene or gene fragment is placed operably in connection with a promoter sequence capable of conferring expression of said gene or gene fragment in the seed of a cotton plant, and wherein said first fatty acid biosynthesis gene is selected from the group consisting of fatty acid $\Delta$9-desaturase ($\Delta$9 stearoyl-ACP desaturase) genes and fatty acid $\Delta$12-desaturase (Oleoyl-PC $\Delta$12-desaturase) genes;

(ii) sexually hybridising said first transgenic cotton plant with a cotton plant to produce a progeny plant; and (iii) producing a second transgenic cotton plant having a gene construct which comprises a nucleotide sequence of a second fatty acid biosynthesis gene or a gene fragment thereof, wherein said gene or gene fragment is placed operably in connection with a promoter sequence capable of conferring expression of said gene or gene fragment in the seed of a cotton plant, and wherein said second fatty acid biosynthesis gene is selected from the group consisting of fatty acid $\Delta$9-desaturase ($\Delta$9 stearoyl-ACP desaturase) genes and fatty acid $\Delta$12-desaturase (Oleoyl-PC $\Delta$12-desaturase) genes.

Preferably, the second fatty acid biosynthesis gene or gene fragment is different to the first fatty acid biosynthesis gene or gene fragment.

Those skilled in the art will be aware that the same end-product may be obtained by changing the series in which this procedure is conducted, or by using the second transgenic plant, rather than the first transgenic plant as a seed or pollen parent. Accordingly, the present invention clearly encompasses such alternatives.

A further aspect of the present invention provides a transgenic cotton plant having modified oil composition, and more particularly, modified content and/or composition of one or more fatty acids in an oil storage organ, such as, for example, the cotton seed, wherein said plant is produced by the inventive method described hereinabove.

Such plants will exhibit a range of desirable oil characteristics which will be apparent from the preceding discussion.

In one preferred embodiment, there is provided a cotton plant having increased oleic acid and stearic acid in the seed wherein said plant is produced by sexual hybridisation between a first cotton plant having increased oleic acid in the seed compared to an isogenic non-transformed cotton plant and a second cotton plant having increased stearic acid in the seed compared to an isogenic non-transformed cotton plant, and wherein said first cotton plant and/or said second cotton plant is/are produced in accordance with the inventive method of down-regulating expression of a gene selected from the group consisting of fatty acid $\Delta$9-desaturase ($\Delta$9 stearoyl-ACP desaturase) genes and fatty acid $\Delta$12-desaturase (Oleoyl-PC $\Delta$12-desaturase) genes.

In an alternative embodiment, this invention provides a cotton plant having decreased palmitic acid in the seed, wherein said plant is produced by sexual hybridisation between a first cotton plant and a second cotton plant, and wherein said first cotton plant and/or said second cotton plant is/are produced in accordance with the inventive method of down-regulating expression of a gene selected from the group consisting of fatty acid $\Delta$9-desaturase ($\Delta$9 stearoyl-ACP desaturase) genes and fatty acid $\Delta$12-desaturase (Oleoyl-PC $\Delta$12-desaturase) genes.

This aspect of the invention clearly extends to cotton plants consisting of the progeny of the primary transformant plants which comprise the introduced fatty acid biosynthesis gene or gene fragment.

This aspect of the invention further extends to all plant parts, and, in particular, to seed derived from the primary transformed plant or its progeny. Preferably, the seed will comprise the introduced fatty acid biosynthesis gene or gene fragment and, more preferably, such seed will have an oil having a modified fatty acid composition in accordance with the invention (i.e. low palmitic acid and/or high oleic acid and/or high stearic acid and/or low linoleic acid).

A further aspect of the present invention extends to the oil of a cotton plant, including any transgenic cotton plants, and progeny and seed thereof, produced in accordance with the inventive method.

A further aspect of the invention extends to the gene constructs and vector molecules essentially as described herein as being capable of use in performing the inventive method. This aspect of the invention clearly extends to the use of such gene constructs to produce any plants or plant parts, such as seed, having modified oil content and/or modified fatty acid composition, or to modify oil or fatty acid content and/or composition per se.

The present invention is further described with reference to the following non-limiting examples.

EXAMPLE 1

General Materials and Methods

Chemical Reagents

All chemicals used for in vitro use were at least analytical grade in standard. Solutions were prepared under sterile conditions using MilliQ $H_2O$, and autoclaved when appropriate. All the restriction enzymes used were purchased from New England Biolabs. All the polymerase chain reactions (PCR) were performed using AmpliTaq® DNA polymerase (Perkin Elmer, USA). The origin of other enzymes, kits used are indicated together with suppliers' names in the following sections of this chapter and in the remaining chapters. The synthetic oligonucleotides were made on an Applied Biosystems (USA) Model 377 DNA synthesiser in the Division of Plant Industry, CSIRO Australia. The radionucleotide, $\alpha$-$^{32}$P[dCTP], was supplied by Bresatec, Australia. DNA sequencing reactions were made using ABI$^{PRISM}$ kits (Perkin-Elmer), and sequence gel electrophoresis was carried out using an ABI373 DNA sequencer.

Growth of Plants

The seeds of four Australian native *Gossypium* species, including *G. australe, G. bickii, G. robinsonii* and *G. sturtianum* were purchased from Nindethana Seed Service, Western Australia, Australia. Seeds of other species were kindly provided by Australian Cotton Research Institute at Narrabri, NSW, Australia.

Several plants of *G. hirsutum* cv Siokra were grown in a glasshouse, using a temperature of 28/15–17° C. (day/night), and natural daylight supplemented with fluorescent lighting to provide a photoperiod of 16 hours per day. Potting soils were prepared by the plant growth facility at the Division of Plant Industry, CSIRO Australia. Unless otherwise stated, all the cotton plants were grown on a soil mix consisting of 75% Pryor's mix and 25% Potting mix. Flowers were tagged at anthesis, and embryos were harvested at 5 day intervals after anthesis, until the seeds were physiologically-mature.

Recombinant DNA Techniques

Unless otherwise specified, recombinant DNA techniques were carried out as described by Sambrook et al. (1989).

Growth of *Eschedchia coli*

Cultures of *E. coli* bacteria were grown overnight at 37° C., using solid or liquid Luria Broth media (LB; 10 g/l Bacto-tryptone, 5 g/l Bacto-yeast extract, 5 g/l NaCl, pH7.0). Each liquid culture was inoculated using a single bacterial colony and grown on a rotator The appropriate antibiotics, either Ampicillin (100 µg/ml) or Kanamycin (50 µg/ml) were added to bacterial growth media at the final concentration of 100 µg/ml and 50 µg/ml, respectively.

Transformation of Competent Cells with Plasmids

Transformation of competent cells with plasmids was performed according to the recommendations supplied with the Gene-Pulser (BioRad). Competent cells (50 µl) were combined with 5 µl deionised $H_2O$ ($dH_2O$) containing 5 ng plasmid DNA or 60 ng DNA from a ligation reaction. This mixture was transferred to a pre-chilled disposable Gene-Pulser®/*E. coli* Pulser cuvette, 0.2 cm (BioRad), and subject to electroporation using a Gene-Pulser (BioRad), set at 1.8 kV, 125 µFD and 200 w. Immediately following electroporation, the cells were mixed with 600 µl LB broth without antibiotic, transferred into a new Eppendorf tube and incubated at 37° C. for half a hour. 100 µl of culture were then plated onto a plate of solid LB media supplemented with appropriate antibiotic, and grown at 37° C. overnight.

A single bacterial colony was transferred into 2 ml of LB medium containing the appropriate antibiotic in a loosely capped 15-ml tube. The culture was incubated overnight at 37° C. with vigorous shaking 1.5 ml of the culture was poured into an Eppendorf tube and centrifuged at 12,000×g for 1 min at RT in a microfuge. The medium was removed by aspiration, leaving the bacterial pellet as dry as possible. 200 µl lysis buffer (0.1M NaOH and 0.5% SDS) was added and mixed by pipetting up and down. 200 µl 3M sodium acetate pH 6.0 was added and mixed by inverting many times and incubated on ice for 5 min. Following centrifugation for 10 min at room temperature, the supernatant was transferred into a new tube. Nucleic acids was precipitated by adding 1 ml cold ethanol, vortex to mix and centrifuge for 10 min at 40° C. The pellet was washed in 70% ethanol, centrifuging for 5 min at room temperature. After a briefly drying in a speedyvac, the pellet was resuspended in 30 µl $dH_2O$.

Preparation of Plasmid DNA

Plasmid DNA was prepared by a modification of the alkaline lysis procedure described by Sambrook et al.(1989), wherein bacteria were grown in Terrific Broth (TB), instead of LB, to produce a four- to eight-fold increase in the number of bacteria per milliliter of media, which leads, in turn, to higher plasmid yield. One liter of TB medium was made by mixing 100 ml of a sterile solution of 0.17 M $KH_2PO_4$, 0.72 M $K_2HPO_4$ and 900 ml of sterile, cool solution containing 12 g Bacto-tryptone, 24 g Bacto-yeast extract and 4 ml glycerol. In this modified protocol, plasmid DNA was precipitated using $PEG_{8000}$ (polyethylene glycol), to yield high-quality, super-coiled plasmid DNA that is relatively free of contaminating chromosomal DNA and RNA.

Briefly, a single colony was transferred to 2 ml of TB medium and incubated overnight at 37° C., with an appropriate amount of antibiotic, in 50-ml polypropylene tubes. 1.5 ml aliquots of culture pelleted by centrifugation for 1 min in a microcentrifuge. The supernatant was removed and the bacterial pellet was resuspended in 200 µl of GTE buffer (50 mM glucose, 25 mM Tris-HCl, 10 mM $Na_2EDTA$, pH 8.0) by pipetting up and down. 300 µl of freshly prepared lysis buffer (0.2N NaOH and 0.1% SDS) were added and mixed by inversion and incubated on ice for 5 min. This solution was neutralised by adding 300 µl of 3.0 M potassium acetate (pH4.8) and mixed by inverting the tube, and incubated on ice for 5 min. The cellular debris was removed by centrifugation for 10 min at room temperature, and the supernatant was transferred to a clean tube. RNaseA (Sigma, USA) was added to a final concentration of 20 µg/ml and incubated at 37° C. for 20 min. The supernatant was extracted twice with equal volume of phenol/chloroform/isoamyl alcohol (25:24:1). The plasmid DNA was precipitated by adding an equal volume of 100% isopropanol and pelleted by centrifugation for 10 min at room temperature. The DNA pellet was washed with 700 µl of 70% ethanol and then dried under vacuum. The pellet was dissolved in 32 µl of $dH_2O$, and then precipitated by adding 8.0 µl of 4 M NaCl and 40 µl of autoclaved 13% $PEG_{8000}$. After the thorough mixing, the sample was incubated on ice for 20 min, and then the plasmid DNA was pelleted by centrifugation for 15 min at 4° C. The supernatant was carefully removed and the pellet was rinsed with 700 µl of 70% ethanol. The DNA pellet was dried as before, and then resuspended in 20 µl of $dH_2O$.

Isolation of Plant Genomic DNA

All genomic DNA samples used were prepared according to Paterson et al. (1993). Briefly, three grams of leaf tissue were ground in liquid nitrogen to fine powder and kept in −20° C. freezer until required. The powder was transferred to 20 ml of cold nuclear buffer [1.0 M glucose, 100 mM Tris-HCl (pH 7–5), 5 mM $Na_2EDTA$, 2% (w/v) polyvinylpolypyrrolidone (average M.W. 40,000), 0.1% diethydithiocarbamic acid, 0.1% ascorbic acid, 0.2% mercaptoethanol] and inverted to homogenise. Following centrifugation at 1000×g for 20 min at 4° C., the pellets were suspended in 10 ml of 65° C. lysis buffer [100 mM Tris-HCl (pH8.0), 1.4 M NaCl, 20 mM $Na_2EDTA$, 2% CTAB (hexadecyl triammonium bromide), 2% polyvinylpolypyrrolidone (average M.W. 40,000), 0.1% diethydithiocarbamic acid, 0.1% ascorbic acid, 0.2% mercaptoethanol] and incubated for 20 min in 65° C. water bath. An equal volume of chloroform/isoamyl alcohol was added and mixed by inverting many times. Following centrifugation at 4,500×g for 10 min, the upper aqueous phase was transferred to a new tube. This extraction step was repeated once more prior to the precipitation of DNA by addition of two volumes of 100% ethanol. The DNA was hooked out with a glass hooker and rinsed in 70% ethanol, air dried and resuspended in 500 µl of TE buffer, and then extracted twice with equal volumes of phenol/chloroform/isoamyl alcohol. The DNA was precipitated by adding 1/10 volume of 3M NaAcetate, and two volume of 100% ethanol. Following rinsing in 70% ethanol, the DNA was air dried and resuspended in 1 ml of 1M CsCl in TE buffer.

Purification of Genomic DNA by CsCl Gradient

To purify cotton genomic DNA using cesium chloride gradients, 2.5 ml of 5.7 M CsCl in TE was added to a Beckman polyallomer 13×51 mm tube (non sealing) using a disposable pipette. 30 µl ethidium bromide (i.e. EtBr;10 mg/ml) was added to the plant genomic DNA in 1.0 M CsCl-TE buffer and laid on the top of the CsCl cushion. Following centrifugation at 35,000×rpm for 16 hours at 18° C. in a SW50.1 rotor, the DNA band was removed using a 1-ml syringe and 18 gauge needle and added to a new 10-ml tube containing 5 ml of CsCl-saturated isopropanol. After gentle mixing, the top layer containing EtBr was discarded. Three more extractions with 1 ml of CsCl-saturated isopropanol were carried out. DNA was hooked out with a glass rod following adding three volume of 70% ethanol. After resuspending the DNA in 500 µl of TE, the DNA was precipitated by adding 50 µl of 3 M NaAcetate and 1 ml of 100% ethanol and rinsed in 70% ethanol prior to resuspension in 300 µl TE buffer.

Isolation of RNA

Sterile, disposable plasticware which is essentially free of RNases was used for the preparation and storage of RNA without pretreatment. Glassware used for RNA isolation were baked at 180° C. overnight. All the solutions were treated with 0.1% DEPC (diethyl pyrocarbonate) for at least 12 hours at 37° C. and then autoclaved for 20 min at 15 psi on liquid cycle.

Two grams of cotton embryos or leaf tissues were ground in liquid nitrogen and mortared to a fine powder which was subsequently prickled into a beaker containing 22 mls cold extraction buffer and stirred constantly. The extraction buffer consists of 200 mM Tris-HCl pH8.5, 1.5% Lithium dodecylsulfate, 300 mM LiCl, 10 mM $Na_2EDTA$, 1% sodium deoxycholate, 1% Nonidet P-40. This was followed by adding 5% insoluble PVP, 90 mM mercaptoethanol, 10 mM DTT (dithiothreitol), 0.1% DEPC and stirred for 10 min prior to being transferred to a Corex tube. Then 18.4 ml of 3M ammonium acetate was added and mixed well. It was centrifuged at 6,000×rpm for 20 min at 4° C. The supernatant was transferred to a new tube and precipitated by adding 1/10 volume of 3 M NaAc, pH5.2 and ½ final volume of cold isopropanol and stored at −20° C. for 1 hour prior to centrifugation at 6,000×rpm for 30 min using a swing rotor. The pellet was resuspended in 1 ml $dH_2O$ and transferred to two Eppendorf tubes (500 µl in each tube). The suspension was extracted with an equal volume of phenol/chloroform/isoamyl alcohol solution (25:24:1) and the phases were separated by centrifugation for 5 min at 4° C. The aqueous top layer was carefully transferred into a new Eppendorf tube and it was extracted again with chloroform as above.

Half volume of 5M LiCl was added to the aqueous sample, mixed well and left on ice for 3 hours prior to centrifugation at 12,000×rpm for 15 min at 4° C. The pellet was resuspended in 50 µl $dH_2O$. Finally, the RNA sample was precipitated by adding 5 µl NaAc and 138 µl cold ethanol and incubated on dry ice for 30 minute prior to centrifugation for 15 min at 4° C. The RNA pellet was dried in a speedyvac and then dissolved in 30 µl RNase-free $H_2O$.

Electrophoresis of DNA on Agarose Gels

Agarose mini-gels were cast from 50 ml of 1% (w/v) melted agarose solution containing 1×TAE buffer (0.04 Tris-acetate, 1.0 mM $Na_2EDTA$, pH 8.0), using a 5×8 cm mould, and a well-comb suitable for making wells of 15 µl volume. DNA samples were mixed with 0.2 volumes of 6×FLB loading buffer (15% ficoll 400, 0.25% bromophenol blue, 0.25% xylene cyanol) and loaded into the wells. A DNA size marker consisting of EcoRI-digested SPP-1 DNA (Bresatec, Australia) was loaded into a well alongside the sample DNAs. Electrophoresis was performed at 50–70 V in 1×TAE buffer until the dyes had separated sufficiently, after which time gels were soaked in 0.5 mg/l solution of ethidium bromide (EtBr) for 10 min, destained by rinsing in water for 10 in and photographed using UV light of wavelength 302 nm.

Transfer of Cotton Genomic DNA to Nylon Membranes for Hybridisation

Cotton genomic DNA (approximately 10.0 µg DNA in 5.0 µL volume) was digested at 37° C. overnight in a 20-µl reaction containing 1× concentration of an appropriate buffer, generally supplied with the restriction enzyme. A 0.7% agarose gel in 1×TBE (0.045 M Tris-borate, 1.0 mM $Na_2EDTA$, pH8.0) was cast using a 15×20 cm mould. Genomic DNA digests were electrophoresed on the agarose gel overnight at 20 mA in 1×TBE buffer, until the bromophenol blue from the loading dye had run ¾ of the length of the gel. Each gel was shaken gently in 500 ml of 0.1 M HCl for 5 min, followed by rinsing and shaken in $dH_2O$ for a further 5 min to remove the acid. DNA was transferred from the gel to Hybond $N^+$ membrane (Amersham) by Southern transfer (Southern, 1975) for 4 hours, using 0.4 N NaOH as the transfer solution. After transferring, the membrane was rinsed in 2×SSC (1.75% NaCl, 0.88% sodium citrate, pH7.0) briefly and blotted dry between 2 sheets of 3M membrane paper at room temperature.

Transfer of Cotton RNA to Nylon Membranes for Hybridisation

To prepare a 300 ml of 1% agarose gel for RNA electrophoresis, 3 grams agarose and 30 ml 10×MOPS [3-(N-morpholino)propanesulfonic acid] buffer were added to 255 ml $dH_2O$ and dissolved by heating. Formaldehyde (16.2 ml of 37% stock solution) was added to the agarose solution when it had cooled to 50° C., and mixed by swirling. Total RNA (20 µg) was mixed with 20 µl of loading buffer and then heated to 95° C. for 2 min to denature RNA. The loading buffer was freshly prepared by mixing 0.72 ml formamide, 0.16 ml 10×MOPS buffer, 0.26 ml formaldehyde (37% stock), 0.1 ml 80% (v/v) glycerol, 0.08 ml bromophenol blue (saturated solution) and 0.18 ml $dH_2O$. Ethidium bromide (1 µl) was then added to each sample. The RNA samples were electrophoresed in 1×MOPS buffer until the bromophenol blue dye migrated three-fourths along the length of the gel. The RNA was viewed using under UV light using a transilluminator, and photographed. The two abundant rRNA species visible under UV light, namely the 28S rRNA (5 kb) and 18S rRNA (2 kb), were used as molecular weight standards. Immediately prior to transfer, the RNA gel was rinsed for 20 min each in two changes of 500 ml of 10×SSC to remove formaldehyde from gel. This was immediately followed by transferring the RNA to Hybond $N^+$ membrane using 0.05 N NaOH as the transfer buffer, for a period of 3 hours.

Preparation of $^{32}$P-labelled DNA Probes

Radioactively labelled probes were synthesised by random priming, essentially as described by Feinberg and Vogelstein (1983), using a random priming kit obtained from Amersham (USA). Purified cloned insert DNA (20 ng) was combined with 6.0 µl of random oligonucleotides (Amersham). This the mixture was incubated at 95° C. for 5 min to denature the DNA and quickly chilled on ice for 5 mins. Reactions were carried out at 37° C., for 1 hour, in a total volume 25 μl, comprising 10 μl of probe labelling buffer (0.5 M HEPES, 0.125 M Tris-HCl, 12.5 mM DTT, 12.0 mM MgCl$_2$, 1.0 mg/ml BSA); 2.5 μl dNTP mixture (0.2 mM dATP, 0.2 mM dTTP, 0.2 mM dGTP); 1.0 unit Klenow fragment; 3.0 μl [α-$^{32}$P]dCTP (10 μCi/μl), and MilliQ H$_2$O. To remove the unincorporated dNTPs, the probe was purified by passing the reaction mixture through a Sephadex® G-50 NICK® Column (Pharmacia) according to the manufacturer's instructions.

Hybridisation and Autoradiography

Nylon membranes with nucleic acid bound thereto were prehybridised in hybridisation bottles containing 5–20 ml of the prehybridisation solution essentially as described by Khandjian (1987) (50 mM Tris-HCl pH7.5, 1M NaCl, 50% formamide, 10× Denhardt's solution, 10% dextran sulfate, 1% SDS, 0.1% sodium pyrophosphate, 0.1 mg/ml herring sperm DNA). The bottles were placed in a hybridisation oven equipped with a rolling apparatus for at least 4 hours at 42° C.

Following prehybridisation, labelled probe DNA was denatured by heating for 10 min at 95° C., and then placed on ice for 5 min. Denatured probed was added to the prehybridisation mixture. The hybridisation was performed at 42° C. for 16 hours. Unless otherwise stated, membranes were then briefly washed in 2×SSC, 0.1% SDS at 65° C. This was followed by two further washes in 0.2×SSC, 0.1% SDS at 65° C. for 15 min each. Autoradiography was performed for one to five days at −80° C. with a Kodak X-ray film and an intensifying screen.

Construction of a Cottonseed cDNA Library

Cotton poly(A)$^+$ RNA was isolated from total RNA prepared as described above, using a mRNA purification kit (Pharmacia), essentially as described by the manufacturer. To prepare cDNA, a cDNA synthesis kit (Pharmacia) was used, essentially as described by the manufacturer, using 1–5 μg poly(A)$^+$ RNA as starting material. The double-stranded cDNA product was blunt-ended, and ligated to EcoRI/NotI adaptors, using standard procedures, Following the removal of excess unligated adaptors, the cDNA was cloned into the bacteriophage vector Lambda ZAPII (Stratagene, USA), and packaged using a commercially-available packaging system (Stratagene, USA), according to the manufacturer's instructions.

Titration of Bacteriophage Particles in cDNA Libraries

To prepare host cells, a single colony of the bacterial host XL1-Blue MRF' was transferred into 50 ml of LB medium supplemented with 0.2% maltose and 10 mM MgSO$_4$ in a sterile Erlenmeyer flask and grown overnight with shaking at 30° C. This lower temperature ensures that the cells will not overgrow. The cells were centrifuged in a sterile conical tube for 10 min at 2,000×rpm. The pellet was gently resuspended in 10 mM MgSO$_4$ to the final cell density of OD$_{600}$=0.5.

To titre the bacteriophage, each of a serial dilution of the packaging reaction (1, 1/10, 1/100), and 200 μl of the host cells, were mixed and incubated at 37° C. for 15 min. Then, 2–3 ml of cooled (48° C.) top agar (0.5% NaCl, 0.2% MgSO$_4$.7H$_2$O, 0.5% yeast extract, 1% NZ Amine, pH7.5, 0.7% agarose), 15 μl of 0.5 M IPTG (isopropylthio-β-Δ-galactoside) and 50 μl of X-gal (5-bromo-4-chloro-3-indolyl-β-D-galactoside, 250 mg/ml in dimethylformamide) was added, and poured onto NZY plates (0.5% NaCl, 0.2% MgSO$_4$.7H$_2$O, 0.5% yeast extract, 1% NZ Amine, pH7.5, 1.5% agar). Plates were incubated for at least 6–8 hours at 37° C.

The cDNA libraries described herein generally contained about 92% recombinant bacteriophage particles, in a total of about 1.5×10$^7$ plaque forming units (pfu) per ml of unamplified library.

Amplification of cDNA Libraries

Twenty aliquots of the packaged unamplified cDNA library, each containing about 5×10$^4$ pfu, were mixed with 600 μl of host cells prepared as described hereinabove, in Falcon 2059 tubes, and the mixtures were incubated at 37° C. for 15 min. Each aliquot of infected bacteria was mixed with 6.5 ml of cooled (about 48° C.) melted top agar and spread evenly onto a freshly poured 150-mm plate of bottom agar. The plates were incubated at 37° C. for 6–8 hours. Each of these plates was then overlaid with 8–10 ml of SM buffer and incubated at 4° C. overnight with gentle rocking to elute the bacteriophage. The bacteriophage suspension was recovered from each plate and pooled into a sterile polypropylene container and chloroform was added to a final concentration of 5% (v/v). After 15 min incubation at room temperature, cell debris was removed from the bacteriophage suspension by centrifugation at 2,000× g for 10 min. The supernatant was recovered and aliquots were stored in 7% DMSO (dimethyl sulfoxide) at −70° C.

The titre of amplified cottonseed cDNA libraries prepared according to this procedure was generally about 2×10$^9$ pfu/ml.

Screening of cDNA Libraries

Amplified cottonseed cDNA libraries were plated onto 20 petri dishes (150 mm) containing NZY medium, by infecting 600 μl host cells prepared as described previously (E. coli XL1-Blue MRF' cells) with about 50,000 pfu, and then adding 6.5 ml top agar to each plate as described above. When the plaques became visible, generally after about 8 hours of incubation at 37° C., the plates were chilled at 4° C. for about 2 hours.

Plates were overlaid with Hybond N$^+$ (Amersham) membranes which had been numbered previously, and the membrane's position on each plate was keyed. When the membranes had been thoroughly adsorbed to the plates, they were removed gently so as to not remove the top agar, and placed onto several layers of 3MM membranes saturated with denaturing buffer (1.5 M NaCl, 0.5 M NaOH) for 7 min The membranes were then neutralised, by soaking on two changes of neutralising buffer (1.5 M NaCl, 0.5 M Tris-HCl, pH7.0, 0.001 M EDTA) for 3 min each. The membranes were washed in 5×SSC briefly and blotted dry between two layers of 3 MM membranes. Membranes were then fixed by laying on top of several layers of 3 MM membranes saturated with 0.4 N NaOH for 10 min and rinsed in two changes of 5×SSC briefly before being blotted dry between 3MM membranes.

For hybridisations, the membranes were soaked in 2×SSC briefly, transferred to enough prehybridisation buffer (described hereinabove) to cover the membranes completely, and incubated at 42° C. for at least 4 hours with gentle shaking. Following prehybridisation, the [α-$^{32}$P] dCTP-labelled DNA probe (described hereinabove) was denatured by incubating at 95° C. water bath for 5 min, chilled rapidly on ice, added to the prehybridisation buffer, and the reaction incubated at 42° C. for 16 hours.

The hybridisation solution was removed and the membranes were immediately washed in 2×SSC, 0.1% SDS briefly at 65° C., unless otherwise stated. This was followed by two consecutive washes in 0.2×SSC, 0.1% SDS for 15 min each. Unless otherwise stated, all the washes were normally carried out at 65° C. Following this washing, the excess liquid was removed by blotting on Whatman 3 MM paper. The membranes were then placed between two sheets of plastic wrap in a cassette and exposed to X-ray film (Kodak) overnight at −80° C. with an intensifying screen. The positive-hybridising plaques were identified and transferred from the original plates, into 1 ml of SM buffer and 20 μl of chloroform and mixed.

Positive-hybridising plaques were purified by re-screening as before, using 50–100 plaques per small NZY plate.

Following plaque-purification, the ExAssist/SOLR system (Stratagene, USA) was used to excise the pBluescript SK(-) phagemid from the Lambda ZAPII vector, as described by the manufacturer.

Nucleotide Sequence Analysis

DNA sequencing was performed with an ABI 373 system (Applied Biosystems) using dye terminator and dye primer sequencing reactions. Sequence comparisons and alignments were performed with programs in the GCG package (Devereux et al., 1984).

EXAMPLE 2

Determining Oil Content and Fatty Acid Composition of Developing and Mature Cotton Seed The total lipid content of cottonseed, or seed oil, was extracted by a modification of the method of Folch et al. (1957). Dry cottonseeds were ground in a coffee grinder. Immature embryos were harvested immediately before grinding into powder in liquid nitrogen with pestles and mortars. Approximately 4 grams ground powder from mature seed samples were weighed out and the exact weights were recorded. Because of the limited availability of immature embryos, only 1–2 gram samples were used. They were placed into an Erlenmeyer flask. Total lipids were then extracted with 60 ml of Folch reagent (2:1 v/v chloroform:methanol solution, 15 ml per gram of sample) The extracts were filtered through Whatman No. 1 filter paper into a 100-ml graduated cylinder and made up to 60 ml volume. Then they were washed with 12 ml of saline solution (0.88% NaCl, 20% volume of the extract) and the phases were allowed to separate. The upper phase, containing water, methanol and water soluble material was siphoned off and discarded. The lower phase of chloroform and lipids was further washed with a chloroform:methanol:saline (3:47:48 v/v) solution. Again phases were allowed to separate. The final volume of the lower chloroform:lipid was recorded and the upper layer siphoned off and discarded. 10 ml of the chloroform extract and 1 ml of internal standard, heptadecanoic acid (C17:0, 5.196 mg/ml) were transferred into a preweighed culture tube with a screw cap. The sample was evaporated to dryness under a nitrogen gas stream on a 70° C. heating block. The amount of crude lipids per gram of sample was determined by weighing the tube containing the dried sample.

Five milliliters of the methylating reagent, a mixture of boron trifluoride:methanol:hexane (35:45:20) was added to the culture tube containing dried lipid and capped tightly with a teflon lined crew cap. Then it was incubated in a 90° C. water bath for 45 min with frequent shaking. After cooling down to room temperature, 5 ml of water and 5 ml of hexane were added to the mixture. Following shaking and phase separation, the top hexane layer containing the fatty acid methyl esters was transferred into a new tube and used in the GLC analysis.

The fatty acid composition of the lipids was determined by GLC, using a Varian Gas Liquid Chromatography apparatus (Model 3400), equipped with a fused capillary column DB624 (J & W Scientific). The injector and detector temperature were 220° C. and 240° C., respectively. The nitrogen flow rate was 30 ml/minute. The following program was used in the GLC analysis:

(i) the column temperature was held at 70° C. for 3 min;

(ii) the column temperature was increased to 160° C. at a rate of 30° C./min, and then held at 160° C. for 10 min; and (ii) the column temperature was increased to 230° C. at a rate of 7° C./min, and then held at 230° C. for 4 min.

A fatty acid standard containing lauric acid (C12:0), myristic acid (C14:0), palmitic acid (C16:0), stearic acid (C18:0), oleic acid (C18:1), linoleic acid (C18:2), linolenic acid (C18:3), arachidic acid (C20:0), behenic acid (C22:0), eicosadienoic acid (C20:2), and lignoceric acid (C24:0), was used to identify the fatty acids present in cotton seed oil.

Fatty acid peaks were identified by comparing the fatty acid methyl ester peaks and retention times of standards with sample peaks. An electronic integrator was used to calculate the total area of peaks and the area of each fatty acid peak was expressed as a percentage of the total area.

EXAMPLE 3

Oil Content and Fatty Acid Composition of Cotton Seed Derived from Several Elite Cotton Cultivars Using the procedure described in Example 2, we determined the oil composition of cotton seed derived from several elite Australian cotton cultivars, and some other commercial and non-commercial cotton species.

In all cultivars tested, palmitic acid (C16:0) represents the major saturated fatty acid, while low level of other saturated fatty acids including myristic acid (C14:0) and stearic acid (C18:0) were also detected. Oleic acid and linoleic acid were the two major unsaturated fatty acids, whilst a very low level of palmitoleic acid (C16:1) was also detectable. The low level of stearic acid in cottonseed oil is probably because of the strong activity of a $\Delta 9$ stearoyl-ACP desaturase enzyme which converts most of the stearic acid to oleic acid, which is then further desaturated by a microsomal $\omega$-6 desaturase, to form linoleic acid. Linoleic acid accounts for more than 50% of total fatty acid composition of cotton seed, indicating a strong microsomal $\omega$-6 desaturase activity in cottonseeds.

GLC analyses did not differentiate cyclopropenoid fatty acids (CPFA) from other unsaturated fatty acids. Previous studies have demonstrated that cottonseed oil contains less than 1% cyclopropenoid fatty acids (CPFA), mainly sterculic and malvalic acids, which contain one double bond at the site of a propene ring, either at the 9–10 or 8–9 position (Phelps et al., 1964; Allan et al., 1967). CPFA is unstable during the standard lipid extraction process, but derivatives of CPFA have been quantitated by modified GLC technique and high performance liquid chromatography (Fisher and Schuller, 1981; Fisher and Cherry, 1983; Pandey and Subrahmanyam, 1988).

The mean values for percentage oil content and the component fatty acids in the cottonseed oils from 20 entries are reported in Table 4. Student-Newman-Keuls test for the oil content and component fatty acids of various entries indicated that species or genotypes have a significant influence on the oil content and the majority fatty acid compositions of cottonseed oil (except for C14:0) at the 5 percent level of probability.

The four Australian wild diploid *Gossypium* species contained significantly lower oil content than the remaining entries examined. They were also found to contain a significantly higher level of linoleic acid, and lower levels of palmitic and oleic acids. In contrast, the only A-genome diploid species tested, *G. arboreum*, was found to contain significantly high levels of oleic acid, however this species also had significantly low linoleic acid. This result is largely in agreement with previous studies on the chemical survey in genus *Gossypium* (EI-Nockrashy et al., 1969; Khattab et al., 1977).

The major Australian elite cotton cultivars, SicalaV2, SiokraL22, SiokraL23 and CS50 had the highest oil content, whereas Sicala33 and Sicala34 were found to contain moderate levels of oil which were not significantly different from the American cultivar, Acala R.

With respect to the fatty acid composition of the Australian elite cotton cultivars, SiokraL22, SiokraL23, Sicala33, and Sicala34, contain relatively high levels of palmitic acid and moderate levels of unsaturated fatty acids.

The present study indicates that there are some, but limited variations of oil content and fatty acid composition among the elite Australian cotton varieties increase of percent oil content, wherein the linoleic acid content rose from 22% to almost 50%. There was only a slight increase thereafter. We also observed a continuous decrease in the percentage of palmitic acid in the seed, between 15–35 DAA, a decrease which slowed in later developmental stages. Interestingly, oleic acid levels decreased gradually throughout development of the cottonseed. Stearic acid content of the seed decreased from about 9% of total lipids at 15 DAA, to only about 2.5% at 30 DAA, and remained at that level thereafter. Myristic acid and palmitoleic acid remained at relatively low levels throughout the period of embryo development.

TABLE 4

Oil content and fatty acid composition of seed oil of some *G. hirsutum* cotton cultivars and other *Gossypium* species

| Entries | Oil Content (%) | Fatty Acid (%) | | | | | |
|---|---|---|---|---|---|---|---|
| | | 14:0 | 16:0 | 16:1 | 18:0 | 18:1 | 18:2 |
| G. australe | 16.2b | 0.7a | 21.5a | 1.6b | 1.7a | 11.0b | 62.1f |
| G. bickii | 14.6a | 0.8a | 20.6a | 0.9a | 3.5c | 8.6a | 64.1g |
| G. robinsonii | 17.5b | 0.9a | 22.8abc | 0.6a | 2.7b | 10.4ab | 60.0e |
| G. sturtianum | 17.3b | 1.1a | 20.4a | 0.5a | 2.6b | 11.2b | 62.5fg |
| G. arboreum | 22.4de | 0.7a | 21.0a | 1.0a | 3.6c | 27.2e | 45.3a |
| G. barbadense | 21.1cd | 0.7a | 24.4bcd | 0.7a | 2.2ab | 19.4d | 52.0bc |
| G. hirsutum:- | | | | | | | |
| cv Acala R | 23.0ef | 0.6a | 24.4bcd | 0.5a | 2.3ab | 16.9cd | 54.4cd |
| cv BAR7/8 | 21.1cd | 0.9a | 23.9bc | 0.6a | 2.3ab | 15.6c | 56.1d |
| cv DP90 | 22.0cde | 0.7a | 26.9d | 0.6a | 2.3ab | 16.3cd | 52.5bc |
| cv MCU-5 | 20.6c | 0.7a | 22.4ab | 0.8a | 2.1ab | 16.4cd | 56.1d |
| cv Lintless 28 | 23.7efg | 0.8a | 24.3bc | 0.5a | 2.6b | 18.7cd | 52.6bc |
| cv Lintless 53 | 23.7efg | 0.8a | 25.5cd | 0.5a | 3.7c | 18.3cd | 50.6b |
| cv Sicala33 | 23.2ef | 0.8a | 24.6bcd | 0.7a | 2.7b | 16.7cd | 53.4c |
| cv Sicala34 | 23.0ef | 0.7a | 24.6bcd | 0.5a | 2.5b | 16.7cd | 54.0cd |
| cv CS50 | 25.0gh | 0.6a | 24.1bc | 0.4a | 2.5ab | 17.7cd | 54.1cd |
| cv CS65 | 23.8efg | 0.9a | 22.6ab | 0.6a | 2.5ab | 16.3cd | 56.4d |
| cv Siokra L22 | 24.5fgh | 0.8a | 24.9bcd | 0.7a | 2.7b | 17.2cd | 53.1bc |
| cv Siokra L23 | 24.7fgh | 0.7a | 25.1bcd | 0.7a | 2.5ab | 17.5cd | 52.7bc |
| cv Siokra 1-4 | 25.5h | 0.7a | 24.4bcd | 0.5a | 2.4ab | 17.5cd | 54.2cd |
| cv Sicala V-2 | 26.0h | 0.7a | 23.8bc | 0.5a | 2.4ab | 17.9cd | 54.1cd |

* The least significant differences are calculated for the 5% level of probability. Within columns means having a letter in common are not significantly different.

EXAMPLE 4

Developmental Changes in the Fatty Acid Composition of Cotton Seed

The oil accumulation and changes of fatty acid composition in developing cottonseed embryos aged 15–65 days-after-anthesis (DAA) is illustrated in FIG. 1. In particular, little oil was detected in seeds at 15 DAA. Between 15–20 DAA, oil accumulation was also relatively low, however a rapid increase in oil accumulation occurred between 20–35 DAA. After 35 DAA, the rate of oil accumulation in the seed slows, and is essentially constant. These observations are consistent with previous reports (EI-Nockrashy et al., 1975; Kajimoto et al., 1979).

We also measured the amounts of the six major fatty acids present in cotton seed, myristic acid (C14,0), palmitic acid (C16:0), palmitoleic acid (C16:1), stearic acid (C18:0), oleic acid (C18:1) and linoleic acid (C18:2), in developing embryos (FIG. 1). The rate of synthesis of linoleic acid was higher than the rates of syntheses for the other fatty acids. A rapid increase in synthesis of linoleic acid was observed in the period 15 to 30 DAA, concomitant with the rapid The data presented in FIG. 1 suggest that the oil content and fatty acid composition of cotton seed is determined at an early stage of development, approximately 20–35 DAA In fact, the majority of the total oil found in the mature cottonseed is synthesised during latter 30 days of embryo development, and this appears to be a critical time in cotton seed oil production.

EXAMPLE 5

Isolation and Cloning of cDNAs Encoding Cotton Fatty Acid Δ9-Desaturase (Δ9 Stearoyl-ACP Desaturase)

A nucleotide sequence comprising a cotton fatty acid Δ9-desaturase (Δ9 stearoyl-ACP desaturase) gene was isolated essentially as described by Liu, Q., et al. (1996).

Briefly, a pair of degenerate PCR primers were synthesised that contained some possible codons corresponding to the open reading frames (ORFs) of peptide sequences among Δ9-stearoyl-ACP desaturase cDNAs from castor bean (Shanklin and Somerville, 1991), cucumber (Shanklin et al., 1991) and flax (Singh et al., 1994). The sequences of the primers are as follows (degenerate positions are in parentheses):

D9S (SEQ ID NO: 8):
5'-ATGGC-(G/T)CT(C/G)A(A/G)GCT(C/G/T)CAT(C/G)C-3';

and

D9A (SEQ ID NO: 9):
5'-TCA(G/C)AG(C/T)TT(C/A)AC(T/C)TG-(T/C)CTAT-3'.

Total RNA was isolated from cottonseed embryos at 25–35 days post anthesis, and poly(A)+ RNA purified therefrom according to procedures described herein above.

Single stranded cDNA template for reverse transcriptase-PCR (RT-PCR) was synthesised at 45° C. from poly(A)+ RNA using a Superscript kit (Gibco BRL), according to the manufacturer's instructions. RT-PCR amplifications were carried out in 50-µl reaction volume, containing 50 pmol of each primer D9S and D9A, and single-stranded cDNA derived from 20 ng of poly(A)+ RNA. The mixture was heated to 96° C. for 5 min prior to commencing the reaction, and 3 units of AmpliTaq® DNA polymerase (Perkin-Elmer Cetus) was added. Cycling of reaction mixtures was performed in a Corbett FTS960 thermal cycler, using 40 cycles of the following program:

(i) 94° C. for 30 sec;
(ii) 48° C. for 30 sec; and
(iii) 72° C. 1 min 10 sec.

These 40 cycles were followed by incubation for 10 min at 72° C.

Under these conditions, an approximately 1 kb DNA fragment comprising a protein-encoding region, was obtained. The identity of the cloned PCR product as a partial cDNA encoding Δ9-stearoyl-ACP desaturase, was confirmed by DNA sequencing. This fragment was cloned into a T®-vector (Promega).

The partial cDNA was excised from purified plasmid DNA, and radio-labelled with [α-$^{32}$P]dCTP as described hereinabove. The labelled probe was used to screen a cottonseed cDNA library, prepared using the λZAPII vector (Stratagene) and poly(A)+ RNA isolated from the embryo tissues of developing seed of G. hirsutum cv Deltapine-16 as described hereinabove, under high stringency hybridisation conditions. Ten plaques which showed strong positive signals in the primary screening were selected and further purified by secondary and tertiary screenings. Phagemid containing the Δ9-stearoyl-ACP desaturase cDNA was excised in vivo using ExAssist/SOLR system.

All of the 10 clones idenified were identical, based on the partial nucleotide sequence and restriction mapping analyses. One clone, designated ghSAD-1, was completely sequenced (SEQ ID NO: 1; FIG. 2). The nucleotide sequence of ghSAD-1 is also publicly available under the GenBank Accession No. X95988.

Clone GhSAD-1 is 1553 bp in length, and comprises a 12 bp 5'-UTR, a 350 bp 3'-UTR, and a 1191 bp ORF which encodes a polypeptide of 397 amino acid residues in length (SEQ ID NO: 2). The nucleotide sequence surrounding the putative ATG start site has 78% identity to the consensus for plant translation initiation proposed by Lütcke et al. (1987). The identity of ghSAD-1 as encoding Δ9 stearoyl-ACP desaturase was confirmed by analysis of its sequence identity to other Δ9 stearoyl-ACP desaturase-encoding cDNAs in the GenBank database.

The deduced G. hirsutum Δ9 stearoyl-ACP desaturase polypeptide contains an apparent plastid transit peptide sequence at its N-terminus, consistent with its plastid localisation. Based on homology with the castor bean polypeptide (Knutzon et al., 1991), the amino acid residue at position 32 of the polypeptide encoded by ghSAD-1 is the most likely cleavage site for the plastid transit peptide. Residues immediately preceding amino acid 33 of SEQ ID NO: 2 conform closely to the consensus cleavage site for plastid transit peptides proposed by Gavel and von Heijne (1990). Accordingly, it is possible that the ghSAD-1 cDNA encodes a precursor polypeptide comprising a 32 amino acid-long transit peptide, to facilitate translocatation of the polypeptide into the proplastid. Subsequent cleavage of the transit peptide possibly produces a mature protein of 365 amino acid residues in length. As with other, previously characterised, plant Δ9 stearoyl-ACP desaturases, the deduced amino acid sequence of ghSAD-1 is highly hydrophilic, consistent with the soluble nature of the enzyme. No transmembrane helices were found in the whole polypeptide sequence using the internet program SOSUI (http://www.tuat.ac.jp/~mitaku/sosui/).

As indicated in Table 5, there is considerable homology between ghSAD-1 and Δ9 stearoyl-ACP desaturase cDNAs from other plant species at the nucleotide and amino acid levels. As expected, the mature Δ9 stearoyl-ACP desaturase proteins are more highly conserved, than the transit peptides of the full-length potypeptides.

Amino acids 322–342 of SEQ ID NO: 2 (FIG. 2) conform to a fatty acid desaturase family II signature (http://www.genome.ad.jp/SIT/MOTIF.html). An iron-binding motif, containing two repeats of the amino acid sequence Glu-Xaa-Xaa-His (i.e. EXXH) separated by approximately 100 amino acids, is also found in the cotton Δ9 stearoyl-ACP desaturase polypeptide (bold type in FIG. 2), as with other class II di-iron proteins, including the R2 component of a ribonucleotide reductase and the soluble bacterial hydrocarbon hydroxylases (Fox et al., 1994).

EXAMPLE 6

Expression of the ghSAD-1 Gene During Cotton Seed Development

Total RNA, from developing cotton seed embryos at 25, 30, 36, 45 DAA, or leaves, was isolated, electrophoresed on an agarose gel, trasnferred to nylon membranes, and probed with a labelled DNA fragment derived from the 3'-UTR of the ghSAD-1 clone, essentially as described hereinabove. Owing to the difficulty in obtaining RNA samples from very early stages of embryo development, gene expression prior to 25 DAA was not examined.

Figure 3:
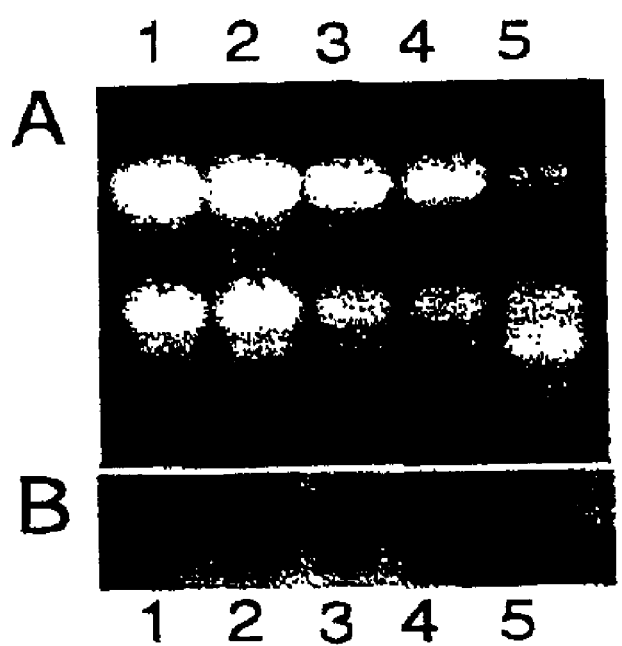
FIG. 3 is a copy of a photographic representation of a Northern blot hybridisation of developing cotton seed embryos, and cotton leaf tissue. Panel (A) shows an ethidium bromide-stained RNA gel. Panel (B) shows the hybridisation signal obtained using a [$\alpha$-$^{32}$P]dCTP-labelled ghSAD-1-specific probe. Lanes 1–4 represent RNA samples isolated from embryos at 25, 30, 36, and 45 DAA, respectively. Lane 5 represents RNA isolated from young leaves.

As demonstrated in FIG. 3, high expression was detected in all four stages of embryo development examined. However, there was no detectable transcript in leaf tissue. Highest seed-specific expression was obseerved at 30 DAA, and 35 DAA. We speculate that the expression of ghSAD-1 is induced well before 25 DAA.

TABLE 5

Similarities between ghSAD-1 and other stearoyl-ACP Δ9-desaturase cDNAs

| | | Similarity (%) to ghSAD-1 | | | |
|---|---|---|---|---|---|
| Plant Species | Accession No. | ORF (nt) | overall identity | Mature Peptide | Reference |
| Arabidopsis thaliana | X93461 | 71.4 | 84.9 | 86.3 | GenBank X93461 |
| Arachis hypogaea | AF172728 | | | | Tate et al., 1999 |
| Brassica napus | X63364 | 71.8 | 86.1 | 88.5 | Slocombe et al., 1992 |
| Brassica juncea | AF153420 | | | | Vageeshbau et al., 1999 |
| Brassica rapa | X60978 | 73.0 | 86.9 | 88.8 | Knutzon et al., 1992 |
| Elaeis guineensis | U68756 | 72.4 | 87.5 | 89.0 | Shah and Rashid, 1996 |
| Sesamum indicum | D42086 | 74.7 | 88.9 | 90.4 | Yukawa et al., 1994 |
| Carthamus tinctorius | M61109 | 72.8 | 89.2 | 91.2 | Thompson et al., 1991 |
| Coriandrum sativum | M93115 | 63.3 | 77.8 | 78.5 | Cahoon et al., 1992 |
| Cucumis sativa | M59858 | 73.8 | 88.4 | 89.9 | Shanklin et al., 1991 |
| G. hirsutum | AJ132636 | | | | Liu et al, 2000 |
| G. hirsutum | AI730379 | | | | Blewitt et al., 1999 |
| Glycine max | L34346 | 74.9 | 88.8 | 90.4 | Chen and Moon, 1995 |
| Helianthus annuus | U70374 | 70.8 | 85.4 | 88.0 | GenBank U70374 |
| Linum usitatissimum | X90762 | 68.4 | 80.7 | 82.5 | Singh et al., 1994 |
| Linum usitatissimum | AJ006957 | | | | Jain, 1998 |
| Linum usitatissimum | AJ0069578 | | | | Jain, 1998 |
| Asclepias syriaca | U60277 | 59.2 | 76.3 | 76.8 | Cahoon et al., 1997 |
| Olea europaea | U58141 | 69.9 | 84.7 | 86.3 | Baldoni et al., 1996 |
| Pelargonium xhortorum | U40344 | 62.7 | 77.9 | 79.1 | Schultz et al., 1996 |
| Persea americana | AF116861 | | | | Madi and Pruskey, 1999 |
| Oryza sativa | D38753 | 67.7 | 82.1 | 84.9 | Akagi et al., 1995 |
| Ricinus communis | M59857 | 77.6 | 89.4 | 90.7 | Shanklin et al., 1991 |
| Sesamum indicum | D42086 | | | | Yukawa et al., 2000 |
| Solanum commersonii | X78935 | 71.5 | 87.6 | 87.6 | GenBank X78935 |
| Simmondsia chinensis | M83199 | 69.9 | 86.1 | 89.0 | Sato et al., 1992 |
| Spinacia oleracea | X62898 | 71.0 | 86.2 | 88.2 | Nishida et al., 1992 |
| Solanum tuberosum | M91238 | 70.8 | 84.8 | 86.6 | Taylor et al., 1992 |
| T. alata pTAD2 | U07597 | 69.6 | 86.2 | 88.5 | Cahoon et al., 1994 |
| T. alata pTAD3 | U07605 | 70.5 | 85.9 | 87.4 | Cahoon et al., 1994 |
| T. alata Δ6-desaturase | U09269 | 65.0 | 75.0 | 77.8 | Cahoon et al., 1994 |

EXAMPLE 7

Organisation of the Δ9 Stearoyl-ACP Desaturase Gene Family

We analysed the organisation of the cotton Δ9 stearoyl-ACP desaturase gene family by Southern blot hybridisation of cotton genomic DNA samples, using labelled DNA probes consisting of the 3'-UTR of the ghSAD-1clone, or alternatively, the entire coding region of ghSAD-1, under high stringency hybridisation conditions, essentially as described herein above.

Genomic DNAs tested were from G. barbadense, G. hirsutum (cv Deltapine-16), G. hirsutum (cv Siokra), G. herbaceum, G. raimondii. The cotton DNAs were digested with EcoRI, HindIII, or XbaI prior to electrophoresis, because these enzymes do not have sites in the region covered by the probe DNA sequences.

Figure 4B:
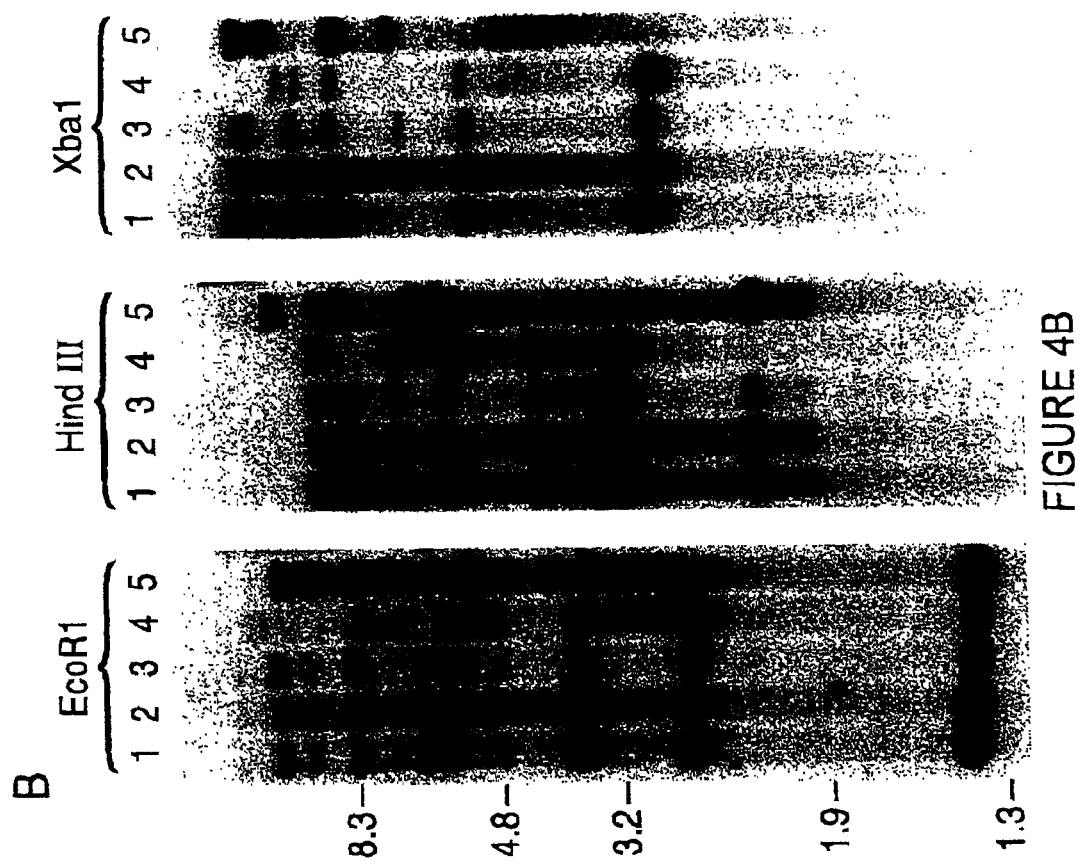
FIG. 4 is a copy of a photographic representation of a Southern blot hybridisation of cotton genomic DNA, probed with nucleotide sequences derived from the Δ9 stearoyl-ACP desaturase cDNA clone ghSAD-1. Panel (A) shows the genomic DNA fragments hybridising to the 3'-UTR of ghSAD-1. Panel (B) shows the genomic DNA fragments hybridising to the coding region of ghSAD-1. Lane 1, *G. barbadense* DNA; Lane 2, *G. hirsutum* cv Deltapine-16 DNA; Lane 3, *G. hirsutum* cv Siokra DNA; Lane 4, *G. herbaceum* DNA; and Lane 5, *G. raimondii* DNA.

As shown in FIG. 4-A, the ghSAD-1-specific probe consisting of the 3'-UTR of ghSAD-1 detected two strong bands in each of the allotetraploids, and a single strong band in each of the two diploids, for all restrction enzyme digests tested. These data suggest the presence of two copies of the ghSAD-1 gene in each of the tetraploids, and only one copy in each of the diploids, consistent with the ploidy of each cotton.

In contrast, the entire ghSAD-1 coding region detected a complex pattern in cotton DNA, consisting of multiple fragments in each of the three enzyme digests (FIG. 4-B). These data clearly indicate that the Δ9 stearoyl-ACP desaturase is encoded by a multigene family which is composed of 6–8 genes, or gene copies, in diploid cotton genomes, and probably twice as many in the allotetraploid cottons, G. barbadense and G. hirsutum.

Moreover, the allotetraploid cottons tested, G. barbadense, and two G. hirsutum cultivars, share highly conserved restriction fragment length patterns, with only minor differences. However, the two diploid species are distinctively different. It was estimated that the A- and D-genomes of cotton diverged from a common ancestor 6–11 million years ago, whereas the divergence of the two tetraploids occurred much more recently, about 1–2 million years ago (Endrizzi et al., 1985; Wendel and Albert, 1992). Among the currently existing diploid cottons, the A-genome diploid species G. herbaceum, and the D-genome diploid species G. raimondii, are regarded as being most-closely related to the progenitor species of the modern tetraploid cotton (Endrizzi et al., 1985).

In this respect, of the two EcoRI fragments in each of the three tetraploids (lanes 1–3 of FIG. 4-A), the lower EcoRI fragment appears to be the same as that in the A-genome diploid G. herbaceum (lane 4 of FIG. 4-A), suggesting that this gene is derived from the A-genome. Similarly, the upper EcoRI fragment in each of the three tetraploids (lanes 1–3 of FIG. 4-A) corresponds to the fragment present in the D-genome diploid G. raimondii (lane 5 of FIG. 4-A), suggesting that this gene is derived from the D-genome. Even among the complex patterns in FIG. 4-B, some hybridising fragments present in the tetraploid cottons are identical to those of the diploid species tested, suggesting an assignment of subgenomic origins of the tetraploid genes.

In summary, data presented in FIG. 4 suggest that the cotton Δ9 stearoyl-ACP desaturase gene, ghSAD-1, is a member of a highly-conserved multi-gene family in tetraploid cotton, comprising at least 6–8 genes, or gene copies, per diploid genome, and possibly derived from the A and D genomes.

EXAMPLE 8

Isolation and Cloning of cDNAs Encoding Cotton Fatty Acid Δ12-Desaturase (Oleoyl-PC Δ12 Desaturase)

A nucleotide sequence comprising a cotton fatty acid Δ12-desaturase (oleoyl-PC Δ12 desaturase) gene was isolated essentially as described by Liu, Q., et al. (1999).

Briefly, a heterologous probe, consisting of the entire coding region of the B. juncea microsomal ω-6 desaturase, was used to screen the cottonseed cDNA library described hereinabove. Twelve positive-hybridising plaques were identified in a primary screen of approximately $1 \times 10^6$ pfu, eleven of which were purified by two further consecutive screenings, and their cDNA inserts characterised by nucleotide sequence determination, essentially as described hereinabove.

Restriction enzyme mapping, and partial DNA sequence analysis, indicated that the rescues cDNA clones harboured the same insert, designated ghFAD2-1.

Analyses of the nucleotide sequences of ghFAD2-1 revealed that it was truncated at the 5' end. To obtain the missing 5' end of ghFAD2-1, a PCR approach using crude DNA exacts from λ cDNA library as DNA template was employed. A sample of the bacteriophage containing the cotton seed cDNA library (approximately $1 \times 10^9$ pfu) was extracted by phenol/chloroform and chloroform, followed by ethanol precipitation. The pellet was air-dried and dissolved in 20 μl $H_2O$. The 5'-end of the cDNA was amplified using a cDNA-specific primer, designated Δ12A4, in combination with the forward primer (i.e. the primer which anneals to the forward priming site in the pBluescript vector), or alternatively, the reverse primer (i.e. the primer which anneals to the reverse priming site in the pBluescript vector), that bind in the region close to the 5'- and 3'-EcoRI cloning sites of that vector, as follows:

```
Primer Δ12A4 (SEQ ID NO: 10):
5'-GCATAGGTCATGGACCACGT-3';

Forward Primer (SEQ ID NO: 11):
5'-GTAAAACGACGGCCAGT-3';

Reverse Primer (SEQ ID NO: 12):
5'-GGAAACAGCTATGACCATG-3'.
```

A 50 μl PCR reaction mixture contained 200 μM dNTP, 1×PCR buffer, 20 pmol of each of the primers, 5 μl of cDNA library extract, and 1 unit of Taq polymerase. PCR was conducted by heating to 94° C. for 2 min, followed by 30 cycles, at 94° C. for 45 seconds, 57° C. for 1 min, and 72° C. for 1 min. After the last cycle, reactions were incubated for 10 min at 72° C. The PCR product was purified by Wizard PCR Preps DNA Purification System (Promega) and cloned into T-vector (Promega) according to manufacturer's instructions.

The nucleotide sequence of one amplified clone matched the 5'-terminal sequence of the original cDNA clone. The nucleotide sequences of the original clone and the amplification product were joined (SEQ ID NO: 3), to produce a full-length cDNA of 1411 bp in length, encoding a polypeptide of 386 amino acids in length (SEQ ID NO: 4; and FIG. 5).

A second cDNA encoding a cotton microsomal ω-6 desaturase, of 1422 nucleotides in length, has also been isolated and is designated ghFAD2-2 (Accession No. Y10112). The nucleotide sequence and deduced amino acid sequence of ghFAD2-2 is presented in FIG. 6 (SEQ ID NO: 5). The ghFAD2-2 cDNA clone is divergent from ghFAD2-1 in so far as it possesses unique 5'- and 3'-UTRs, indicating that these genes have evolved independently since their divergence from a common ancestral gene. Gene-specific probes, based on the unique 3'-UTR sequences of ghFAD2-1 and ghFAD2-2, have been used in Southern and Northern blot analyses, to determine gene organisation and expression, respectively.

Figure 7:
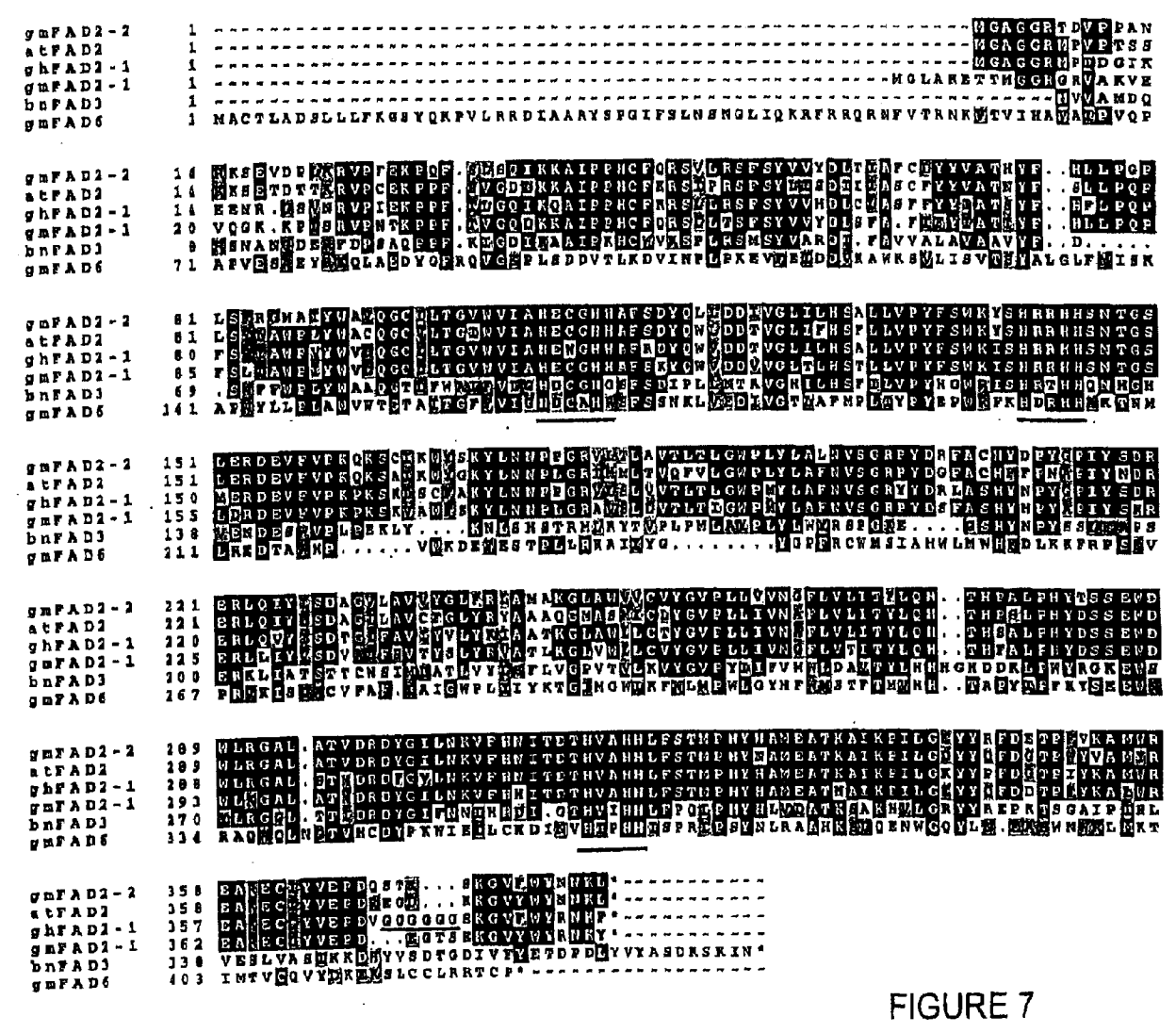

As shown in FIG. 7, the alignment of the microsomal ω-6 desaturases from cotton (ghFAD2-1 and ghFAD2-2), soybean (gmFAD2-1, FAD2-2), A. thaliana (atFAD2), and the microsomal ω-3 desaturase from B. napus (bnFAD3), and the plastid ω-6 desaturase from soybean (gmFAD6), reveals a high conservation between the microsomal ω-6 desaturases. Moreover, the seed-specific proteins of cotton (ghFAD2-1) and soybean (gmFAD2-1) are most closely-related to each other, whilst cotton ghFAD2-2 is most similar to the constitutively-expressed soybean protein, gmFAD2-2. Significantly lower sequence identity occurs between the B. napus microsomal w-3 desaturase protein, bnFAD3, and any of the microsomal ω-6 desaturases. The plastid ω-6 desaturase, gmFAD6, remains the least similar sequence to all the microsomal desaturase amino acid sequences. This analysis confirms previous studies (Yadav et al., 1993).

The three histidine boxes which were shown to be highly conserved in all membrane-bound desaturases (Schmidt et al., 1994), were also observed in the G. hirsutum microsomal ω-6 desaturases, ghFAD2-1 and ghFAD2-2. As shown in FIG. 7, among the five microsomal ω-6 desaturases listed, the deduced consensus amino acid residues for the three histidine box motifs are as follows:

(i)   His-Glu-(Cys/Trp)-Gly-His-His [i.e. HE(C/W)GHH] (SEQ ID NO: 26);

(ii)  His-Arg-Arg-His-His (i.e. HRRHH) (SEQ ID NO: 27);

and (iii) His-Val-Ala-His-His (i.e. HVAHH) (SEQ ID NO: 28).

The general sequence for the histidine box motif is His-Xaa $_{(2-3)}$-His-His (SEQ ID NO: 29 and SEQ ID NO: 30).

Similar to other microsomal ω-6 desaturases, the deduced protein sequence of the ghFAD2-1 clone lacks a recognisable signal sequence for targeting to the endoplasmic reticulum (ER), and it is possible that the gene products may be translocated into the ER post-translationally, as in the case of the rat liver Δ9 stearoyl-CoA desaturase (Thiede et al., 1985). A lysine-rich carboxyl-terminal motif, present in the A. thaliana FAD3 enzyme, which has been suggested to represent the retention signal of integral membrane proteins in the ER (Jackson et al., 1990), is not present in the cotton microsomal ω-6 fatty acid desaturases.

Near the C-terminal of the ghFAD2-1 ORF there exists a stretch of six continuous glycine residues, which distinguish this amino acid sequence from other microsomal ω-6 desaturases (FIG. 7).

Hydropathy plot analysis of the amino acid sequence encoded by ghFAD2-1 reveals six transmembrane helices. Interestingly, the three histidine boxes proposed to be iron-binding sites during catalysis, are not located in the region of transmembrane helices.

EXAMPLE 9

Figure 8:
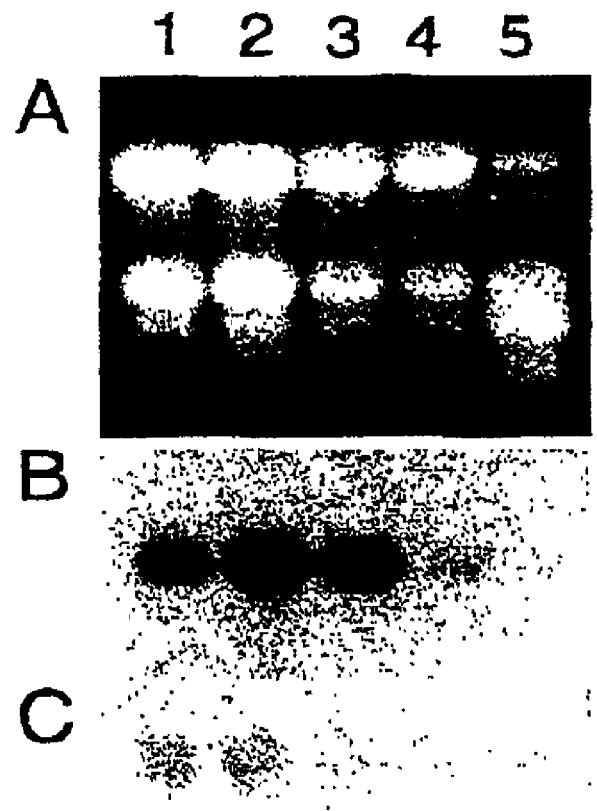
FIG. 8 is a schematic representation of a Northern blot hybridisation of developing cotton seed embryos, and cotton leaf tissue. Panel (A) shows an ethidium bromide-stained RNA gel. Panel (B) shows the hybridisation signal obtained using a [$\alpha$-$^{32}$P]dCTP-labelled ghFAD2-1-specific probe. Panel (C) shows the hybridisation signal obtained using a [$\alpha$-$^{32}$P]dCTP-labelled ghFAD2-2-specific probe. Lanes 1–4 represent RNA samples isolated from embryos at 25, 30, 36, and 45 DAA, respectively. Lane 5 represents RNA isolated from young leaves.

Expression of the ghFAD2-1 and ghFAD2-2 Genes During Cotton Seed Development Northern hybridisations of a labelled ghFAD2-1 probe to cotton RNA were carried out under the same conditions as described hereinabove. As shown in FIG. 8B, ghFAD2-1 expression was detected in the earliest embryos sampled (i.e. at 25 DAA). The detectable level of mRNA rapidly increased during embryo development, with the highest expression being at 30 DAA. Significantly lower amounts of transcripts were detected in the embryos nearer maturity, at 45 DAA or later. No transcripts of the ghFAD2-1 were detectable in cotton leaf tissues. The pattern of mRNA accumulation data presented herein suggest that the ghFAD2-1 gene is expressed during the period of maximum storage lipid synthesis and accumulation in cotton, consistent with the increased linoleic acid accumulation during the same period. Accordingly, these data indicate that the ghFAD2-1 gene possibly plays a major role in the desaturation of cottonseed oil.

In contrast, very low expression of ghFAD2-2 is detected in both leaf and embryo tissues (FIG. 8C). These data suggest that the ghFAD2-2 gene contributes in only a minor way to total fatty acid Δ12-desaturase activity in cotton seed, and, as a consequence, expression of this gene is minor contributing factor to the desaturation of cotton seed oil.

EXAMPLE 10

Organisation of the Oleoyl-PC Δ12 Desaturase Gene Family

We analysed the organisation of the cotton oleoyl-PC Δ12 desaturase gene family, by Southern blot hybridisation of cotton genomic DNA samples, using labelled DNA probes consisting of the 3'-UTR of the ghFAD2-1 and ghFAD2-2 clones, or alternatively, the entire coding regions of these cDNA clones, under high stringency hybridisation conditions, essentially as described hereinabove.

Genomic DNAs tested were from G. barbadense, G. hirsutum (cv Deltapine-16), G. hirsutum (cv Siokra), G. herbaceum, G. raimondii and G. robinsonii. The cotton DNAs were digested with EcoRI, and HindIII.

Figure 9A:
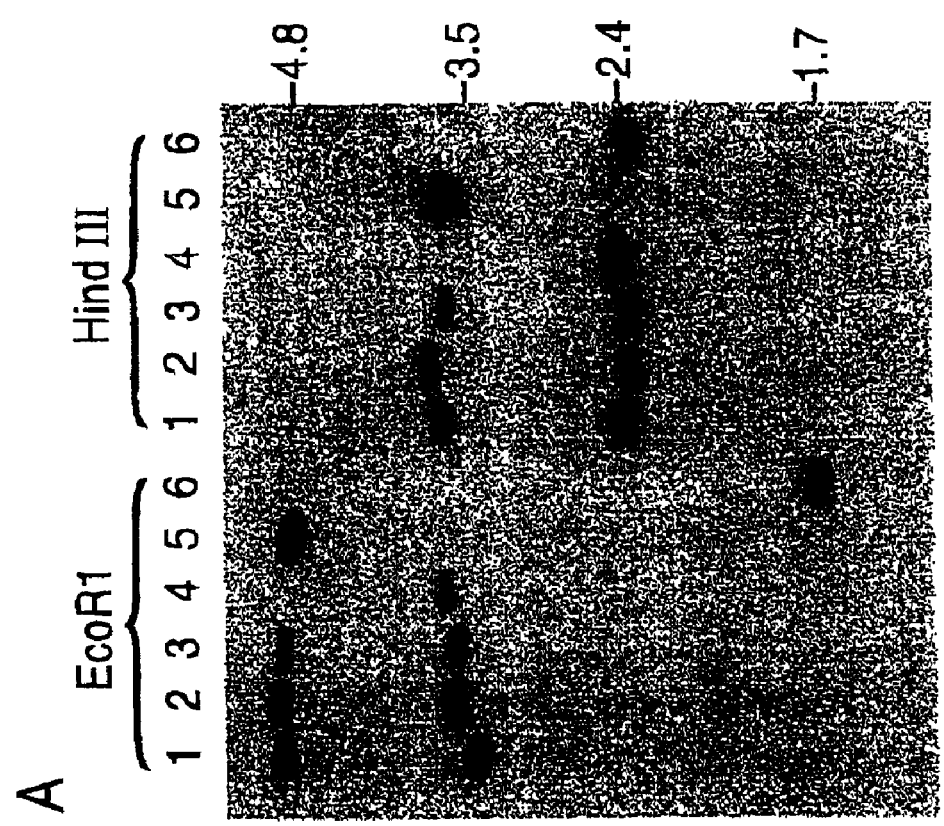
FIG. 9 is a copy of a photographic representation of a Southern blot hybridisation of cotton genomic DNA, probed with nucleotide sequences derived from the oleoyl-PC $\Delta$12 desaturase cDNA clone ghFAD2-1-Panel (A) shows the genomic DNA fragments hybridising to the 3'-UTR of ghFAD2-1. Panel (B) shows the genomic DNA fragments hybridising to the 3'-UTR of ghFAD2-2. Panel (C) shows the genomic DNA fragments hybridising to the coding region of ghFAD2-1. Lane 1, *G. barbadense* DNA; Lane 2, *G. hirsutum* cv Deltapine-16 DNA; Lane 3, *G. hirsutum* cv Siokra DNA; Lane 4, *G. herbaceum* DNA; Lane 5, *G. raimondii* DNA; and Lane 6, *G robinsonii*.
Figure 9C:
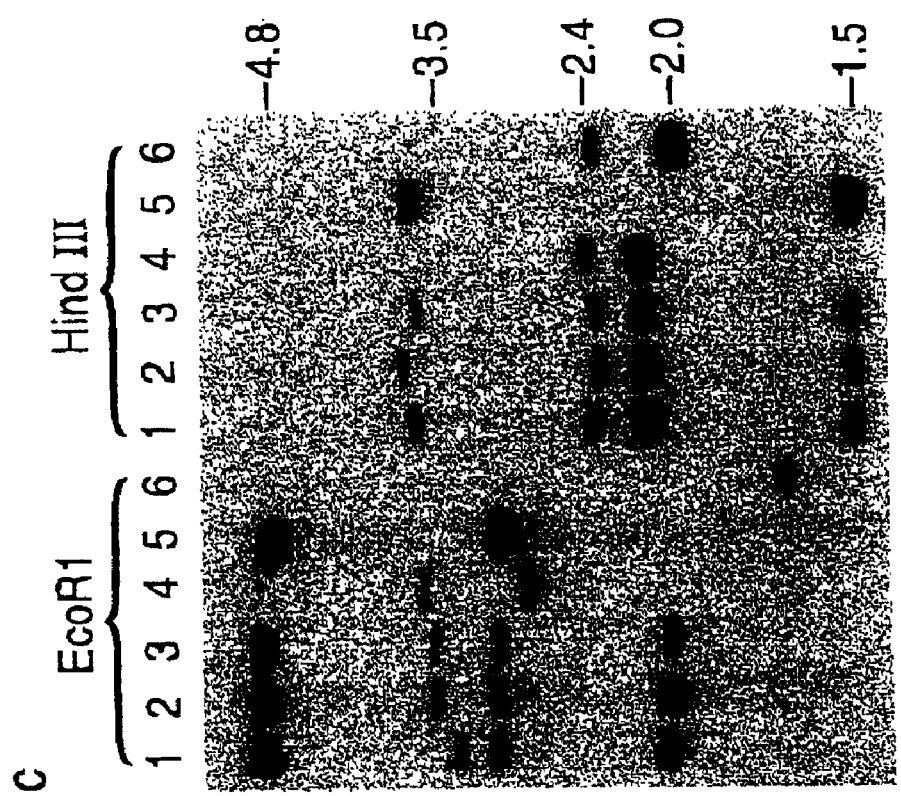

FIG. 9-A represents a Southern blot hybridised to a ghFAD2-1-specific fragment based on the sequence of the 3'-UTR of ghFAD2-1. In both EcoRI and HindIII digests, there are two distinct fragments in tetraploids (lane 1–3), one of which is present in each of the diploids (lane 4–6). Of the two fragments present in the tetraploid species, the smaller fragment has a similar size as the fragement of G. herbaceum (lane 4), whilst the larger fragment is similar to that of G. raimondii (lane 5). A single fragment is also present in G. robinsonii, the C-genome diploid species.

FIG. 9-B represents a Southern blot using the more conserved coding region of ghFAD2-1 as a probe. Five EcoRI fragments, and four HindIII fragments are detectable in tetraploid cottons (lanes 1–3), whilst only two fragments are discernible in the diploids (lanes 4–6). However, one HindIII fragment (the third fragment from top in lanes 1–4; and the second fragment in lane 6) appears to be at least twice as strong as the other fragments, and presumably contains multiple copies of the gene. Therefore, we suggest that there are at least five members of the microsomal cow desaturase gene family in each of the tetraploid cotton species. Furthermore, it appears that the A-genome diploid species, G. herbaceum (lane 4), has at least three genes, and the D-genome diploid species, G. raimondii (lane 5), has two genes, in this gene family.

The inconsistent fragment patterns obtained for EcoRI-digested and HindIII-digested G. robinsonii DNA (lane 6) may be a consequence of incomplete digestion of the G. robinsonii genomic DNA. In this respect, the pattern of HindIII fragements observed for G. robinsonii are similar to those observed fro the A-genome diploid species.

In summary, Southern blot analyses indicate that there are at least five closely related microsomal ω-6 desaturase genes in each of two tetraploids, G. barbadense and G. hirsutum. The conservation of polymorphic restriction fragment patterns in tetraploid genomes and those representing their putative progenitors was sufficient to allow the assignment of each of the fragments in allotetraploid to their respective subgenomes. We estimate that, for tetraploid cotton, at least three genes (copies) were derived from the A-genome, and at least two genes may be derived from the D-genome. The ghFAD2-1 gene appears to be a single-copy gene in diploid cotton species, indicating that a gene duplication probably did not occur in cotton.

The promoter sequence of the cotton ghFAD2-1 gene is provided in SEQ ID NO. 7. In this respect, SEQ ID NO: 7 contains sufficient nucleotide sequence to confer expression on a structural gene to which it is operably connected in the cottonseed. In particular, the 5006 nucleotides of SEQ ID NO: 7 includes 3784 nucleotides upstream of the transcription start site of the FAD2 gene (position 3785), the first intron of the gene (nucleotides 3889 to 4998) and the entire 5'-untranslated region (UTR) of the FAD2 gene (nucleotides 3785 to 5006).

EXAMPLE 11

Gene Constructs for Silencing Fatty Acid Biosynthesis Genes

Gene constructs were produced to facilitate a reduction in the expression of the endogenous cotton fatty acid Δ9-desaturase gene (ghSAD-1), and the endogenous cotton fatty acid Δ12-desaturase gene (ghFAD2-1). The gene constructs used the ghSAD-1 and ghFAD2-1 cDNA sequences, in the antisense orientation, or as inverted-repeat sequences having self-complementarity.

Construction of the pBI-Lectin Binary Plasmid

To confer seed-specific expression on gene fragments comprising antisense and inverted-repeat sequences of these genes, the soybean lectin promoter was used. A NotI adaptor sequence having a SmaI site was produced by annealing oligonucleotides having the nucleotide sequences, 5'-GGCCCGGG-3' (SEQ ID NO: 13) and 5'GGCCCCCG-3' (SEQ ID NO: 14) using standard conditions. This adaptor was ligated into the NotI site of the plasmid pGLe-10 (Cho, 1995), containing the soybean lectin promoter and terminator sequences. The plasmid was subsequently digested using EcoRI and HindIII, and a fragment comprising both the lectin promoter and lectin terminator sequences was isolated, and ligated into pBl121 that had been digested using EcoRI and HindIII, thereby replacing the CaMV 35S-GUS-NOS chimeric gene of pBl121 with the soybean lectin promoter/terminaotr-containing fragment. The components of this modified pBl-Lectin binary vector is illustrated in FIG. 10.

Gene fragments were cloned into the SmaI site of the pBl-Lectin binary vector, which site was present in the NotI adaptor. To facilitate such cloning steps, the pBl-Lectin binary vector was predigested with SmaI and dephosphorylated using calf intestinal phosphatase (CIP) enzyme (Pharmacia).

Fatty AcidΔ9-desaturase Antisense Gene Constructs

Antisense gene constructs targeted against the Δ9-desaturase gene comprise the full length ghSAD-1 cDNA clone, cloned in the antisense orientation as a blunt-ended NotI fragment, into the SmaI site of the pBl-Lectin binary vector.

Fatty AcidΔ9-desaturase Inverted Repeat Gene Constructs

An inverted repeat of the 5'-terminal region of the cotton ghSAD-1 clone was produced by PCR amplification, according to the following description. A fragment of approximately 500 bp in length derived from the of 5'-end of the cotton ghSAD-1 cDNA clone was amplified using the following primers:

```
(i)  Primer 9s1 (SEQ ID NO: 15):
     5'-TTTTAATGCCATCGCCTCG-3'; and (ii) Primer 9a1 (SEQ ID NO: 16):
     5'-CTTCAGCAGTCCAAGCCCTG-3'.
```

The amplified gene fragment was cloned into Teasy® vector (Promega). One clone having the amplified gene fragment in a desired orientation was selected, and the gene fragment was released by digestion of the plasmid DNA using SalI and ApaI. Concurrently, the full-length ghSAD-1 cDNA clone having the desired orientation was amplified by PCR, using the reverse primer present in the pBluescript vector, and the 9a1 primer supra, and this clone was linearised by digestion with the enzymes SalI and ApaI The 500 bp SalI/ApaI fragment, containing only the 5'-end of the cotton ghSAD-1 cDNA clone, was ligated to the linearised full-length cDNA in pBluescript. This ligation produced a partial inverted repeat sequence comprising the full-length ghSAD-1 clone extended at its 3'-end by 500 bp of the 5'-end nucleotide sequence in the reverse orientation. Accordingly, the ligation product contained a perfect inverted repeat of the 500 bp 5'-end nucleotide sequence. To release this inverted repeat sequence, the ligation product was digested using the restriction enzymes ApaI and XbaI. The inverted repeat sequence was then end-filled using Klenow fragment, and the blunt-ended fragment was ligated into the SmaI site of the pBl-Lectin binary vector, between the lectin promoter and lectin terminator sequences.

Fatty AcidΔ12-desaturase Antisense Gene Constructs

The full-length cDNA ghFAD2-1 clone was amplified by PCR, using a pair of amplification primers, as follows:

```
Primer 12s1 (SEQ ID NO: 17):
5'-CCTGGCGTTAAACTGCTTTC-3'; and

Primer 12a2 (SEQ ID NO: 18):
5'-CCATATAGTTTATTAATATAACAC-3'.
```

The amplification product was cloned into either the Teasy® vector, or alternatively, the T® vector (Promega). The full-length ghFAD2-1 insert was released from the Teasy® vector by digestion with NotI, end-filled using Klenow fragment, and ligated into the SmaI site of the pBl-Lectin binary vector, between the lectin promoter and lectin terminator sequences. A clone comprising the ghFAD2-1 cDNA clone in the antisense orientation was selected by nucleotide sequence determination.

Fatty Acid Δ12-Desaturase Inverted Repeat Gene Constructs

An inverted repeat of the 5'-terminal region of the cotton ghFAD2-1 clone was produced by PCR amplification, according to the following description.

The full-length ghFAD2-1 cDNA in T® vector with the desired orientation was selected using the forward primer on the T vector, and primer 12a1 (SEQ ID NO: 19; 5'-TATGTTGCAAGTAGGTGATC-3'). Then it was linearized by digestion of the plasmid DNA using NotI (the T® vector contains only one NotI site in the polylinker region).

Concurrently, a fragment of approximately 850 bp in length derived from the of 5'-end of the cotton full-length ghFAD2-1 cDNA clone was amplified by PCR, using the primers 12s1 and 12a1, and the amplified DNA was cloned into the Teasy® vector. The amplified fragment was digested using the enzyme NotI.

The 850 bp NotI fragment, containing only the 5'-end of the cotton ghFAD2-1 cDNA, was ligated to the NotI site in the T® vector containing the full-length ghFAD2-1 cDNA clone. This ligation produced a partial inverted repeat sequence comprising the full-length ghFAD2-1 clone extended at its 3'-end by about 850 bp of the 5'-end nucleotide sequence, in the reverse orientation. Accordingly, the ligation product contained a perfect inverted repeat of about 850 bp of 5'-end nucleotide sequence. To release this inverted repeat sequence, the ligation product was digested using the restriction enzymes ApaI and SacI. The inverted repeat sequence fragment was then end-filled using Klenow fragment, and the blunt-ended fragment was ligated into the SmaI site of the pBl-Lectin binary vector, between the lectin promoter and lectin terminator sequences.

An additional Δ12-desaturase gene silencing construct was produced that comprised an inverted-repeat produced from about 92 bp of the 5'-UTR region of the genomic ghFAD2-1 gene (SEQ ID NO: 7). In this gene construct, the 5'-UTR of the ghFAD2-1 gene was separated by nucleotide sequence from the first intron of the ghFAD2-1 gene. The inverted repeat sequence was placed operably in connection with regulatory sequences from the ghFAD2-1 gene (i.e. sequences derived from SEQ ID NO: 7). This gene construct is referred to hereinafter as an "intron-interrupted UTR inverted-repeat gene construct".

To produce the intron-interrupted UTR inverted-repeat gene construct, nucleic acid was amplified by PCR from *G. hirsutum* cv Coker 315 genomic DNA, using the following amplification primers:

(i) PITSal (SEQ ID NO: 20):
    5'-ACGCGTCGACGTGTGTTACAAAATGGACCGAA-3';

and (ii) PITBam (SEQ ID NO: 21):
    5'-CGCGGATCCGCTGGCTGGACACGCAAGAAGCA-3'.

Nucleotide residues of the primer PITSal supra shown in bold typeface correspond to nucleotides 2569 to 2592 of SEQ ID NO: 7. This primer has a 5'-localized SalI site. Nucleotide residues of the primer PITBam supra shown in bold typeface are complementary to nucleotides 4981 to 5003 of SEQ ID NO: 7. This primer has a 5'-localized BamHI site, which is incorporated into the 3'-end of the amplified DNA. Accordingly, DNA amplified using this primer pair comprises a 5'-SalI site and a 3'-BamHI site to facilitate sub-cloning.

The amplified gene fragment included approximately 1.2 kb of nucleotide sequence upstream of the transcription start site of the ghFAD2-1 gene. This is sufficient sequence to function as a promoter in cottonseed. The amplified DNA fragment also includes the entire 5'-UTR and first intron of the ghFAD2-1 gene.

The amplified DNA fragment was digested with SalI and BamHI, and cloned directionally into the corresponding sites of the vector pBl101.2, to yield an intermediate ghFAD2-1 promoter-intron construct.

To produce the inverted repeat within the 5'-UTR, about 92 bp of 5'UTR sequence from the ghFAD2-1 gene, without intron sequence, was amplified from cottonseed cDNA, using the following PCR primers:

(i)  Usac (SEQ ID NO: 22):
     (5'-CGAGCTCCCCCTCCGCTCCATACCACT-3'); and (ii) Ubam (SEQ ID NO: 23)
     (5'-CGCGGATCCGCTGGCTTTAAAGAAAGCAGTT-3').

Nucleotide residues of the primer Usac supra shown in bold typeface correspond to nucleotides 3796 to 3820 of SEQ ID NO: 7. This primer has a 5'-localized SacI site. Nucleotide residues of the primer Ubam supra shown in bold typeface are complementary to nucleotides 3872 to 3888 of SEQ ID NO: 7. This primer has a 5'-localized BamHI site, which is incorporated into the 3'-end of the amplified DNA. Accordingly, DNA amplified using this primer pair comprises a 5'-SacI site and a 3'-BamHI site to facilitate sub-cloning into the intermediate ghFAD2-1 promoter-intron construct.

The amplified DNA fragment was cloned, in the inverted orientation relative to its orientation in the ghFAD2-1 gene, downstream of the intron in the intermediate ghFAD2-1 promoter-intron construct. Accordingly, the final intron-interrupted UTR inverted-repeat gene construct thus comprised the following features:

(i) nucleotide residues 2569–3785 of SEQ ID NO: 7 comprising sequences sufficient to confer expression in cottonseed and the transcription start site of the ghFAD2-1 gene;
(ii) a part of the 5'-UTR of the ghFAD2-1 gene corresponding to nucleotides 3785–3888 of SEQ ID NO: 7;
(iii) the first intron of the ghFAD2-1 gene corresponding to nucleotides 3889–4998 of SEQ ID NO: 7 placed downstream of (ii);
(iv) a part of the 5'-UTR of the ghFAD2-1 gene corresponding to nucleotides 4999–5003 of SEQ ID NO: 7 placed downstream of (iii); and
(v) a part of the 5'-UTR of the ghFAD2-1 gene corresponding to nucleotides 3796–3888 of SEQ ID NO: 7 placed downstream of (iv) and in the inverted orientation relative to (ii).

EXAMPLE 12

Transformation of Cotton Plants

Transgenic cotton plants (*G. hirsutum* cv. Coker 315) were generated by *Agrobacterium*-mediated infection, and selection on medium containing kanamycin sulphate, by a modification of the method described by Cousins et al. (1991)

Briefly, cotton seedlings were germinated aseptically on Murashige and Skoog (MS) medium (Murashige and Skoog, 1962), solidified using phytagel (Sigma). Seedlings were maintained under low light conditions at 28° C. Callus was initiated from cotyledon explants of 10–14 day old seedlings, on callus initiation medium [MS macro and micro elements; B5 vitamins (Gamborg, 1968); 100 mg/l myo-inositol; 30 g/l glucose; 0.2 mg/l 2,4-dichlorophenoxyacetic acid (2,4-D); 0.1 mg/l kinetin; and 0.93 g/l magnesium chloride], solidified using 2 g/l phytagel.

Explants derived from about 20 seedlings was infected with *A. tumefaciens* strain AGL1 which had been transformed with the relevant gene construct (supra) by standard electroporation. Following 2 days of cocultivation in the presence of *A. tumefaciens*, the cotton explants were transferred to MS medium containing 0.1 mg/l 2,4-D, 0.1 mg/l kinetin, 50 mg/l kanamycin sulphate, and 250 mg./l cefotaxime, and incubated at 28° C. for six weeks.

Healthy calli were then transferred to MS medium containing 5 mg/l 6-(γ,γ-dimethylallylamino)-purine (2ip), 0.1 mg/l naphthalene acetic acid (NAA), 25 mg/l kanamycin, and 250 mg/l cefotaxime for a second selection period of six weeks at 28° C.

Developing embryos were maintained and germinated into plantlets as described by Cousins et al. (1991). Briefly, following the second selection period, the central soft parts of the calli were transferred onto solidified MS medium, without addded phytohormone or antibiotic, to initiate embryogenesis. Embryogenic calli formed after about six to ten weeks of incubation at 28° C. The embryogenic calli were transferred to embryo development medium comprising MS medium containing an additional 1.9 g/l potassium nitrate. Embryos continue to develop on this medium, and can be removed, and germinated on SH medium (Stewart, 1977) solidified with phytagel, to produce transgenic cotton plantlets.

Transgenic cotton plantlets (T1 generation) were transferred to soil, and maintained in a glasshouse, once leaves and roots developed.

EXAMPLE 13

Characterisation of Transgenic Cotton Plants

No obvious phenotypic differences were observed between the transgenic lines and isogenic non-transformed control plants. Genomic DNA was prepared from young leaves of regenerated cotton (T1) plants, essentially as described herein above.

The presence of the respective gene silencing transgene in each cotton plant was determined by PCR, using genomic DNA as a template, and the following primers:

```
Primer 3Lec-s1 (SEQ ID NO: 24):
5'-CATGTGACAGATCGAAGGAA-3';

and

Primer3Lec-a1 (SEQ ID NO: 25):
5'-ATCTAATTATTCTATTCAGAC-3'.
```

This process amplifies an approximately 300 bp DNA fragment comprising the transcriptional terminator of the soybean lectin gene. Accordingly, amplification only occurs from plant DNA containing the introduced chimeric genes. Further confirmation that the amplified fragment was indeed the soybean lectin terminator was obtained by performing Southern blot hybridization analysis, using the isolated soybean lectin terminator as a probe, as described herein above.

To confirm the presence of the fatty acid biosynthesis antisense and/or inverted repeat sequences in the transgenic cotton plants, genomic DNA derived from each putative transgenic plant was digested with HindIII, separated on a 0.7% (w/v) agarose gel, blotted onto a Hybond-N+ nylon membrane, and probed with an [$\alpha$-$^{32}$P]dCTP-labelled gene-specific DNA fragment The conditions of hybridization and the following washing was the same as described herein-above. Data presented in Table 6 indicate the copy number of transgenes in some representative lines that were analyzed.

TABLE 6

Copy number of transgenes in T1 cotton plants

| Transgene copy number | Plant line | | Plant line | |
|---|---|---|---|---|
| | $\Delta$9-desaturase inverted repeat construct | $\Delta$9-desaturase antisense construct | $\Delta$12-desaturase inverted repeat construct | $\Delta$12-desaturase antisense construct |
| 1 | 95–6 | 9A–17 | 125–21 | 12A–4 |
| | 95–37 | 9A–38 | 125–23 | 12A–11 |
| | 95–40 | 9A–148 | 125–26 | 12A–43 |
| | 95–43 | 9A–163 | 125–27 | 12A–45 |
| | 95–49 | 9A–183 | 125–31 | 12A–48 |
| | 95–55 | | 125–33 | 12A–59 |
| | 95–70 | | 125–50 | 12A–73 |
| | 95–72 | | 125–60 | 12A–74 |
| | 95–75 | | 125–62 | 12A–130 |
| | 95–79 | | 125–82 | |
| | 95–87 | | 125–92 | |
| | 95–146 | | 125–103 | |
| | | | 125–117 | |
| | | | 125–128 | |
| 2 | 95–31 | 9A–89 | 125–2 | 12A–41 |
| | 95–91 | 9A–127 | 125–54 | 12A–111 |
| | 95–112 | | 125–58 | |
| | 95–120 | | 125–81 | |
| | 95–136 | | 125–96 | |
| 3 | 95–21 | 9A–192 | 125–12 | 12A–60 |
| | 95–22 | | 125–32 | 12A–82 |
| | 95–51 | | 125–79 | 12A–124 |
| | 95–61 | | 125–114 | |
| | 95–80 | | 125–125 | |
| | 95–96 | | | |
| 4 | 95–65 | 9A–118 | 125–10 | 12A–117 |
| 5 | 95–23 | 9A–119 | 125–83 | |
| | 95–57 | 9A–189 | | |
| | 95–150 | | | |
| 6 | | 9A–57 | 125–87 | |
| 7 | | | | 12A–68 |
| 8 | | | 125–121 | |
| 9 | | | 125–120 | |
| 10 | | | | 12A–34 |
| 12 | | | | 12A–56 |

EXAMPLE 14

Characterisation of Oils in Transgenic T2 Seed Containing Inverted Repeats of a Fatty Acid $\Delta$9-Desaturase (Stearoyl-ACP $\Delta$9-Desaturase) Gene The seeds produced by independent transgenic (T1) plants containing inverted repeats of the cotton fatty acid $\Delta$9-desaturase gene, and a non-transformed isogenic *G. hirsutum* Coker cotton, were analyzed for their fatty acid composition. Samples consisting of three pooled T2 seeds derived from a number of individual T1 plants. Fatty acid methyl esters were prepared as described by Bligh and Dyer (1959). Methyl esters were separated by gas chromatography (GC), using a Hewlett-Packard 5890 gas chromatograph fitted with a fused silica capillary column (HP-FFAP, 0.53 mm×30 m). Fatty acids were identified by reference to chemical standards as described herein above.

Data are presented in Table 7. Because T1 plants were generally hemizygous for the introduced transgene, the T2 seeds were segregating for that transgene. Accordingly, the data for pooled T2 seed samples shown in Table 7 are an averaging of fatty acid levels for seeds that are either homozygous or hemizygous for the transgene, or lack the transgene altogether.

Increased Stearic Acid

Expression of the inverted repeat of the 5'-end of ghSAD-1 in cotton appeared to decrease the level of the stearoyl-ACP $\Delta$9-desaturase enzyme activity in cotton, as suggested by the elevated level of stearic acid in transgenic T2 seed. As summaried in Table 7, at least half of the total 22 individual T1 transgenic plants produced seed having elevated levels of stearic acid when compared to isogenic wild-type seed. Stearic acid was increased up to about 38% of total seed lipid (line 95–62), which represents an approximately 15-fold increase in the level of this fatty acid.

Decreased Oleic Acid

Without being bound by any theory or mode of action, the increased production of stearic acid in transgenic lines, which results from the decreased expression of the endogenous fatty acid $\Delta$9-desaturase (stearoyl-ACP $\Delta$9-desaturase) gene, is at the expense of oleic acid and linoleic acid production, because these fatty acids are all products of fatty acid $\Delta$9-desaturase (stearoyl-ACP $\Delta$9-desaturase) enzyme activity. In this respect, oleic acid was reduced, from 15% of total seed lipid in the non-transgenic cotton, to only 5.1% in the line 95-62, representing a decrease in oleic acid content of up to about 65% in the transgenic lines.

Decreased Linoleic Acid

Linoleic acid was also reduced, from 57.4% of total seed lipid in the non-transgenic, to 37.8% in line 95-62, representing a decrease in linoleic acid content of up to about 33% in the transgenic lines.

Decreased Palmitic Acid

Unexpectedly, and favourably, palmitic acid was significantly reduced in the T2 seed of transgenic cotton containing the inverted repeat of the 5'-end of ghSAD-1, particularly in those lines having increased stearic acid. In particular, the level of palmitic acid in the seed of transgenic plants was reduced to only 14.7% of total seed lipid in line 95-62, compared to 24.4% of total seed lipid for isogenic non-transformed plants. This represents a decrease in palmitic acid content of up to about 45% in the transgenic lines.

TABLE 7

Fatty acid contents of T1 transgenic cotton comprising an inverted repeat of the 5'-end of the ghSAD-1 clone

| Plant line | Fatty acid composition (%) | | | | | |
|---|---|---|---|---|---|---|
| | Palmitic | Stearic | Oleic | Linoleic | Linolenic | SDP |
| Coker control | 24.4 | 2.7 | 15.0 | 57.4 | 0.2 | 0.97 |
| 95-70 | 26.1 | 2.4 | 14.5 | 56.6 | 0.2 | 0.97 |
| 95-33 | 25.4 | 2.5 | 15.4 | 56.3 | 0.2 | 0.97 |
| 95-128 | 22.5 | 2.6 | 14.2 | 60.3 | 0.2 | 0.97 |
| 95-146 | 25.1 | 2.5 | 15.2 | 56.8 | 0.2 | 0.97 |
| 95-112 | 26.4 | 2.5 | 15.2 | 55.5 | 0.2 | 0.97 |
| 95-78 | 24.6 | 2.6 | 14.7 | 57.6 | 0.2 | 0.97 |
| 98-92 | 24.3 | 2.6 | 16.3 | 56.4 | 0.2 | 0.97 |
| 95-43 | 25.6 | 2.7 | 16.5 | 54.7 | 0.2 | 0.96 |
| 95-13 | 22.9 | 2.7 | 12.9 | 61.2 | 0.1 | 0.96 |
| 95-95 | 24.3 | 2.9 | 15.6 | 56.8 | 0.2 | 0.96 |
| 95-65 | 25.4 | 2.9 | 14.7 | 56.5 | 0.2 | 0.96 |
| 95-120 | 24.9 | 3.0 | 15.8 | 55.8 | 0.2 | 0.96 |
| 95-90 | 20.6 | 3.4 | 13.7 | 61.8 | 0.2 | 0.96 |
| 95-21 | 23.1 | 4.0 | 13.4 | 58.9 | 0.2 | 0.95 |
| 95-61 | 24.1 | 4.2 | 13.5 | 57.8 | 0.2 | 0.94 |
| 95-72 | 26.0 | 4.7 | 14.0 | 54.6 | 0.2 | 0.94 |
| 95-51 | 24.5 | 5.0 | 13.6 | 56.3 | 0.2 | 0.93 |
| 95-136 | 24.3 | 6.6 | 13.3 | 55.2 | 0.2 | 0.91 |
| 95-40 | 22.7 | 8.8 | 12.0 | 55.8 | 0.1 | 0.88 |
| 95-98 | 19.6 | 10.9 | 11.6 | 57.1 | 0.2 | 0.86 |
| 95-78 | 22.2 | 13.0 | 10.6 | 53.3 | 0.2 | 0.83 |
| 95-99 | 20.5 | 14.1 | 9.6 | 55.0 | 0.1 | 0.82 |
| 95-6 | 23.6 | 14.1 | 10.1 | 51.1 | 0.2 | 0.81 |
| 95-125 | 21.3 | 15.2 | 11.1 | 51.3 | 0.2 | 0.80 |
| 95-55 | 20.1 | 20.2 | 8.0 | 51.6 | 0.0 | 0.75 |
| 95-37 | 18.8 | 23.4 | 7.9 | 48.4 | 0.4 | 0.71 |
| 95-150 | 19.0 | 28.0 | 5.8 | 45.4 | 0.3 | 0.65 |
| 95-62 | 14.7 | 38.2 | 5.1 | 37.8 | 1.6 | 0.54 |

EXAMPLE 15

Characterisation of Oils in Transgenic Seed that is Homozygous for the Transgene Containing an Inverted Repeat of a Fatty Acid Δ9-Desaturase Gene T2 Lines that are homozygous for the introduced inverted repeat of the cotton fatty acid Δ9-desaturase gene were identified by selection. The fatty acid compositions of individual T2 seeds (15 in total), derived from several representative T1 plants that differed widely in their stearic acid content, were analyzed as described in the preceding example. Data are presented in Table 8.

It is clear that different transgenic events are associated with different levels of reduction in Δ9-desaturase activity (as indicated by SDP) and corresponding different levels of accumulation of the stearic acid substrate. This variation is explainable by different transgene copy numbers and different genomic integration locations of the transgenes. By producing a sufficient number of independent transgenics, any particular desired stearic acid content between the normal upper limit for cotton (3%) and approximately 35% can therefore be obtained (see FIG. 11).

To confirm that the observed Δ9-desaturase gene silencing was heritable, additional T2 seed, and T3 seed, were obtained from plants exhibiting the most severe silencing phenotype, in particular, the independent T1 plants having the highest levels of stearic acid in their seed and designated 95-62 and 95-150 (Table 7). The fatty acid compositions of 15 individual T2 seed and 12 individual T3 seed from these lines were determined as described in the previous example. The T2 segregation patterns were consistent with a single transgene insertion. Data presented in Table 9 demonstrate that the high level silencing observed in the T2 seeds as shown in Table 8 is inherited in the T3 generation, as evidenced by the heritability of the high stearic acid and low oleic acid and low linoleic acid and low palmitic acid phenotypes.

TABLE 8

Fatty acid composition (% of total fatty acids) of 15 individual T2 seeds from four T1 plants of cotton transformed with the Δ9-desaturase inverted-repeat gene silencing construct and from untransformed Coker control plants.

| T1 plant number | T2 seed number | Fatty acid composition (%) | | | | | |
|---|---|---|---|---|---|---|---|
| | | Palmitic | Stearic | Oleic | Linoleic | Linolenic | SDP |
| Coker control | 1 | 25.1 | 2.6 | 15.2 | 56.6 | 0.2 | 0.97 |
| | 2 | 25.1 | 2.6 | 14.9 | 57.0 | 0.2 | 0.97 |
| | 3 | 24.3 | 2.2 | 14.7 | 58.3 | 0.2 | 0.97 |
| | 4 | 25.2 | 2.5 | 14.4 | 57.4 | 0.2 | 0.97 |
| | 5 | 24.9 | 2.3 | 15.0 | 57.4 | 0.2 | 0.97 |
| | 6 | 25.2 | 2.6 | 14.8 | 56.9 | 0.2 | 0.97 |
| | 7 | 25.4 | 2.8 | 15.7 | 55.6 | 0.2 | 0.96 |
| | 8 | 23.9 | 2.7 | 15.1 | 58.0 | 0.2 | 0.96 |
| | 9 | 24.0 | 2.9 | 16.2 | 56.4 | 0.2 | 0.96 |
| | 10 | 24.4 | 2.8 | 15.0 | 57.3 | 0.2 | 0.96 |
| | 11 | 23.3 | 3.0 | 14.7 | 58.5 | 0.2 | 0.96 |
| | 12 | 23.1 | 3.2 | 14.9 | 58.2 | 0.2 | 0.96 |
| | 13 | 23.9 | 2.9 | 14.9 | 57.8 | 0.2 | 0.96 |
| | 14 | 22.9 | 2.9 | 14.4 | 59.3 | 0.2 | 0.96 |
| | 15 | 25.0 | 2.7 | 15.5 | 56.3 | 0.2 | 0.96 |
| | Mean | 24.4 | 2.7 | 15.0 | 57.4 | 0.2 | 0.96 |
| 95-6 | 1 | 25.9 | 2.5 | 15.0 | 56.1 | 0.2 | 0.97 |
| | 2 | 25.4 | 3.1 | 13.4 | 57.6 | 0.2 | 0.96 |
| | 3 | 24.7 | 3.3 | 14.7 | 56.7 | 0.2 | 0.96 |
| | 4 | 28.5 | 2.6 | 14.3 | 54.2 | 0.2 | 0.96 |
| | 5 | 25.9 | 3.1 | 13.0 | 57.5 | 0.2 | 0.96 |
| | 6 | 24.5 | 8.4 | 11.9 | 54.5 | 0.2 | 0.89 |
| | 7 | 25.8 | 8.5 | 12.3 | 52.7 | 0.2 | 0.88 |
| | 8 | 25.4 | 9.3 | 11.4 | 53.1 | 0.2 | 0.87 |
| | 9 | 23.6 | 11.6 | 11.8 | 52.1 | 0.2 | 0.85 |
| | 10 | 23.3 | 12.1 | 11.2 | 52.6 | 0.2 | 0.84 |
| | 11 | 23.6 | 12.1 | 10.6 | 52.8 | 0.2 | 0.84 |
| | 12 | 24.8 | 12.9 | 10.0 | 51.4 | 0.2 | 0.83 |
| | 13 | 23.6 | 12.5 | 11.2 | 51.8 | 0.2 | 0.83 |
| | 14 | 22.7 | 14.5 | 10.4 | 51.4 | 0.2 | 0.81 |
| | 15 | 23.6 | 16.0 | 9.9 | 49.4 | 0.2 | 0.79 |
| | Mean | 24.8 | 8.8 | 12.1 | 53.6 | 0.2 | 0.88 |
| 95-37 | 1 | 23.9 | 2.6 | 13.9 | 59.0 | 0.3 | 0.97 |
| | 2 | 23.9 | 3.0 | 14.7 | 58.0 | 0.2 | 0.96 |
| | 3 | 23.7 | 2.7 | 14.7 | 58.5 | 0.2 | 0.96 |
| | 4 | 23.4 | 2.9 | 16.0 | 57.4 | 0.2 | 0.96 |
| | 5 | 23.9 | 2.8 | 14.6 | 58.2 | 0.2 | 0.96 |
| | 6 | 19.0 | 21.6 | 8.0 | 50.0 | 0.3 | 0.73 |
| | 7 | 19.4 | 21.1 | 8.5 | 49.7 | 0.3 | 0.73 |
| | 8 | 19.2 | 22.4 | 8.8 | 48.3 | 0.2 | 0.72 |
| | 9 | 18.4 | 22.2 | 10.0 | 47.9 | 0.3 | 0.72 |
| | 10 | 18.1 | 23.7 | 7.5 | 49.2 | 0.3 | 0.71 |

TABLE 8-continued

Fatty acid composition (% of total fatty acids) of 15 individual T2 seeds from four T1 plants of cotton transformed with the Δ9-desaturase inverted-repeat gene silencing construct and from untransformed Coker control plants.

| T1 plant number | T2 seed number | Palmitic | Stearic | Oleic | Linoleic | Linolenic | SDP |
|---|---|---|---|---|---|---|---|
| | 11 | 18.2 | 24.8 | 7.4 | 48.1 | 0.3 | 0.69 |
| | 12 | 18.0 | 24.9 | 7.6 | 47.9 | 0.3 | 0.69 |
| | 13 | 17.5 | 25.1 | 8.1 | 47.7 | 0.3 | 0.69 |
| | 14 | 18.6 | 25.1 | 7.3 | 47.3 | 0.4 | 0.69 |
| | 15 | 17.9 | 27.8 | 7.2 | 45.5 | 0.3 | 0.66 |
| | Mean | 20.2 | 16.8 | 10.3 | 51.5 | 0.3 | 0.79 |
| 95-62 | 1 | 24.2 | 3.4 | 32.7 | 39.1 | 0.2 | 0.95 |
| | 2 | 24.0 | 11.1 | 19.8 | 43.8 | 0.3 | 0.85 |
| | 3 | 22.6 | 12.8 | 16.6 | 47.0 | 0.2 | 0.83 |
| | 4 | 21.6 | 14.4 | 11.4 | 51.5 | 0.3 | 0.81 |
| | 5 | 22.4 | 14.2 | 16.8 | 45.5 | 0.2 | 0.81 |
| | 6 | 20.3 | 16.8 | 12.5 | 49.3 | 0.3 | 0.79 |
| | 7 | 18.4 | 20.5 | 12.5 | 47.4 | 0.2 | 0.75 |
| | 8 | 20.2 | 19.8 | 8.8 | 49.9 | 0.3 | 0.75 |
| | 9 | 19.6 | 20.6 | 10.9 | 47.5 | 0.3 | 0.74 |
| | 10 | 18.3 | 23.7 | 9.1 | 47.4 | 0.3 | 0.71 |
| | 11 | 19.0 | 24.0 | 8.4 | 46.9 | 0.3 | 0.70 |
| | 12 | 18.6 | 24.4 | 8.4 | 47.1 | 0.2 | 0.70 |
| | 13 | 18.2 | 26.3 | 9.4 | 44.3 | 0.3 | 0.67 |
| | 14 | 17.0 | 30.8 | 6.5 | 43.8 | 0.3 | 0.62 |
| | 15 | 14.7 | 34.3 | 7.3 | 41.4 | 0.4 | 0.59 |
| | Mean | 19.9 | 19.8 | 12.7 | 46.1 | 0.3 | 0.75 |
| 95-150 | 1 | 26.2 | 2.3 | 16.3 | 54.8 | 0.1 | 0.97 |
| | 2 | 25.0 | 3.0 | 13.3 | 58.2 | 0.1 | 0.96 |
| | 3 | 25.0 | 3.0 | 14.0 | 57.5 | 0.2 | 0.96 |
| | 4 | 23.5 | 10.5 | 14.1 | 51.1 | 0.2 | 0.86 |
| | 5 | 22.4 | 14.6 | 11.8 | 50.2 | 0.2 | 0.81 |
| | 6 | 22.5 | 14.7 | 10.3 | 51.5 | 0.2 | 0.81 |
| | 7 | 22.2 | 15.8 | 9.8 | 51.3 | 0.2 | 0.80 |
| | 8 | 21.6 | 16.0 | 10.2 | 51.2 | 0.2 | 0.79 |
| | 9 | 22.6 | 16.6 | 9.9 | 49.7 | 0.2 | 0.78 |
| | 10 | 20.5 | 20.7 | 8.2 | 49.3 | 0.2 | 0.74 |
| | 11 | 21.0 | 20.6 | 8.2 | 48.8 | 0.2 | 0.74 |
| | 12 | 20.8 | 21.2 | 7.0 | 49.8 | 0.2 | 0.73 |
| | 13 | 20.8 | 20.9 | 7.9 | 49.1 | 0.2 | 0.73 |
| | 14 | 19.9 | 23.8 | 6.8 | 48.1 | 0.2 | 0.70 |
| | 15 | 19.5 | 24.8 | 7.7 | 46.5 | 0.2 | 0.69 |
| | Mean | 22.2 | 15.2 | 10.4 | 51.1 | 0.2 | 0.80 |

TABLE 9

Fatty acid composition (% of total fatty acids) of 12 individual T3 seeds from two independently derived T2 plants of cotton transformed with the Δ9-desaturase inverted-repeat gene silencing construct.

| T1 line | T3 seed No. | Palmitic | Stearic | Oleic | Linoleic | Linolenic | SDP |
|---|---|---|---|---|---|---|---|
| 95-62 | 1 | 16.6 | 32.9 | 7.3 | 41.2 | 0.3 | 0.60 |
| | 2 | 13.5 | 37.0 | 6.6 | 37.9 | 2.4 | 0.56 |
| | 3 | 17.6 | 32.2 | 7.3 | 41.1 | 0.1 | 0.60 |
| | 4 | 15.2 | 36.1 | 9.5 | 36.6 | 0.5 | 0.56 |
| | 5 | 15.8 | 37.3 | 7.9 | 36.4 | 0.4 | 0.54 |
| | 6 | 16.1 | 35.3 | 6.4 | 39.9 | 0.4 | 0.57 |
| | 7 | 16.8 | 29.2 | 8.5 | 42.3 | 1.3 | 0.64 |
| | 8 | 15.7 | 35.8 | 6.6 | 39.5 | 0.4 | 0.57 |
| | 9 | 15.8 | 35.6 | 7.9 | 38.3 | 0.4 | 0.57 |
| | 10 | 16.6 | 33.4 | 8.6 | 39.1 | 0.4 | 0.59 |
| | 11 | 16.5 | 33.6 | 7.5 | 40.1 | 0.4 | 0.59 |
| | 12 | 15.7 | 36.4 | 6.8 | 38.6 | 0.4 | 0.56 |
| | Mean | 16.0 | 34.6 | 7.6 | 39.3 | 0.6 | 0.58 |
| 95-150 | 1 | 17.7 | 26.5 | 7.5 | 46.7 | 0.2 | 0.67 |
| | 2 | 18.5 | 24.6 | 7.4 | 47.8 | 0.3 | 0.69 |
| | 3 | 16.1 | 31.3 | 6.5 | 44.2 | 0.2 | 0.62 |
| | 4 | 20.7 | 17.8 | 9.1 | 51.0 | 0.2 | 0.77 |
| | 5 | 16.3 | 31.1 | 6.6 | 44.4 | 0.2 | 0.62 |
| | 6 | 18.2 | 27.1 | 7.1 | 46.7 | 0.1 | 0.67 |
| | 7 | 19.3 | 21.9 | 7.4 | 49.6 | 0.7 | 0.73 |
| | 8 | 17.6 | 27.7 | 7.8 | 45.9 | 0.2 | 0.66 |
| | 9 | 15.8 | 32.0 | 7.1 | 43.1 | 0.2 | 0.61 |
| | 10 | 17.6 | 29.0 | 6.8 | 44.9 | 0.2 | 0.64 |
| | 11 | 15.7 | 33.8 | 5.7 | 42.9 | 0.2 | 0.59 |
| | 12 | 18.0 | 25.4 | 7.2 | 47.8 | 0.2 | 0.69 |
| | Mean | 17.6 | 27.3 | 7.2 | 46.3 | 0.2 | 0.66 |

EXAMPLE 16

Fatty Acid Contents of Oils from Seed of Transgenic T1 Cotton Plants Carrying the ghFAD2-1 Inverted Repeat Gene Construct The seeds produced by independent transgenic (T1) plants containing an inverted repeat of the cotton fatty acid Δ12-desaturase gene, and a non-transformed isogenic *G. hirsutum* coker cotton, were analysed for their fatty acid composition. Samples consisting of three pooled T2 seeds derived from a number of individual T1 plants. Fatty acid methyl esters were prepared as described by Bligh and Dyer (1959). Methyl esters were separated by gas chromatography (GC), using a Hewlett-Packard 5890 gas chromatograph fitted with a fused silica capillary column (HP-FFAP, 0.53 mm×30 m). Fatty acids were identified by reference to chemical standards as described hereinabove.

Data are presented in Table 10. Because T1 plants were generally hemizygous for the introduced transgene, the T2 seeds were segregating for that transgene. Accordingly, the data for pooled T2 seed samples shown in Table 10 are an averaging of fatty acid levels for seeds that are either homozygous or hemizygous for the transgene, or lack the transgene altogether.

Increased Oleic Acid

Expression of the inverted repeat of the 5'-end of ghFAD2-1 in cotton appeared to decrease the level of the oleyl-PC Δ12 desaturase enzyme activity in cotton, as suggested by the elevated level of oleic acid in transgenic T2 seed. As summaried in Table 10, several independent transgenic lines exhibited increased oleic acid content compared to non-transformed plants. The oleic acid content increased from 15% for non-transformed Coker cotton, to 77% for the transgenic line 125-23, representing an increase of up to about 5-fold to 5.5-fold for this fatty acid in cotton.

Decreased Linoleic Acid

Linoleic acid was reduced in transgenic cotton lines, from 57.4% of total seed lipid in the non-transgenic Coker cotton, to only 3.5% in line 125-50, representing a decrease in linoleic acid content of up to about 95% in the transgenic lines.

Decreased Palmitic Acid

Unexpectedly, and favourably, palmitic acid was significantly reduced in the T2 seed of transgenic cotton containing the inverted repeat of the 5'-end of ghFAD2-1. The level of palmitic acid in the seed of transgenic plants was reduced to only 16.8% of total seed lipid in line 125-23, compared to 24.4% of total seed lipid for isogenic non-transformed plants. This represents a decrease in palmitic acid content of up to about 35% to 37% in the transgenic lines.

TABLE 10

Fatty acid contents of ghFAD2-1-downregulated transgenic cotton

| Plant line | Fatty acid composition (%) | | | | | ODP |
|---|---|---|---|---|---|---|
| | Palmitic | Stearic | Oleic | Linoleic | Linolenic | |
| Coker | 24.4 | 2.7 | 15.0 | 57.4 | 0.2 | 0.79 |
| 125-26 | 23.8 | 2.6 | 13.2 | 60.0 | 0.1 | 0.82 |
| 125-54 | 24.5 | 2.5 | 13.2 | 59.6 | 0.0 | 0.82 |
| 125-8 | 24.0 | 2.6 | 13.7 | 59.3 | 0.2 | 0.81 |
| 125-83 | 25.0 | 2.7 | 13.7 | 58.2 | 0.2 | 0.81 |
| 125-60 | 25.3 | 2.4 | 13.8 | 58.0 | 0.2 | 0.81 |
| 125-51 | 23.4 | 2.5 | 14.0 | 59.7 | 0.2 | 0.81 |
| 125-127 | 24.0 | 2.7 | 14.1 | 58.8 | 0.2 | 0.81 |
| 125-82 | 24.9 | 2.2 | 14.6 | 58.1 | 0.0 | 0.80 |
| 125-125 | 25.6 | 2.6 | 14.2 | 57.5 | 0.2 | 0.80 |
| 125-10 | 23.2 | 2.9 | 14.3 | 59.2 | 0.2 | 0.81 |
| 125-13 | 24.4 | 2.6 | 14.6 | 58.0 | 0.2 | 0.80 |
| 125-129 | 24.1 | 2.4 | 15.2 | 57.9 | 0.2 | 0.79 |
| 125-84 | 23.9 | 2.9 | 15.3 | 57.5 | 0.2 | 0.79 |
| 125-117 | 23.8 | 2.4 | 15.5 | 57.8 | 0.2 | 0.79 |
| 125-12 | 23.9 | 2.8 | 16.4 | 56.4 | 0.2 | 0.78 |
| 125-131 | 23.9 | 1.9 | 24.3 | 49.6 | 0.1 | 0.67 |
| 125-79 | 22.2 | 2.7 | 32.2 | 42.4 | 0.2 | 0.57 |
| 125-120 | 23.5 | 2.4 | 32.6 | 40.9 | 0.2 | 0.56 |
| 125-130 | 20.7 | 2.7 | 47.3 | 28.8 | 0.2 | 0.39 |
| 125-33 | 18.7 | 3.1 | 51.2 | 26.4 | 0.2 | 0.34 |
| 125-121 | 21.7 | 2.2 | 58.5 | 17.1 | 0.2 | 0.23 |
| 125-62 | 17.6 | 2.3 | 66.0 | 13.5 | 0.3 | 0.17 |
| 125-7 | 16.0 | 2.6 | 73.7 | 7.2 | 0.2 | 0.09 |
| 125-81 | 20.9 | 2.6 | 68.9 | 7.0 | 0.2 | 0.09 |
| 125-85 | 20.8 | 2.7 | 71.5 | 4.4 | 0.2 | 0.06 |
| 125-124 | 18.7 | 1.8 | 72.5 | 6.4 | 0.2 | 0.08 |
| 125-128 | 18.5 | 2.4 | 74.3 | 4.3 | 0.1 | 0.06 |
| 125-1 | 18.1 | 2.7 | 73.7 | 44.9 | 0.2 | 0.06 |
| 125-96 | 19.4 | 2.2 | 74.1 | 3.8 | 0.2 | 0.05 |
| 125-50 | 18.9 | 2.3 | 74.7 | 3.5 | 0.2 | 0.05 |
| 125-114 | 17.8 | 2.2 | 75.1 | 4.4 | 0.1 | 0.06 |
| 125-23 | 16.8 | 1.4 | 77.0 | 4.4 | 0.2 | 0.06 |

It is well established for oilseed plant species that the fatty acid composition of a somatic embryoid reflects the fatty acid composition of the sexual embryo. For example, in soybean, the fatty acid composition of middle maturity somatic embryoids is predictive of the final oil composition of seed derived from plants that have been regenerated from these embryoids. Proceeding on this basis, somatic embryoids generated from transgenic soybean calli have previously been used as an indicator of the fatty acid composition of the seed derived therefrom (Cahoon et al., 1999; Cahoon et al, 2000). This approach facilitates the early detection and rapid selection of transgenic lines having desired oilseed composition.

To demonstrate the effectiveness of the intron-interrupted UTR inverted-repeat gene construct (Example 11) in down-regulating expression of the Δ12-desaturase gene, the fatty acid compositions of somatic embryoids regenerating from 18 independent primary transformed calli of Coker cotton were determined. Data presented in Table 11 support the conclusion that the ghFAD2-1 gene encoding fatty acid Δ12-desaturase has been silenced in lines expressing the intron-interrupted UTR inverted-repeat gene construct.

In particular, the level of oleic acid has been enhanced in somatic embryoids carrying the intron-interrupted UTR inverted-repeat gene construct, compared to the levels typical for somatic embryoids derived from untransformed plants. Oleic acid constitutes as much as 66% of the total fatty acids in transformed embryoids (Table 11), compared to only about 15% for typical somatic embryoids derived from untransformed Coker cotton plants (Tables 7 and 8). On average, this represents about 3-fold enhanced oleic acid content.

Additionally, the level of linoleic acid is reduced in somatic embryoids, carrying the intron-interrupted UTR inverted-repeat gene construct, compared to the levels typical for somatic embryoids derived from untransformed plants. Linoleic acid constitutes only about 10–31% (average 23%) of the total fatty acids in transformed somatic embryoids (Table 11), compared to about 57.4% for typical somatic embryoids derived from transformed Coker cotton plants (Tables 7 and 8). On average, this represents more than 50% reduction in linoleic acid content.

Additionally, the level of palmitic acid is reduced in the transgenic somatic embryoids carrying the intron-interrupted UTR inverted-repeat gene construct, compared to somatic embryoids derived from untransformed plants. Palmitic acid constitutes on average about 20% of the total fatty acids in transformed embryoids (Table 11), compared to about 24.4% for somatic embryoids derived from untransformed Coker cotton plants (Tables 7 and 8). On average, this represents about 25% reduction in linoleic acid content.

Since similar results were obtained using different inverted repeat gene constructs, the modulation of fatty acid content obtained using inverted repeat sequences is not dependent on the precise nature of the inverted repeat in the gene construct. However, the frequency of gene silencing that we detected was enhanced in transformants carrying the intron-interrupted UTR inverted-repeat gene construct compared to transformants carrying the coding region inverted-repeat, or transformants carrying antisense constructs.

TABLE 11

Fatty acid contents of embryoids carrying the ghFAD2-1 intron-interrupted UTR inverted-repeat construct

| Embryoid No. | Fatty acid composition (%) | | | | | ODP |
|---|---|---|---|---|---|---|
| | Palmitic | Stearic | Oleic | Linoleic | Linolenic | |
| 1 | 19.9 | 6.4 | 45.1 | 23.4 | 3.8 | 0.38 |
| 2 | 19.3 | 4.5 | 46.5 | 27.9 | 1.4 | 0.39 |
| 3 | 19.5 | 3.3 | 63.6 | 10.8 | 2.2 | 0.17 |
| 4 | 22.1 | 5.5 | 48.9 | 20.1 | 3.4 | 0.32 |
| 5 | 20.8 | 5.8 | 56.0 | 15.0 | 1.7 | 0.23 |
| 6 | 20.3 | 7.7 | 49.7 | 18.2 | 2.8 | 0.30 |
| 7 | 22.0 | 4.4 | 45.0 | 24.4 | 4.2 | 0.39 |
| 8 | 15.7 | 3.2 | 26.3 | 28.6 | 26.3 | 0.68 |
| 9 | 23.1 | 6.1 | 42.9 | 22.9 | 3.9 | 0.38 |
| 10 | 18.5 | 2.1 | 55.2 | 24.0 | 0.1 | 0.30 |
| 11 | 21.6 | 5.1 | 45.5 | 25.5 | 1.5 | 0.37 |
| 12 | 23.2 | 5.4 | 41.2 | 27.6 | 1.8 | 0.42 |
| 13 | 19.9 | 2.3 | 49.6 | 28.0 | 0.0 | 0.36 |
| 14 | 19.0 | 2.1 | 47.5 | 31.2 | 0.1 | 0.40 |
| 15 | 19.5 | 2.3 | 65.6 | 10.8 | 1.7 | 0.16 |
| 16 | 18.1 | 3.6 | 57.7 | 20.7 | 1.9 | 0.28 |
| 17 | 22.0 | 4.4 | 45.0 | 26.4 | 2.4 | 0.39 |
| 18 | 21.4 | 4.6 | 43.1 | 28.6 | 1.7 | 0.41 |
| Mean | 20.3 | 4.4 | 48.6 | 23.0 | 3.4 | 0.35 |

A proportion of the somatic embryoids carrying the intron-interrupted UTR inverted-repeat construct were allowed to regenerate into T1 plants. The fatty acid compositions of T2 seed from those regenerated plants were determined. Data presented in Table 12 show the fatty acid composition of 15 individual T2 seeds. Those data indicate that, as with the somatic embryoids from which the plants were derived, the level of oleic acid is enhanced, and the levels of palmitic acid and linoleic acid are reduced, in the T2 seeds of embryoid-derived T1 plants.

These data demonstrate that distinct gene silencing constructs comprising inverted repeats of fatty acid desaturase genes are effective in predictably modulating the fatty acid composition of cottonseed. The expression of such gene constructs may be placed operably under the control of distinct seed-operable promoter sequences.

TABLE 12

Fatty acid contents of 15 individual T2 seeds from a cotton embryoid carrying the ghFAD2-1 intron-interrupted UTR inverted-repeat construct

| T1 plant No. | T2 seed No. | Palmitic | Stearic | Oleic | Linoleic | Linolenic | ODP |
|---|---|---|---|---|---|---|---|
| 10 | 1 | 24.1 | 2.1 | 57.8 | 15.8 | 0.1 | 0.22 |
|  | 2 | 22.5 | 2.1 | 68.0 | 7.0 | 0.1 | 0.10 |
|  | 3 | 23.0 | 2.3 | 67.5 | 6.9 | 0.2 | 0.09 |
|  | 4 | 25.4 | 2.1 | 54.8 | 17.4 | 0.1 | 0.24 |
|  | 5 | 22.8 | 2.6 | 27.9 | 46.3 | 0.2 | 0.63 |
|  | 6 | 19.5 | 2.3 | 69.3 | 8.5 | 0.2 | 0.11 |
|  | 7 | 19.9 | 2.2 | 70.6 | 6.9 | 0.1 | 0.09 |
|  | 8 | 18.8 | 2.3 | 71.6 | 6.9 | 0.2 | 0.09 |
|  | 9 | 20.2 | 2.1 | 70.1 | 7.2 | 0.1 | 0.10 |
|  | 10 | 19.3 | 2.5 | 68.1 | 9.6 | 0.2 | 0.13 |
|  | 11 | 19.0 | 2.0 | 68.8 | 9.7 | 0.1 | 0.13 |
|  | 12 | 20.2 | 2.4 | 47.1 | 29.9 | 0.2 | 0.39 |
|  | 13 | 18.3 | 2.1 | 70.4 | 8.6 | 0.2 | 0.11 |
|  | 14 | 20.3 | 2.2 | 63.9 | 13.2 | 0.2 | 0.17 |
|  | 15 | 18.5 | 2.5 | 68.7 | 9.8 | 0.1 | 0.13 |
|  | Mean | 20.8 | 2.3 | 63.0 | 13.6 | 0.2 | 0.18 |

EXAMPLE 17

Characterisation of Oils in Transgenic Seed that is Homozygous for the Transgene Containing an Inverted Repeat of a Fatty Acid Δ12-Desaturase Gene T2 that are homozygous for the introduced inverted repeat of the cotton fatty acid Δ12-desaturase gene were identified by selection. The fatty acid compositions of individual T2 seeds (15 in total), derived from several representative T1 plants that differed widely in their stearic acid content, were analysed as described in the preceding example. Data are presented in Table 13.

It is clear that different transgenic events are associated with different levels of reduction in Δ12-desaturase activity (as indicated by ODP) and corresponding different levels of accumulation of the oleic acid substrate. This variation is explainable by different transgene copy numbers and different genomic integration locations of the transgenes. By producing a sufficient number of independent transgenics, any particular desired oleic acid content between the normal upper limit for cotton (approximately 16%) and approximately 75% can therefore be obtained (see FIG. 12).

To confirm that the observed Δ12-desaturase gene silencing was heritable, additional T2 seed, and T3 seed, were obtained from plants exhibiting the most severe silencing phenotype, in particular, the independent T1 plants having the higher levels of oleic acid in their seed and designated 125-124 and 125-23 (Table 10). The fatty acid compositions of 15 individual T2 seed and 12 individual T3 seed from these lines were determined as described in the preceding example. The T2 segregation patterns were consistent with a single transgene insertion (Table 13). Data presented in Table 14 demonstrate that the high level silencing observed in the pooled T2 seeds of both lines as shown in Table 10, or the individual T2 seeds of line 125-23 as shown in Table 13, is inherited in the T3 generation, as evidenced by the heritability of the high oleic acid and low linoleic acid and low palmitic acid phenotypes.

TABLE 13

Fatty acid composition (% of total fatty acids) of 15 individual T2 seeds from five T1 plants of cotton transformed with the Δ12-desaturase inverted-repeat gene silencing construct and from untransformed Coker control plants.

| T1 plant No. | T2 seed No. | Palmitic | Stearic | Oleic | Linoleic | Linolenic | ODP |
|---|---|---|---|---|---|---|---|
| Coker control | 1 | 25.1 | 2.6 | 15.2 | 56.6 | 0.2 | 0.97 |
|  | 2 | 25.4 | 2.8 | 15.7 | 55.6 | 0.2 | 0.78 |
|  | 3 | 25.1 | 2.6 | 14.9 | 57.0 | 0.2 | 0.79 |
|  | 4 | 23.9 | 2.7 | 15.1 | 58.0 | 0.2 | 0.79 |
|  | 5 | 24.3 | 2.2 | 14.7 | 58.3 | 0.2 | 0.80 |
|  | 6 | 25.2 | 2.5 | 14.4 | 57.4 | 0.2 | 0.80 |
|  | 7 | 24.0 | 2.9 | 16.2 | 56.4 | 0.2 | 0.78 |
|  | 8 | 24.9 | 2.3 | 15.0 | 57.4 | 0.2 | 0.79 |
|  | 9 | 24.4 | 2.8 | 15.0 | 57.3 | 0.2 | 0.79 |
|  | 10 | 23.3 | 3.0 | 14.7 | 58.5 | 0.2 | 0.80 |
|  | 11 | 23.1 | 3.2 | 14.9 | 58.2 | 0.2 | 0.80 |
|  | 12 | 23.9 | 2.9 | 14.9 | 57.8 | 0.2 | 0.80 |
|  | 13 | 25.2 | 2.6 | 14.8 | 56.9 | 0.2 | 0.79 |
|  | 14 | 22.9 | 2.9 | 14.4 | 59.3 | 0.2 | 0.80 |
|  | 15 | 25.0 | 2.7 | 15.5 | 56.3 | 0.2 | 0.78 |
|  | Mean | 24.4 | 2.7 | 15.0 | 57.4 | 0.2 | 0.79 |
| 125-120 | 1 | 26.9 | 2.1 | 13.5 | 57.1 | 0.2 | 0.81 |
|  | 2 | 25.0 | 2.7 | 19.7 | 52.1 | 0.2 | 0.73 |
|  | 3 | 24.9 | 2.1 | 19.8 | 52.8 | 0.2 | 0.73 |
|  | 4 | 22.9 | 2.2 | 25.7 | 48.8 | 0.2 | 0.66 |
|  | 5 | 24.4 | 2.5 | 25.3 | 47.3 | 0.2 | 0.65 |
|  | 6 | 24.0 | 2.3 | 27.2 | 46.0 | 0.2 | 0.63 |
|  | 7 | 24.2 | 2.0 | 28.4 | 45.0 | 0.2 | 0.61 |
|  | 8 | 24.6 | 2.3 | 31.2 | 41.5 | 0.1 | 0.57 |
|  | 9 | 22.9 | 2.2 | 33.8 | 40.7 | 0.2 | 0.55 |
|  | 10 | 25.2 | 2.2 | 34.6 | 37.6 | 0.2 | 0.52 |
|  | 11 | 21.7 | 2.5 | 42.6 | 32.8 | 0.2 | 0.44 |
|  | 12 | 22.6 | 2.7 | 44.4 | 29.8 | 0.2 | 0.40 |
|  | 13 | 22.6 | 2.2 | 46.1 | 28.6 | 0.2 | 0.38 |
|  | 14 | 23.0 | 2.0 | 46.4 | 28.1 | 0.2 | 0.38 |
|  | 15 | 22.5 | 2.3 | 51.6 | 23.1 | 0.2 | 0.31 |
|  | Mean | 23.8 | 2.3 | 32.7 | 40.8 | 0.2 | 0.56 |
| 125-130 | 1 | 24.9 | 2.7 | 14.6 | 57.3 | 0.2 | 0.80 |
|  | 2 | 18.8 | 2.5 | 71.6 | 6.5 | 0.2 | 0.09 |
|  | 3 | 17.4 | 2.4 | 73.8 | 5.8 | 0.2 | 0.08 |
|  | 4 | 19.7 | 2.3 | 71.5 | 6.0 | 0.2 | 0.08 |
|  | 5 | 19.6 | 2.3 | 72.2 | 5.5 | 0.2 | 0.07 |
|  | 6 | 18.9 | 2.5 | 72.4 | 5.6 | 0.2 | 0.07 |
|  | 7 | 17.6 | 2.7 | 73.6 | 5.5 | 0.2 | 0.07 |
|  | 8 | 20.5 | 2.3 | 71.8 | 5.1 | 0.2 | 0.07 |
|  | 9 | 19.4 | 2.7 | 72.1 | 5.5 | 0.1 | 0.07 |
|  | 10 | 19.8 | 2.4 | 72.6 | 5.3 | 0.0 | 0.07 |
|  | 11 | 18.0 | 2.3 | 74.8 | 4.4 | 0.2 | 0.06 |
|  | 12 | 18.1 | 2.5 | 74.4 | 4.5 | 0.2 | 0.06 |
|  | 13 | 16.7 | 2.6 | 75.3 | 4.9 | 0.2 | 0.06 |
|  | 14 | 18.3 | 2.6 | 73.7 | 4.9 | 0.2 | 0.06 |
|  | 15 | 23.6 | 1.9 | 69.4 | 4.7 | 0.1 | 0.06 |
|  | Mean | 19.4 | 2.4 | 68.9 | 8.8 | 0.2 | 0.12 |
| 125-121 | 1 | 24.9 | 2.6 | 17.4 | 54.7 | 0.2 | 0.76 |
|  | 2 | 24.7 | 2.5 | 17.3 | 55.1 | 0.2 | 0.76 |
|  | 3 | 23.8 | 3.0 | 18.2 | 54.6 | 0.2 | 0.75 |
|  | 4 | 26.1 | 2.9 | 22.1 | 48.4 | 0.3 | 0.69 |
|  | 5 | 26.0 | 2.1 | 22.0 | 49.5 | 0.2 | 0.69 |
|  | 6 | 25.0 | 2.8 | 25.0 | 46.7 | 0.2 | 0.65 |
|  | 7 | 25.2 | 2.6 | 29.0 | 42.7 | 0.1 | 0.60 |
|  | 8 | 23.2 | 2.5 | 34.0 | 40.0 | 0.2 | 0.54 |
|  | 9 | 25.0 | 2.3 | 38.7 | 33.6 | 0.2 | 0.47 |
|  | 10 | 21.3 | 2.9 | 45.6 | 29.7 | 0.1 | 0.40 |
|  | 11 | 23.8 | 2.4 | 45.8 | 27.6 | 0.1 | 0.38 |
|  | 12 | 21.0 | 2.6 | 51.2 | 24.8 | 0.2 | 0.33 |
|  | 13 | 20.1 | 2.4 | 65.5 | 11.5 | 0.2 | 0.15 |
|  | 14 | 20.0 | 2.3 | 70.0 | 7.3 | 0.1 | 0.10 |
|  | 15 | 19.9 | 2.3 | 71.6 | 5.7 | 0.1 | 0.08 |
|  | Mean | 23.3 | 2.5 | 38.2 | 35.4 | 0.2 | 0.49 |

TABLE 13-continued

Fatty acid composition (% of total fatty acids) of 15 individual T2 seeds from five T1 plants of cotton transformed with the Δ12-desaturase inverted-repeat gene silencing construct and from untransformed Coker control plants.

| T1 plant No. | T2 seed No. | Palmitic | Stearic | Oleic | Linoleic | Linolenic | ODP |
|---|---|---|---|---|---|---|---|
| 125-81 | 1 | 25.0 | 3.0 | 14.6 | 56.8 | 0.2 | 0.80 |
| | 2 | 26.6 | 2.7 | 15.7 | 54.5 | 0.2 | 0.78 |
| | 3 | 25.4 | 2.8 | 16.2 | 55.2 | 0.2 | 0.77 |
| | 4 | 21.2 | 2.8 | 68.2 | 7.2 | 0.2 | 0.10 |
| | 5 | 19.3 | 2.5 | 70.9 | 6.7 | 0.2 | 0.09 |
| | 6 | 19.8 | 2.7 | 70.0 | 7.0 | 0.2 | 0.09 |
| | 7 | 20.8 | 2.5 | 69.9 | 6.2 | 0.2 | 0.08 |
| | 8 | 21.5 | 2.6 | 69.3 | 6.0 | 0.2 | 0.08 |
| | 9 | 19.7 | 2.7 | 70.9 | 6.2 | 0.2 | 0.08 |
| | 10 | 19.7 | 2.7 | 71.1 | 6.0 | 0.2 | 0.08 |
| | 11 | 20.0 | 2.7 | 70.3 | 6.3 | 0.2 | 0.08 |
| | 12 | 21.0 | 2.5 | 70.1 | 5.9 | 0.2 | 0.08 |
| | 13 | 20.8 | 2.6 | 70.7 | 5.3 | 0.2 | 0.07 |
| | 14 | 19.5 | 2.7 | 72.2 | 5.0 | 0.2 | 0.07 |
| | 15 | 19.5 | 2.9 | 72.1 | 4.8 | 0.1 | 0.06 |
| | Mean | 21.3 | 2.7 | 59.5 | 15.9 | 0.2 | 0.22 |
| 125-23 | 1 | 23.5 | 2.4 | 13.7 | 60.1 | 0.1 | 0.81 |
| | 2 | 24.2 | 2.5 | 14.1 | 58.8 | 0.1 | 0.81 |
| | 3 | 23.9 | 2.5 | 14.4 | 58.9 | 0.1 | 0.80 |
| | 4 | 23.9 | 2.4 | 15.2 | 58.1 | 0.1 | 0.79 |
| | 5 | 25.9 | 2.4 | 15.5 | 55.9 | 0.1 | 0.78 |
| | 6 | 17.8 | 2.3 | 72.1 | 7.4 | 0.1 | 0.09 |
| | 7 | 17.2 | 2.5 | 73.5 | 6.5 | 0.1 | 0.08 |
| | 8 | 18.0 | 2.0 | 73.8 | 5.9 | 0.1 | 0.08 |
| | 9 | 20.7 | 2.3 | 70.8 | 5.8 | 0.1 | 0.08 |
| | 10 | 21.1 | 2.3 | 70.2 | 6.0 | 0.1 | 0.08 |
| | 11 | 18.5 | 2.5 | 72.1 | 6.5 | 0.2 | 0.08 |
| | 12 | 18.1 | 2.5 | 73.8 | 5.1 | 0.1 | 0.07 |
| | 13 | 17.8 | 2.4 | 74.2 | 5.2 | 0.1 | 0.07 |
| | 14 | 17.1 | 2.7 | 74.6 | 5.0 | 0.1 | 0.06 |
| | 15 | 17.6 | 2.4 | 74.7 | 4.9 | 0.1 | 0.06 |
| | Mean | 20.4 | 2.4 | 53.5 | 23.3 | 0.1 | 0.32 |

TABLE 14

Fatty acid composition (% of total fatty acids) of 12 individual T3 seeds from two independently derived T2 plants of cotton transformed with a Δ12-desaturase inverted-repeat gene silencing construct.

| T1 plant | T3 seed | Palmitic | Stearic | Oleic | Linoleic | Linolenic | ODP |
|---|---|---|---|---|---|---|---|
| 125-23 | 1 | 15.8 | 2.3 | 77.1 | 4.2 | 0.2 | 0.05 |
| | 2 | 15.9 | 2.6 | 76.5 | 4.3 | 0.2 | 0.05 |
| | 3 | 15.4 | 2.6 | 77.2 | 4.1 | 0.2 | 0.05 |
| | 4 | 15.3 | 2.5 | 77.3 | 4.3 | 0.2 | 0.05 |
| | 5 | 15.7 | 2.7 | 77.0 | 3.9 | 0.2 | 0.05 |
| | 6 | 15.5 | 2.6 | 77.0 | 4.3 | 0.2 | 0.05 |
| | 7 | 15.3 | 2.7 | 77.1 | 4.3 | 0.2 | 0.05 |
| | 8 | 15.5 | 2.8 | 76.9 | 4.2 | 0.2 | 0.05 |
| | 9 | 17.0 | 2.5 | 75.7 | 4.1 | 0.2 | 0.05 |
| | 10 | 16.7 | 2.7 | 76.0 | 4.1 | 0.2 | 0.05 |
| | 11 | 17.0 | 2.7 | 75.6 | 4.1 | 0.2 | 0.05 |
| | 12 | 17.4 | 2.6 | 75.3 | 4.1 | 0.2 | 0.05 |
| | Mean | 16.0 | 2.6 | 76.6 | 4.2 | 0.2 | 0.05 |
| 125-124 | 1 | 18.0 | 2.1 | 73.5 | 6.0 | 0.3 | 0.08 |
| | 2 | 20.8 | 2.1 | 71.1 | 5.5 | 0.3 | 0.07 |
| | 3 | 18.7 | 2.2 | 73.0 | 5.7 | 0.2 | 0.07 |
| | 4 | 18.2 | 2.2 | 72.4 | 6.9 | 0.2 | 0.O9 |
| | 5 | 18.9 | 2.2 | 72.7 | 5.6 | 0.3 | 0.07 |
| | 6 | 17.8 | 2.2 | 72.7 | 6.8 | 0.3 | 0.09 |
| | 7 | 17.5 | 2.5 | 73.6 | 5.9 | 0.4 | 0.08 |
| | 8 | 21.1 | 2.1 | 70.8 | 5.7 | 0.2 | 0.08 |
| | 9 | 18.5 | 2.3 | 73.6 | 5.4 | 0.2 | 0.07 |
| | 10 | 18.5 | 2.2 | 72.4 | 6.5 | 0.3 | 0.08 |
| | 11 | 18.3 | 2.3 | 72.7 | 6.4 | 0.2 | 0.08 |
| | 12 | 18.5 | 2.3 | 73.1 | 5.7 | 0.3 | 0.07 |
| | Mean | 18.7 | 2.2 | 72.6 | 6.0 | 0.3 | 0.08 |

EXAMPLE 18

Sexual Hybridisation of Elite Transgenic Lines to Enhance Cotton Seed Oil Characteristics To produce a cotton seed oil which is rich in both oleic acid and stearic acid, and preferably low in palmitic acid, we conducted preliminary crosses between some of the transgenic T1 plant lines that produce high levels of stearic acid and oleic acid, as discussed in the preceding examples. In particular, line 95-150, which produces high stearic acid, and has reduced palmitic acid, oleic acid, and linoleic acid, was crossed to line 125-23, or line 125-96, or line 125-62, all of which produce high levels of oleic acid, and have low palmitic acid, and low linoleic acid content. We analysed the fatty acid composition of the F1 seed produced from those sexual hybridisations. Some of the novel fatty acid profiles detected in the F1 seed are summarised in Table 15.

Increased Stearic Acid

In the F1 seeds of three different crosses shown in Table 15, stearic acid content ranged from 7.1–14.9% of total seed lipid, compared to only 2.0% for non-transformed Coker cotton. Accordingly, these data indicate that it is possible to increase the level of stearic acid in cotton by as much as about 3.5-fold to about 7.5-fold, by expressing inverted repeats in cotton which target independently the endogenous cotton fatty acidΔ9-desaturase and Δ12-desaturase genes, and then crossing the transgenic plants.

Increased Oleic Acid

Oleic acid content ranged from 59.9% to 67.1% of total seed lipid in the F1 seed, compared to only 19–6% for non-transformed Coker cotton. Accordingly, these data indicate that it is possible to increase the level of oleic acid in cotton by up to about 3.5-fold, by expressing inverted repeats in cotton which target independently the endogenous cotton fatty acid Δ9-desaturase and Δ12-desaturase genes, and then crossing the transgenic plants.

Decreased Linoleic Acid

Linoleic acid content ranged from only 4.8% to 6.6% of total seed lipid in the F1 seed, compared to 54.4% for non-transformed Coker cotton. Accordingly, these data indicate that it is possible to decrease the level of linoleic acid in cotton by up to about 91.1%, by expressing inverted repeats in cotton which target independently the endogenous cotton fatty acid Δ9-desaturase and Δ12-desaturase genes, and then crossing the transgenic plants.

Decreased Palmitic Acid

Palmitic acid content ranged from only 17.6% to 19.5% of total seed lipid in the F1 seed, compared to 23.6% for non-transformed Coker cotton. Accordingly, these data indicate that it is possible to decrease the level of palmitic acid in cotton by up to about 25.4%, by expressing inverted repeats in cotton which target independently the endogenous cotton fatty acid Δ9-desaturase and Δ12-desaturase genes, and then crossing the transgenic plants.

TABLE 15

Average fatty acid compositions of F1 seed derived from sexual hybridisation of transgenic cotton lines

| Cotton line | Average Fatty Acid Composition (%) | | | | | | |
|---|---|---|---|---|---|---|---|
| | Palmitic | Stearic | Oleic | Linoleic | Linolenic | SDP | ODP |
| Coker | 23.6 | 2.0 | 19.6 | 54.4 | 0.1 | 0.97 | 0.74 |
| Transgenic parental lines | | | | | | | |
| 125-23 | 16.8 | 1.4 | 77.0 | 4.4 | 0.2 | 0.98 | 0.06 |
| 125-62 | 17.6 | 2.3 | 66.1 | 13.5 | 0.3 | 0.97 | 0.17 |
| 125-96 | 19.4 | 2.2 | 74.1 | 3.8 | 0.2 | 0.97 | 0.05 |
| 95-150 | 19.0 | 28.0 | 5.8 | 45.4 | 0.3 | 0.65 | 0.89 |
| F1 progeny of the cross 125-23 × 95-150 | | | | | | | |
| F1 #1 | 18.5 | 8.6 | 65.8 | 6.0 | 0.1 | 0.89 | 0.09 |
| F1 #2 | 17.9 | 12.1 | 62.1 | 6.6 | 0.2 | 0.85 | 0.10 |
| F1 #3 | 17.6 | 12.5 | 63.0 | 5.7 | 0.1 | 0.85 | 0.08 |
| F1 #4 | 17.9 | 10.0 | 65.5 | 5.6 | 0.1 | 0.88 | 0.08 |
| F1 progeny of the cross 125-96 × 95-150 | | | | | | | |
| F1 #1 | 19.5 | 7.1 | 67.6 | 4.8 | 0.1 | 0.91 | 0.07 |
| F1 #2 | 19.2 | 7.1 | 66.9 | 5.9 | 0.1 | 0.91 | 0.08 |
| F1 progeny of the cross 125-62 × 95-150 | | | | | | | |
| F1 #1 | 17.6 | 14.9 | 59.9 | 6.1 | 0.1 | 0.81 | 0.09 |

Figure 13:
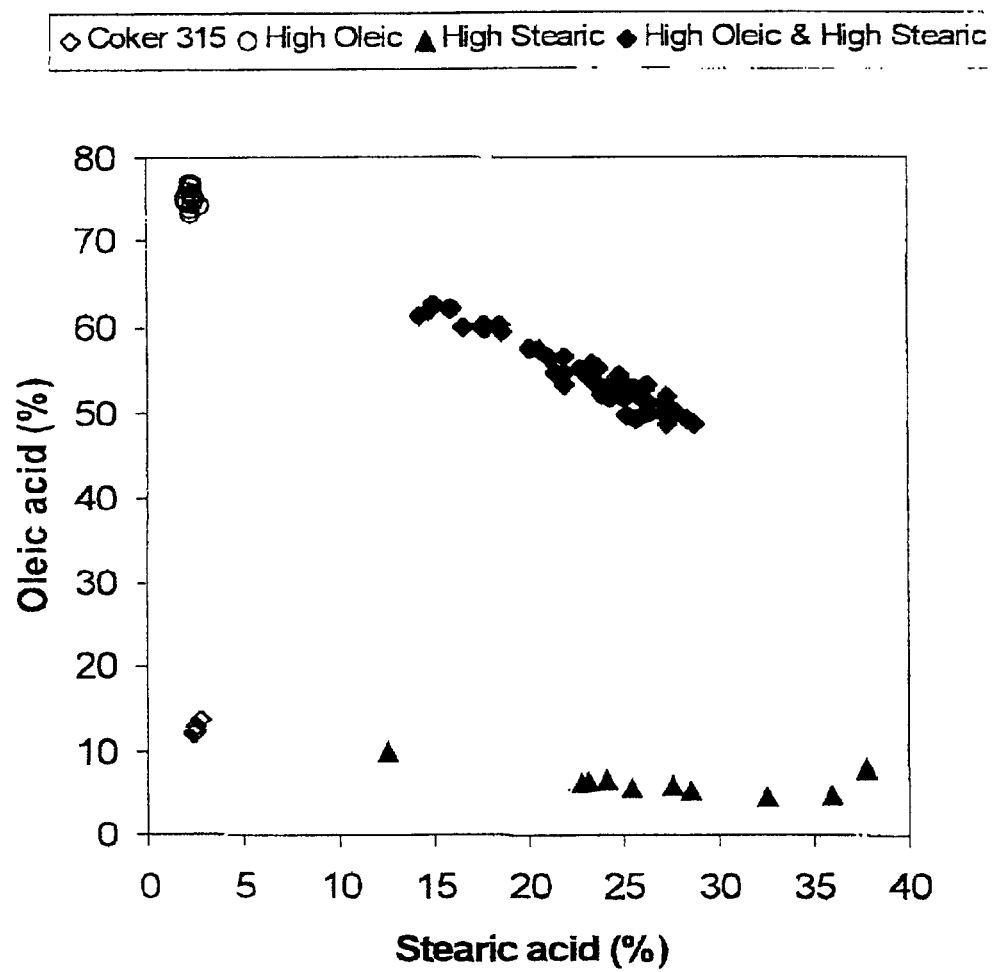
FIG. 13 is a graphical representation showing the relationship between stearic acid (x-axis) and oleic acid (abscissa) content, as a percentage of total fatty acids, in 86 F2 seeds derived from the 125-23×95-150 cross that are classified as high oleic acid seed (○), high stearic acid seed (▼), high stearic acid and high oleic acid seed (♦), or normal Coker 315-type seed (◇). Data show that the levels of both of these fatty acids can be modulated to produce combinations of high stearic and high oleic acid that are not found in either transformed parental line or in the untransformed Coker 315 parent.

A population of 86 individual F2 seeds from the cross 125-23×95-150 was analysed for fatty acid composition as described in previous examples, to determine the range of fatty acid compositions obtained by recombination between the parental phenotypes. As shown in FIG. 13, stearic acid and oleic acid compositions of cottonseed can be manipulated to produce levels of these fatty acids that range anywhere between the normal (wild type) level for untransformed Coker cotton and the highest levels present in the seed of transformed parental lines. Furthermore, the F2 seed comprise new cottonseed oils having different combinations of stearic acid and oleic acid content compared to untransformed cottonseed oil or individual transformed parental lines.

These results clearly demonstrated that the phenotypes observed for the transgenic parental lines are transmissible between generations, and can be combined in progeny plants. Accordingly, by selecting progeny plants which are homozygous for the introduced transgenes, and crossing those plants, elite lines containing elevated stearic acid and oleic acid, and having reduced levels of palmitic acid and linoleic acid, are obtained. Furthermore, crosses between elite lines which exhibit the highest levels of stearic acid and/or oleic acid, and the lowest levels of palmitic acid and/or linoleic acid, produces elite lines having the most desirable characteristics. Importantly, large scale intercrossing using parental lines produced as described herein, and having particular levels of individual fatty acids in their seed, is used to produce cotton seed having any desired level of palmitic acid, stearic acid, oleic acid, or linoleic acid, or a combination thereof, within the ranges observed in the parental lines. Accordingly, the present invention clearly provides a means by which cotton seed having the desirable POS fatty acid profile is produced, thereby providing a cotton seed oil substitute for cocoa butter.

EXAMPLE 19

Characterisation of Oils in Transgenic T2 Seed Containing Antisense of a Fatty Acid Δ9 Desaturase (Stearoyl-ACP Δ9-Desaturase) Gene Transgenic cotton having the fatty acid Δ9-desaturase antisense gene construct (Example 11) were analysed as described in the preceding examples for fatty acid composition. Data are presented in Table 16.

Increased Stearic Acid

Expression of the ghSAD-1 cDNA in the antisense orientation in cotton appeared to decrease the level of the stearoyl-ACP Δ9-desaturase enzyme activity in cotton, as suggested by the elevated level of stearic acid in transgenic T2 seed, particularly in line 9A-90. As summarised in Table 16, only one line of the total 25 transgenic lines generated produced seed having elevated stearic acid when compared to isogenic wild-type seed. Stearic acid was increased up to 28.2% of total seed lipid in line 9A-90 (Table 16).

Decreased Oleic Acid

Oleic acid was reduced in line 9A-90, from about 14.5% of total seed lipid in the non-transgenic cotton, to only 6.3% of total seed lipid.

Decreased Linoleic Acid

Linoleic acid was also reduced, from about 55% of total seed lipid in the non-transgenic line, to 46.2% in line 9A-90.

Decreased Palmitic Acid

Unexpectedly, and favorably, palmitic acid was significantly reduced in the T2 seed of transgenic cotton, particularly in line 9A-90. In particular, the level of palmitic acid in the seed of line 9A-90 was reduced to only 17.7% of total seed lipid in line 9A-90, compared to about 26% of total seed lipid for isogenic non-transformed plants.

TABLE 16

Fatty acid contents of T1 transgenic cotton comprising an antisense of a fatty acid Δ9-desaturase (stearoyl-ACP Δ9-desaturase) gene

| Plant line | Fatty acid composition (%) | | | | | |
|---|---|---|---|---|---|---|
| | Palmitic | Stearic | Oleic | Linoleic | Linolenic | SDP |
| 9A-118 | 26.7 | 2.0 | 15.8 | 55.2 | 0.1 | 0.97 |
| 9A-163 | 26.0 | 2.0 | 14.2 | 56.5 | 0.2 | 0.97 |
| 9A-38 | 27.0 | 2.2 | 14.0 | 56.4 | 0.3 | 0.97 |
| 9A-92 | 26.2 | 2.3 | 13.6 | 57.5 | 0.2 | 0.97 |
| 9A-9 | 25.2 | 2.3 | 13.6 | 58.5 | 0.1 | 0.97 |
| 9A-57 | 23.9 | 2.3 | 18.1 | 55.3 | 0.2 | 0.97 |
| 9A-127 | 24.2 | 2.4 | 15.2 | 57.8 | 0.2 | 0.97 |
| 9A-107 | 24.6 | 2.4 | 16.1 | 56.5 | 0.2 | 0.97 |
| 9A-148 | 24.2 | 2.4 | 15.1 | 57.9 | 0.1 | 0.97 |
| 9A-189 | 23.8 | 2.5 | 15.2 | 58.2 | 0.1 | 0.97 |
| 9A-89 | 23.8 | 2.5 | 15.7 | 57.5 | 0.2 | 0.97 |
| 9A-192 | 26.2 | 2.5 | 14.0 | 57.0 | 0.1 | 0.97 |
| 9A-14 | 28.5 | 2.4 | 14.9 | 53.9 | 0.1 | 0.97 |
| 9A-6 | 21.9 | 2.7 | 14.0 | 60.9 | 0.2 | 0.97 |
| 95-7 | 23.4 | 2.7 | 15.1 | 58.4 | 0.2 | 0.97 |
| 9A-2 | 23.6 | 2.5 | 14.0 | 59.6 | 0.1 | 0.97 |
| 9A-49 | 25.6 | 2.8 | 14.8 | 56.5 | 0.0 | 0.96 |
| 9A-81 | 24.2 | 2.8 | 14.4 | 58.1 | 0.2 | 0.96 |
| 9A-80 | 25.9 | 2.8 | 14.4 | 56.5 | 0.2 | 0.96 |
| 9A-150 | 22.9 | 3.2 | 15.4 | 58.1 | 0.1 | 0.96 |
| 9A-95 | 23.2 | 3.4 | 12.7 | 60.4 | 0.1 | 0.96 |
| 9A-183 | 24.3 | 3.4 | 14.2 | 57.6 | 0.2 | 0.96 |
| 9A-74 | 25.6 | 3.7 | 15.0 | 55.3 | 0.1 | 0.95 |
| 9A-28 | 21.8 | 5.4 | 12.4 | 60.0 | 0.1 | 0.93 |
| 9A-90 | 17.7 | 28.2 | 6.3 | 46.2 | 0.2 | 0.65 |

EXAMPLE 20

Characterisation of Oils in Transgenic T2 Seed Containing Antisense of a Fatty Acid Δ12 Desaturase (Oleoyl-PC Δ12-Desaturase) Gene Transgenic cotton having the fatty acid Δ12-desaturase antisense gene construct (Example 11) were analysed as described in the preceding examples for fatty acid composition. Data are presented in Table 17.

Increased Oleic Acid

In five (5) of the total twenty five (25) transgenic lines carrying the ghFAD2-1 cDNA in the antisense orientation, the level of oleic acid was increased to greater than 30% of total seed lipid (Table 17). The oleic acid content increased from about 14% for non-transformed Coker cotton, to as much as 74.4% of total seed lipid for the transgenic line 12A-87.

Decreased Linoleic Acid

Linoleic acid was reduced in transgenic cotton lines, from about 60% of total seed lipid in the non-transgenic Coker cotton, to only about 5.0% in line 12A-87.

Decreased Palmitic Acid

Unexpectedly, and favorably, palmitic acid was significantly reduced in the T2 seed of transgenic cotton containing the antisense gene construct. The level of palmitic acid in the seed bf transgenic plants was reduced to only 18.3% of total seed lipid in line 12A-87, compared to about 26% of total seed lipid for isogenic non-transformed plants.

TABLE 17

Fatty acid contents of T1 transgenic cotton comprising an antisense of a fatty acid Δ12-desaturase (oleoyl-PC Δ12-desaturase) gene

| Plant line | Fatty acid composition (%) | | | | | |
|---|---|---|---|---|---|---|
| | Palmitic | Stearic | Oleic | Linoleic | Linolenic | ODP |
| 12A-30 | 23.4 | 2.6 | 13.2 | 60.3 | 0.2 | 0.82 |
| 12A-73 | 24.5 | 2.6 | 13.3 | 59.2 | 0.1 | 0.82 |
| 12A-124 | 24.7 | 2.8 | 13.7 | 58.4 | 0.2 | 0.81 |
| 12A-41 | 25.2 | 2.5 | 13.8 | 58.1 | 0.2 | 0.81 |
| 12A-60 | 22.9 | 2.6 | 14.4 | 59.6 | 0.2 | 0.81 |
| 12A-33 | 25.3 | 2.1 | 14.4 | 57.9 | 0.2 | 0.80 |
| 12A-111 | 26.1 | 2.5 | 14.2 | 56.7 | 0.2 | 0.80 |
| 12A-74 | 23.7 | 2.4 | 14.8 | 58.7 | 0.1 | 0.80 |
| 12A-84 | 24.0 | 2.6 | 14.9 | 58.0 | 0.2 | 0.80 |
| 12A-130 | 24.4 | 3.0 | 14.9 | 57.3 | 0.2 | 0.79 |
| 12A-59 | 24.6 | 2.2 | 15.1 | 57.7 | 0.2 | 0.79 |
| 12A-68 | 25.4 | 2.8 | 15.4 | 56.1 | 0.1 | 0.79 |
| 12A-85 | 27.8 | 2.4 | 16.2 | 53.1 | 0.2 | 0.77 |
| 12A-81 | 26.2 | 2.0 | 16.9 | 54.9 | 0.0 | 0.76 |
| 12A-48 | 22.2 | 2.5 | 17.8 | 57.3 | 0.1 | 0.76 |
| 12A-32 | 25.7 | 2.1 | 17.1 | 54.8 | 0.2 | 0.76 |
| 12A-132 | 24.7 | 2.2 | 21.4 | 51.3 | 0.1 | 0.71 |
| 12A-126 | 25.6 | 2.0 | 28.2 | 43.7 | 0.2 | 0.61 |
| 12A-1 | 21.1 | 3.5 | 29.7 | 45.2 | 0.2 | 0.60 |
| 12A-83 | 23.0 | 2.5 | 30.5 | 43.8 | 0.1 | 0.59 |
| 12A-118 | 23.9 | 2.0 | 34.5 | 39.6 | 0.0 | 0.53 |
| 12A-86 | 22.1 | 2.0 | 42.6 | 32.8 | 0.2 | 0.44 |
| 12A-14 | 19.7 | 2.1 | 72.4 | 5.4 | 0.1 | 0.07 |
| 12A-87 | 18.3 | 1.9 | 74.4 | 5.0 | 0.1 | 0.06 |

REFEREMCES

1. Auld, D. L., M. K. Heikkinen, D. A. Erickson, J. L. Sernyk J. E. Romero (1992). Rapeseed mutants with reduced levels of polyunsaturated fatty acids and increased levels of oleic acid, *Crop Sci.* 32, 657–662.
2. Akagi, H., Baba, T., Shimada, H., Fujimura, T. (1995). Nucleotide sequence of a stearoyl-acyl carrier protein desaturase cDNA from developing seeds of rice. *Plant Physiol.* 108: 845–846.
3. Allen, E., Johnson, A. R., Fogerty, A. C., Pearson, J. A., Shenstone, F. S. (1967). Inhibition by cyclopropene fatty acids fo the desaturation of stearic acid in hen liver. *Lipids* 2: 419–423.
4. Arondel, V., Lemieux, B., Hwang, I., Gibson, S., Goodman, H. M., Somerville, C. R. (1992). Map-based cloning of a gene controlling Omega-3 fatty acid desaturation in *Arabidopsis. Science* 258: 1353–1355.
5. Auld, D. L., Heikkinen, M. K., Erickson, D. A., Sernyk, J. L. and Romero, J. E. (1992). Rapeseed mutants with reduced levels of polyunsaturated fatty acids and increased levels of oleic acid. *Crop Sci.* 32: 657–662.
6. Baerson, S. R., Lamppa, G. K. (1993). Developmental regulation of an acyl carrier protein gene promoter in vegetative and reproductive tissues. *Plant Molecular Biology* 22: 255–267.
7. Bafor, M., Stobart, A. K. and Stymne, S. (1990). Properties of the glycerol acylating enzymes in microsomal preparations from the developing seeds of safflower (*Carthamus tinctorius*) and turnip (*Brassica campestris*) and their ability to assmble cocoa-butter type fats. *JAOCS* 67(4): 217–225.
8. Baize, J. C. (1997). Oilseed industry's evolution and future. *INFORM* 8: 498–510.
9. Baldoni, L., Georgi, L. L., and Abbott, A. G. (1996). Nucleotide sesquence of a cDNA clone from *Olea europeaea* encoding a stearoyl-acyl carrier protein desaturase (Accession No. U58141). *Plant Physiol.* 111: 1353.
10. Bligh, E. G., and Dyer, W. J. (1959). A rapid method of total lipid extraction and purification. *Canadian Journal of Biochemistry and Physiology* 37(8): 911–917.
11. Bourque, J. E. (1995). Antisense strategies for genetic manipulations in plants. *Plant Science* 105: 125–149.
12. Broun, P., Boddupalli, S. and Somerville, C. (1998). A bifunctional oleate 12-hydroxylase: desaturase from *Lesquerella fendleri. The Plant Journal* 13: 201–210.
13. Brown, L. C. and Kurtz, E. B. (1959). The in vitro synthesis of fats in cottonseed. *Agronomy J.* 51: 49–50.
14. Browse, J. and Somerville, C. (1995). Glycerolipids. In: Meyerowitz, E. and Somerville, C. (Eds.), *Arabidopsis* (pp. 881–912). Cold Spring Harbor Laboratory Press, New York.
15. Cahoon, E. B., Becker, C. B., Shanklin, J. and Ohlrogge, J. B. (1994). cDNAs for isoforms of the Δ9-stearoyl-acyl carrier protein desaturase from *Thunbergia alata* endosperm. *Plant Physiol.* 106: 807–808.
16. Cahoon, E. B., Coughlan, S. J., Shanklin, J. (1997). Characterization of a structurally and functionally diverged acyl-acyl carrier protein desaturase form milkweed seed. *Plant Molecular Biology* 33: 1105–1110.
17. Cahoon, E. B., Coughlan, S. J., Shanklin, J. (1997). Characterization of a structurally and functionally diverged acyl-acyl carrier protein desaturase form milkweed seed. *Plant Molecular Biology* 33: 1105–1110.
18. Cahoon, E. B., Shanklin, J. and Ohlrogge, J. B. (1992). Expression of a coriander desaturase results in petroselinic acid production in transgenic tobacco. *Proc. Natl. Acad. Sci. USA* 89: 11184–11188.
19. Cahoon, E. B., Lindqvist, Y., Schneider, G. and Shanklin, J. (1997b). Redesign of soluble fatty acid desaturases from plants for altered substrate specificity and double bond position. *Proc. Natl. Acad. Sci. USA* 94: 4872–4877.
20. Cahoon, E. B., Carlson, T. J., Ripp, K. G., Schweiger, B. J., Cook, G. A., Hall, S. E. and Kinney, A. J. (1999). Biosynthesis origin of conjugated double bonds: production of fatty acid components of high-value drying oils in transgenic soybean embryo. *PNAS* 96; 12935–12940.
21. Cahoon, E. B., Marillia, E-F., Stecca, K. L., Hall, S. E., Taylor, D. C. and Kinney, A. J. (2000). Production of fatty acid composition of meadowfoam oil in somatic soybean embryos. *Plant Physiol.* 124: 243–251.
22. Cartea, M. E., Migal, M., Galle, A. M., Pelletier, G. and Guerche, P. (1998). Comparison of sense and antisense methodologies for modifying the fatty acid composition of *Arabidopsis thaliana* oilseed. *Plant Science* 136: 181–194.

23. Carter, F. L., Castillo, A. E., Frampton, V. L., Kerr, T. (1966). Chemical composition studies of seeds of the genus *Gossypium. Phytochemistry* 5: 1103–1112.
24. Chen, L. J. and Moon, Y. (1995). Cloning and sequence of a cDNA encoding stearoyl-acyl-carrier-protein desaturase (accession No. L34346) from *Glycine max. Plant Physiol.* 109: 1498.
25. Cherry, J. P. (1 983). Cottonseed oil. *J. Am. Oil Chem. Soc.* 60(2): 360–367.
26. Cherry, J. P., Leffler, H. R. (1984). Seed. In: Cotton. (R. J. Kohel, Lewis, C. F., eds) Madison, Wis., USA, American Society of Agronomy, Inc., Crop Science Society of America, Inc., Soil Science Society of America, Inc., Publishers: pp 511–569.
27. Cho, M.-J., Widholm, J. M., Vodkin, L. O. (1995). Cassettes for seed-specific expression tested in transformed embryogenic cultures of soybean. *Plant Molecular Biology Reporter* 13: 255–269.
28. Cousins, Y. L., Lyon, B. R. and Llewellyn, D. J. (1991). Transformation of an Australian cotton cultivar: prospects for cotton improvement through genetic engineering. *Aust. J. Plant Physiol.* 18: 481–494.
29. Devereux, J., Haeberli, P. and Smithies, O. (1984). A comprehensive set of sequence analysis progenitor programs for the VAX. *Nucl. Acids Res.* 12: 387–395.
30. Elmore, C. D. and Leffler, H. R. (1976). Development of cotton fruit. III. Amino acid accumulation in protein and nonprotein nitrogen fractions of cottonseed. *Crop Sci.* 16: 867–871.
31. EI-Nockrashy, A. S., Simmons, J. G., Frampton, V. L. (1969). A chemical survey of seeds of the genus *Gossypium. Phytochemistry* 8: 1949–1958.
32. Erickson, E. A., J. R. Wilcox and J. F. Canvins (1988). Inheritance of altered palmitic acid percentage in two soybean mutants. *J. Hered.* 79, 465–468
33. Endrizzi, J. E., Turcotte, E. L. and Kohel, R. J. (1985). Genetics, cytology, and evolution of *Gossypium. Adv. Genet.* 23: 271–375.
34. Erickson, E. A., J. R. Wilcox and J. F. Canvins (1988). Inheritance of altered palmitic acid percentage in two soybean mutants. *J. Hered.* 79: 465–468.
35. Falcone, D. L., Gibson, S., Lemieux, B., Somerville, C. (1994). Identification of a gene that complements an *Arabidopsis* mutant deficient in chloroplast w6 desaturase activity. *Plant Physiol.* 106: 1453–1459.
36. Fehr, W. R., G. A. Welke, E. G. Hammond, D. N. Duvick and S. R. Cianzio (1991). Inheritance of reduced palmitic acid content in seed oil of soybean. *Crop Sci.* 31, 88–89
37. Feinberg, A. P. and Vogelstein, B. (1983). A technique for radiolabeling DNA restriction fragments to high specific activity. *Anal. Biochem.* 132: 6–13.
38. Fincke, A. (1976). Untersuchungen zur fetts äurezusammensetzung von kakaobutter. *Gordian* 76: 324.
39. Fisher, G. S., Cherry, J. P. (1983). Variation of cyclopropenoid fatty acids in cottonseed lipids. *Lipids* 18(9): 589–594.
40. Fisher, G. S., Schuller, W. H. (1981). Gas chromatographic analysis of cyloproprenoid acids in cottonseed oils. *J. Am. Oil Chem. Soc.* 58: 943–947.
41. Folch, J., Lees, M. and Stanley, G. H. S. (1957). A simple method for the isolation and purification of total lipids from animal tissues. *J. Biol. Chem.* 226: 497.
42. Fox, B. G., Shaklin, J., Somerville, C., Munck, E. (1993). Stearoyl-acyl carrier protein Δ9 desaturase from *Ricinus communis* is a diiron-oxo protein. *Proc. Natl. Acad. Sci. USA* 90: 2486–2490.
43. Fox, B. G., Shanklin, J., Ai, J., Loehr, T. M., Sanders-Loehr, J. (1994). Resonance raman evidence for an Fe—O—Fe center in stearoyl-ACP desaturase. Primary sequence identity with other Diiron-oxo proteins. *Biochemistry* 33: 12776–12786.
44. Gamborg, O., Miller, R. A. and Ojima, K. (1968). Nutrient requirements of suspension cultures of soybean root cells. *Expermental Cell Research* 50: 151–158.
45. Gavel, Y. and von Heijne, G. (1990) A conserved cleavage-site motif in chloroplast transit peptides. *FEBS Lett.* 261: 455–458.
46. Graef, G. L., Fehr, W. R. and Hammond, E. G. (1985). Inheritance of three stearic acid mutants of soybean. *Crop Sci.* 25: 1076–1079.
47. Grayburn, W. S., Collins, G. B. and Hildebrand, D. F. (1992). Fatty acid alteration by a Δ9 desaturase in transgenic tobacco tissue. *Bio/Technology* 10: 675–678.
48. Green, A. G. (1986a). A mutant phenotype of flax (*Linus usitatissamum L.*) containing very low levels of linolenic acid in its seed oil. *Can. J. Plant Sci.* 66: 499–503.
49. Green, A. G. (1986b). Genetic control of polyunsaturated fatty acid biosynthesis in Flax (*Linum usitatissimum*) seed oil. *Theor. Appl. Genet.* 72: 654–661.
50. Green, A. G., N. B. Hulse and M. L. Tonnet (1991). Genetic modification of fatty acid composition in flax. *INFORM* 2(4) p 316
51. Gunstone, F. D., Harwood, J. L. and Padley, F. B. (1986). The Lipid Handbook. Chapman and Hall, eds.
52. Gurr, M. I., Robinson, M. P. and James, A. T. (1969). Mechanism of formation of polyunsaturated fatty acids by photosynthetic tissue. *Eur. J. Biochem.* 9: 70–78.
53. Hamilton, A. J., Brown, S., Yuanhai, H., Ishizuka, M., Lowe, A., Alpuche Solis, A-G. and Grierson, D. (1998). A transgene with repeated DNA causes high frequency, post-transcriptional suppression of ACC-oxidase gene expression in tomato. *The Plant Journal* 15(6), 737–746.
54. Harvey, B. L. and Downey, R. K. (1964). The inheritance of erucic acid content in rapeseed (*Brassica napus*). *Can. J. Plant Sci.* 44: 104–111.
55. Hawkins and Kridl, J. C. 1998; Characterisation of acyl-ACP thioesterases of mangosteen (*Garcinia mangostana*) seed and high levels of stearate production in transgenic canola. *The Plant Journal* 13: 743–752).
56. Heinkoff, S. and Dressen, T. D. (1989). Trans-inactivation of the *Drosophila* Brown Gene: evidence for transcriptional repression and somatic pairing dependence. *Proc. Natl. Acad. Sci. USA* 86-6704–6708.
57. Heppard, E. P., Kinney, A. J., Stecca, K. L., Miao, G. H. (1996). Developmental and growth temperature relation of two different microsomal ω-6 desaturase genes in soybeans. *Plant Physiol.* 110: 311–319.
58. Hlousek-Radojcic, A., Post-Beittenliller, D. and Ohlrogge, J. B. (1992). Expression of constitutive and tissue-specific acyl carrier protein isoforms in *Arabidopsis. Plant Physiol.* 98(1): 206–214.
59. Ivanov, P., Petkov, D., D., Nikolova, V. and Petchev, E. (1988). Sunflower breeding for high palmitic acid content in the oil. In: Proc. 12th Int. sunflower Conf., Nov Sad, Yugoslavia, Int. Sunflower Assoc. Toowoomba, Australia.
60. Jackson, M. R., Nilsson, T. and Peterson, P. A. (1990). Identification of a consensus motif for retention of transmembrane proteins in the endoplasmic reticulum. *EMBO J.* 9. 3153–3162.
61. Jain, R. K., Thompson, R. G., Taylor, D. C., MacKenzie, S. L., McHughen, A., Rowland, G. G., Tenaschuk, D. and Coffey, M. (1999). Isolation and characterisation of two promoters from linseed for genetic engineering. *Crop Sci.* 39: 1696–1701.
62. James, D. W., Jr.; Dooner, H. K. (1990). Isolation of EMS-induced mutants in *Arabidopsis* altered in seed fatty acid composition. *Theor. Appl. Genet.* 80(2): 241–245.

63. Jaworski, J. G. and Stumpf, P. K. (1974). Properties of a soluble stearoyl-acyl carrier protein desaturase from maturing safflower. *Arch. Biochem. Biophys.* 162: 158–165.
64. Jennings, M. L. (1989). Topography of membrane proteins. *Annu. Rev. Biochem.* 58: 999–1027.
65. Khattab, A. H., Khalifa, H., EI Tinay, A. H. (1977). Chemical composition of seeds of some species of the genus *Gossypium*. *J. Agri. Sci. Camb.* 88: 55–59.
66. King, E. E. and Leffler, H. R. (1979). Nature and patterns of proteins during cotton seed development. *Plant Physiol.* 63: 260–263.
67. Kinney, A. J. (1996). Designer oils for better nutrition. *Nature Biotechnology* 14: 946.
68. Kinney, A. J., Hitz, W. D., Knowlton, S. and Cahoon, E. B. (1998). Re-engineering oilseed crops to produce industrially useful fatty acids. *Advances in Plant Lipid Research.* J. Sanchez, Cerda-Olmedo, E. and Martinez-Force, E. Sevilla, Spain, University de Sevilla: 623–628.
69. Kinney, A. J. (1995). Improving soybean seed quality. In: *Induced Mutations and Molecular Techniques for Crop Improvement* (pp. 101–113). IAEA and FAO, Vienna.
70. Kinney, A. J., Hirtz, W. D. and Yadav, N. S. (1990). Stearoyl-ACP desaturase and a β-ketoacyl-ACP acyl carrier protein synthase I isozyme from barley. In: Quinn, P. J. and Harwood, J. L. (Eds.), *Plant Lipid Biochemistry, Structure and Utilisation* (pp. 126–128). Portland Press, London.
71. Kinney, A. J. (1996) Development of genetically engineered oilseeds. Physiology, Biochemistry and, Molecular Biology of Plant Lipids (Williams, J. P., Khan, M. U. and Lem, N. W. eds) Kluwer Academy Publishers (Dordrecht/Boston/London). p 298–300.
72. Knowles, P. (1989). Genetics and breeding of oil crops. In: Röbbelen, G., Downey, R. K. and Ashri, A. (Eds.), *Oil Crops of the World* (pp. 260–282). McGraw Hill, N.Y.
73. Knutzon, D. S., Scherer, D. E. and Schreckengost, W. E. (1991). Nucleotide sequence of a complementary DNA clone encoding stearoyl-acyl carrier protein desaturase form castor bean, *Ricinus communis*. *Plant Physiol.* 96: 344–345.
74. Knutzon, D. S., Thompson, G. A., Radke, S. E., Johnson, W. B., Knauf, V. C. and Kridl, J. C. (1992). Modification of *Brassica* seed oil by antisense expression of a stearoyl-acyl carrier protein desaturase gene. *Proc. Natl. Acad. Sci. USA* 89: 2624–2628.
75. Knutzon, D. S., Thompson, G. A., Radke, S. E., Johnson, W. B., Knauf, V. C. and Kridl, J. C. (1992b). Modification of *Brassica* seed oil by antisense expression of a stearoyl-acyl carrier protein desaturase gene. *Proc. Natl. Acad. Sci. USA* 89: 2624–2628.
76. Lassner, M. W., Lardizabal, K., Metz, J. G. (1996). A jojoba b-ketoacyl-CoA synthase cDNA complements the canola fatty acid elongation mutation in transgenic plants. *The Plant Cell* 8: 281–292.
77. Lemineux, B., Miquel, M., Somerville, C. R. and Browse, J. (1990). Mutants of *Arabidopsis* with alterations in seed lipid fatty acid composition. *Theor. Appl. Genet.* 80: 234–240.
78. Lindqvist, Y., Huang, W., Schneider, G. and Shanklin, J. (1996). Crystal structure of Δ9 stearoyl-acyl carrier protein desaturase from castor seed and its relationship to other di-iron proteins. *EMBO J.* 15: 4081–4092.
79. Liu, Q., Singh, S. P., Brubaker, C. L. and Green, A. G. (1999). Cloning and sequence analysis of a novel member (accession No. Y10112) of the microsomal w-6 fatty acid desaturase family from cotton (*Gossypium hirsutum*). *Plant Physiol.* 120: 339.
80. Liu, Q., Singh, S. P., Brubaker, C. L., Sharp, P. J., Green, A. G. and Marshall, D. R. (1999). Molecular cloning and expression of a cDNA encoding a microsomal w-6 fatty acid desaturase in cotton (*Gossypium hirsutum L.*). *Australian Journal of Plant Physiology* 26: 101–106.
81. Liu, Q., Brubaker, C. L., Green, A. G., Sharp, P. J., Marshall, D. R. and Singh, S. P. (2000). Microsomal fatty acid desaturase gene intron topologies contribute to our understanding of reticulate evolution in *Gossypium* (Malvaceae) and the evolution of the Australian *Gossypium* species. *American Journal of Botany* (In press).
82. Liu, Q., Singh, S. P., Sharp, P. J., Green, A. G. and Marshall, D. R. (1996). Nucleotide sequence of a cDNA from *Gossypium hirsutum* encoding a stearoyl-acyl carrier protein desaturase (accession No. X95988) (OGR 96-012). *Plant Physiol.* 110: 1435.
83. Matzke, M. A. and Matzke, A. J. M. (1995). How and why do plants inactivate homologous (trans)genes? *Plant Physiol.* 107. 679–685.
84. McKeon, T. A., and Stumpf, P. K. (1982). Purification and characterisation of the stearoyl-acyl carrier protein desaturase and the acyl-acyl carrier protein thioesterase from maturing seeds of safflower. *The Journal of Biological Chemistry* 257(20): 12141–12147.
85. Mekhedov, S., de Harduya, O. M. and Ohlrogge, J. (2000). Toward a functional catalog of the plant genome. A survey of genes for lipid biosynthesis. *Plant Physiol.* 122: 389–401.
86. Meyer, P. and Saedler, H. (1996). Homology-dependent gene silencing in plants. *Annu. Rev. Plant Physiol. Plant Mol. Biol.* 47: 23–48.
87. Miller, J. F., Zimmerman, D. C. and Vick, B. A. (1987). Genetic control of high oleic acid content in sunflower oil. *Crop Sci.* 27: 923–926.
88. Miquel, M. F., Browse, J. A. (1994). High-oleate oilseeds fail to develop at low temperature. *Plant Physiol.* 106: 421–427.
89. Miquel, M., and Browse, J. (1992). *Arabidopsis* mutants deficient in polyunsaturated fatty acid synthesis: Biochemical and genetical characterisation of a plant oleoyl-phosphatidylcholine desaturase. *The Journal of Biological Chemistry* 267(3): 1502–1509.
90. Miquel, M., James Jr., D., Dooner, H. and Browse, J. (1993). *Arabidopsis* requires polyunsaturated lipids for low-temperature survival. *Proc. Natl. Acad. Sci. USA* 90: 6208–6212.
91. Murashige, T. and Skoog, F. (1962). A revised medium for rapid growth and bioassay with tobacco cultures. *Physiologica Plantarum* 15: 473–497.
92. Neidleman, S. L. (1987). Effects of temperature on lipid unsaturation. *Biotechnol. Genet. Eng. Rev.* 5: 245–268.
93. Nichols, B. W. (1969). The separation, structure and metabolism of monogalactosyl diglyceride species in *Chlorella vulgaris*. *Lipids* 3: 354–360.
94. Nichols, B. W., James, A. T. and Breuer, J. (1967). Interrelationships between fatty acid biosynthesis and acyl-lipid synthesis in *Chlorella vulgaris*. *Biochem. J.* 104: 486–496.
95. Nishida, I., Beppu, T., Matsuo, T. and Murata, N. (1992). Nucleotide sequence of a cDNA clone encoding a precursor to stearoyl-(acyl-carrier-protein) desaturase from spinach, *Spinacia oleracea*. *Plant Molecular Biology* 19: 711–713.
96. Nordlund, P., Sjöberg, B.-M. and Eklund, H. (1993). Three-dimensional structure of the free radical protein of ribonucleotide reductase. *Nature* 345: 592–598.
97. Ohlrogge, J. B., Browse, J. and Somerville, C. R. (1991). The genetics of plant lipids. *Biochimica et Biophysica Acta* 1082: 1–26.

98. Osorio, J., Fernandez-Martinez, J., Mancha, M. and Garces, R. (1995). Mutant sunflowers with high concentration of saturated fatty acids in the oil. *Crop Sci.* 35, 739–742

99. Okuley, J., Lightner, J., Feldmann, K., Yadav, N., Lark, E. and Browse, J. (1994). Arabidopsis FAD2 gene encodes the enzyme that is essential for polyunsaturated lipid synthesis. *The Plant Cell* 6: 147–158.

100. Pandey, S. S., and Subrahmanyam, V. V. R. (1988). Lipid changes in maturing and germinating cottonseeds. *Phytochemistry* 27(11): 3405–3409.

101. Paterson, A. H., Brubaker, C. L. and Wendel, J. F. (1993). A rapid method for extraction of cotton (*Gossypium* spp.) genomic DNA sutiable for RFLP or PCR analysis. *Plant Molecular Biology Reporter* 11(2): 122–127.

102. Phelps, R. A., Shenstone, F. S., Kemmerer, A. R., and Evans, R. J. (1964). A review of cyclopropenoid compounds; biological effects of some derivatives. *Poultry Science* 44: 358–394.

103. Polashock, J. J., Chin, C. K., Martin, C. E. (1992). Expression of the yeast D-9 fatty acid desaturase in *Nicotiana tabacum*. *Plant Physiol.* 100: 894–901.

104. Purdy, R. H. J. (1986). High oleic sunflower, physical and chemical characteristics. *JAOCS* 63: 1062–1066.

105. Pirtle, R. M., Yoder, D. W., Huynh, T. T., Nampaisansuk, M., Pirtile, I. L. and Chapman, K. D. Characterisation of a palmitoyl-acyl carrier protein thioesterase (FatB1) in cotton. *Plant Cell Physiology* 40 (1999): 155–163.

106. Rahman, S. M., Takagi, Y., Kubota, K., Miyamoto, K. and Kawakita, T. (1994). High oleic acid mutant in soybean induced by X-ray irradiation. *Biosci. Biotech. Biochem.* 58: 1070–1072.

107. Rahman, S. M., Takagi, Y., Miyamoto, K. and Kawakita, T. (1995). High stearic soybean mutant induced by X-ray irradiation. *Biosci. Biotech. Biochem.* 59: 922–923.

108. Rattray, J. (1991). Plant biotechnology and the oils and fats industry. In: Rattray, J. (Ed.), Biotechnology of Plant Fats and Oils (pp. 1–35). *Am. Oil Chem. Soc.*, Champaign, Ill.

109. Resenberg, U. B., Preiss, A., Seifert, E., Jackie, H. and Knipple, D. C. (1985). Production of phenocopies by Kruppel antisense RNA injection into *Drosophila* embryos. *Nature* 313: 703–705.

110. Röbbelen, G. and Nitsch, A. (1975). Genetical and physiological investigations on mutants for polyenoic fatty acids in rapeseed, *Brassica napus L. I*. Selection and description of new mutants. *Z. Pflanzenzuchtg* 75: 93–105.

111. Röbbelen, G., Downey, R. K. and Ashri, A. (1989). *Oil Crops of the World*. McGraw-Hill, N.Y.

112. Rosenzweig, A. C., Frederick, C. A., Lippard, S. J. and Nordlund, P. (1993). Crystal structure of a bacterial non-haem iron hydroxylase that catalyses the biological oxidation of methane. *Nature* 366: 537–540.

113. Rowland, G. G. and Bhatty, R. S. (1990). Ethyl methanesulphonate induced fatty acid mutations in flax. *J. Am. Oil Chem. Soc.* 67: 213–214.

114. Sambrook, J., Fritsch, E. F. and Maniatis, T. (1989). *Molecular Cloning: A Laboratory Manual* (2nd ed.). Cold Spring Harbour Laboratory, Cold Spring Harbour, N.Y.

115. Sato, A., Becker, C. K. and Knauf, V. C. (1992). Nucleotide sequence of a complementary DNA clone encoding stearoyl-acyl carrier protein desaturase from *Simmondsia chinensis*. *Plant Physiol.* 99: 362–363.

116. Scarth, R., McVetty, P. B. E., Rimme, S. R. and Stefansson B. R. (1988). Stellar low-linolenic high-linoleic acid summer rape. *Can. J. Plant Sci.*, 68, 509–511

117. Scheffler, J. A., Sharpe, A. G., Schmidt, H., Sperling, P., Parkin, I. A. P., Luhs, W., Lydiate, D. J., and Heinz, E. (1997). "Desaturase multigene families of *Brassica napus* arose through genome duplication. *Theor. Appl. Genet.* 94: 583–591.

118. Schmidt, H., Dresselhaus, T., Buck, F. and Heinz, E. (1994). Purification and PCR-based cDNA cloning of a plastidial n-6 desaturase. *Plant Molecular Biology* 26: 631–642.

119. Schultz, D. J., Cahoon, E. B., Shanklin, J., Craig, R., Cox-Foster, D. L., Mumma, R. O. and Medford, J. I. (1996). Expression of a Δ9 14:0-acyl carrier protein fatty acid desaturase gene is necessary for the production of ω5 anacardic acids found in pest-resistant geranium (*Pelargonium xhortorum*). *Proc. Natl. Acad. Sci. USA* 93: 8771–8775.

120. Shah, F. H. and Rashid, O. (1996). Nucleotide sequence of a complementary DNA clone encoding stearoyl-acyl-carrier-protein (accession No. U68756) from *Elaeis guneensis* var. tenera. *Plant Physiol.* 112: 1399.

121. Shanklin, J., Mullins, C. and Somerville, C. (1991). Sequence of a complementary DNA from *Cucumis sativus L*. encoding the stearoyl-acyl-carrier-protein desaturase. *Plant Physiol.* 97: 467–468.

122. Shanklin, J., and Somerville, C. (1991). Stearoyl-acyl-carrier-protein desaturase from higher plants is structurally unrelated to the animal and fungal homologs. *Proc. Natl. Acad. Sci. USA* 88: 2510–2514.

123. Shanklin, J and Cahoon, E. B. (1998). Desaturation and related modification of fatty acids. *Annu. Rev. Plant Physiol. Plant Mol. Biol.* 49: 611–41.

124. Singh, S., McKinney, S. and Green, A. (1994). Sequences of a cDNA from *Linum usitatissimum* encoding the stearoyl-Acyl carrier protein desaturase. *Plant Physiol.* 104: 1075.

125. Slabaugh, M., Leonard, J., Tai, J., Jaworski, J. and Knapp, S. (1993). Condensing enzymes and thioesterase expressed in immature embryos of *Cuphea wrightii*. In: *The Proceedings of Plant Lipid Symposium*, Minneapolis, Minn.

126. Slocombe, S. P., Cummins, I., Jarvis, R. P. and Murphy, D. J. (1992). Nucleotide sequence and temporal regulation of a seed-specific *Brassica napus* cDNA encoding a stearoyl-acyl carrier protein (ACP) desaturase. *Plant Molecular Biology* 20: 151–155.

127. Slocombe, S. P., Piffanelli, P., Fairbairn, d., Bowra, S., Hatzopoulos, P., Tsiantis, M. and Murphy, D. J. (1994). Temporal and tissue-specific regulation of a *Brassica napus* stearoyl-acyl carrier protein desaturase gene. *Plant Physiol.* 104: 1167–1176.

128. Smith, M. A., Cross, A. R., Jones, O. T. G., Griffiths, W. T., Stymne, S. and Stobart, K. (1990). Electron-transport components of the 1-acyl-2-oleoyl-sn-glycero-3-phosphocholine delta12-desaturase (Δ12-desaturase) in microsomal preparations from developing safflower (*Carthamus tinctorius L*.) cotyledons. *Biochem. J.* 272: 23–29.

129. Soldatov, K. I. (1976). Chemical mutagenesis in sunflower breeding. pp 352–357. In Proc. $7_{th}$ Int. Sunflower Conf., Krasnodar, USSR. 27 June ☐ 3. July International Sunflower Association. Vlaardingen, The Netherlands.

130. Stanton, J. M. and Blumenfeld, J. K. (1992). Modifying oil yield affects profile too. *INFORM* 3; 1019–1022.

131. Stefansson, B. R., Hougen, F. W. and Downey, R. K. (1961). Note on the isolation of rape plants with seed oil free from erucic acid. *Can. J. Plant Sci.* 41: 218–219.

132. Stewart, J. M., Hsu, C. L. (1977). In ovulo embryo culture and seedling development of cotton (*Gossypium hirsutum* L.). *Planta* 137 113–117.
133. Stukey, J. E., McDonough, V. M. and Martin, C. E. (1990), The OLE1 gene of *Saccharomyces cerevisiae* encodes the delta 9 fatty acid desaturase and can be functionally replaced by the rat stearoyl-CoA desaturase gene. *The Journal of Biological Chemistry* 265(33): 20144–20149.
134. Stymne, S. and Appelqvist, L. A. (1978). The biosynthesis of linoleneate from oleoyl-CoA via oleoyl-phosphatidyicholine in microsomes of developing safflower seeds. *Eur. J. Biochem.* 90; 223–247.
135. Stymne, S. and Appelqvist, L. A. (1980). Biosynthesis of linoleate and linoleneate in homogenates from developing soya bean cotyledons. *Plant Sci. Left.* 17: 287–294.
136. Taylor, M. A., Smith, S. B., Davies, H. V. and Burch, L. R. (1992). The primary structure of a cDNA clone of the stearoyl-acyl carrier protein desaturase gene from potato (*Solanum tubernsum* L.). *Plant Physiol.* 100: 533–534.
137. Thiede, M. A., Ozoles, J. and Strittmatter, P. (1 985). The induction and characterisation of cDNA for rat liver stearoyl-CoA desaturase mRNA. *J. Biol. Chem.* 260: 14459–14463.
138. Thompson, G. A., Scherer, D. E., Aken, S. F., Kenny, J. W., Young, H. L., Shintani, D. K., Kridl, J. C. and Knauf, V. C. (1991). Primary structures of the precursor and mature forms of stearoyl-acyl carrier protein desaturase from safflower embryos and requirement of ferredoxin for enzyme activity. *Proc. Natl. Acad. Sci. USA* 88: 2578–2582.
139. Thompson, G. A., Scherer, D. E., Aken, S. F., Kenny, J. W., Young, H. L., Shintani, D. K., Kridl, J. C. and Knauf, V. C. (1991). Primary structures of the precursor and mature forms of stearoyl-acyl carrier protein desaturase from safflower embryos and requirement of ferredoxin for enzyme activity. *Proc. Natl. Acad. Sci. USA* 88: 2578–2582.
140. Topfer, R., Martini, N., and Schell, J. (1995). Modification of plant lipid synthesis. *Science* 268: 681–686.
141. Touma-Touchan, H. (1977). Etudes biochimiques et ultrastructurales des lipides dans la graine du cotonnier. *J. Ultrastruct Res.* 58: 271–288.
142. van der Krol, A. R., Lenting, P. E., Veenstra, J., van der Meer, I. M., Koes, R. E., Gerats, A. G. M., Mol, J. N. M. and Stuitje, A. R. (1988). An anti-sense chalone synthase gene in transgenic plants inhibits flower pigmentation. *Nature* 333: 866–869.
143. Vodkin, L. O., Rhodes, P. R. and Goldberg, R. B. (1983) cA lectin gene insertion has the structural features of a transposable element. *Cell* 34(3): 1023–31.
144. Voelker, T. Plant acyl-ACP thioesterase: chain-length determining enzymes in plant fatty acid biosynthesis, In: J. K. Setlow (Ed.) *Genetic Engineering,* vol. 18, Plenum Press, New York, 1996, pp. 111–133.
145. Waterhouse, P. M., Graham, M. W. and Wang, M-B. (1998). Virus resistance and gene silencing in plants can be induced by simultaneous expression of sense and antisense RNA. *Proc. Natl. Acadl. Sci. USA* 95: 3959–13964.
146. Wendel, J. F. and Albert, V. A. (1992). Phylogenetics of the cotton genus (*Gossypium*): Character-state weighted parsimony analysis of chloroplast-DNA restriction site data and its systematic and biogeographic implications. *Syst. Bot.* 17: 115–143.
147. Wilcox, J. R., Cavins, J. F. and Nielsen, N. C. (1984). Genetic alteration of soybean oil composition by a chemical mutagen. *J. Am. Oil Chem. Soc.* 61: 97–100.
148. Wissenbach, M., Siggaard-Andersen, M., Kauppinen, S. and von Wettstein-Knowles, P. (1992). Condensing enzymes of barley. In: Cherif, A., Ben Miles-Daoud, D., Marzouk, B., Smaoui, A. and Zarouk, M. (Eds.), *Metabolism Structure and Utilisation of Plant Lipids* (pp. 393–396). Centre National Pélagogique, Tunis.
149. Wollett, L. A. and Dietshy, J. M. (1994). Effect of long-chain fatty acids on low-density lipoprotein cholesterol metabolism. *Amer. J. Clin. Nutr.* 60: 991–996.
150. Yadav, N. S., Wierzbicki, A., Aegerter, M., Caster, C. S., Perez-Grau, L., Kinney, A. J., Hiltz, W. D., Booth Jr, R., Schweiger, B., Stecca, K. L., Allen, S. M., Blackwell, M., Reiter, R. S., Carlson, T. J., Russell, S. H., Feldmann, K. A., Pierce, J. and Browse, J. (1993). Cloning of higher plant w-3 fatty acid desaturases. *Plant Physiol.* 103: 467–476.
151. Yoder, D. W., Nampaisansuk, M., Pirtle, I. L., Chapman, K. D. and Pirtle, R. M. (1999). Molecular cloning and nucleotide sequence of a gene encoding a cotton palmitoyl-acyl carrier protein thioesterase, *Biochimica et Biophysica Acta* 1446: 403–413.

We claim:

1. A process for producing a cotton plant wherein the fatty acid of the seed oil of the plant comprises 58.5% oleic acid, the process comprising the step of introducing into a cotton plant a gene construct encoding a ribonucleotide molecule which reduces expression of the endogenous cotton ghFAD2-1 gene in the seed of the cotton plant, thereby producing the cotton plant.

2. The process of claim 1, wherein the fatty acid of the seed oil comprises 66% oleic acid.

3. The process of claim 2, wherein the fatty acid of the seed oil comprises 68.9% oleic acid.

4. The process of claim 1, wherein the seed oil has a decreased palmitic acid content relative to the seed oil from an isogenic non-transformed plant.

5. The process of claim 1, wherein the ribonucleotide molecule comprises nucleotides encoded by a sequence, in the sense or antisense orientation, selected from the group consisting of:
   (A) the nucleotide sequence set forth in SEQ ID NO: 3 or SEQ ID NO: 7; and
   (B) a nucleotide sequence which encodes the amino acid sequence set forth in SEQ ID NO: 4.

6. The process of claim 1, wherein the ribonucleotide molecule comprises an inverted repeat comprising nucleotides having a sequence corresponding to a sequence of nucleotides of the endogenous cotton ghFAD2-1 gene transcript linked to nucleotides having a sequence which is complementary to the sequence of nucleotides.

7. The process according to claim 6, wherein the sequence nucleotides is from the 5'-untranslated region of SEQ ID NO: 3.

8. The process of claim 6, wherein the sequence of nucleotides is from the 5'-untranslated region of the ghFAD2-1 gene set forth in SEQ ID NO: 7.

9. The process of claim 1, wherein the gene construct comprises a promoter selected from the group consisting of the soybean lectin promoter sequence and the ghFAD2-1 gene promoter.

10. A transgenic cotton plant produced by the process of claim 1 comprising a gene construct encoding a ribonucleotide molecule which reduces expression of the endogenous cotton ghFAD2-1 gene in the seed of the cotton plant.

11. A transgenic cotton plant wherein the fatty acid of the seed oil of the plant comprises 58.5% oleic acid.

12. The transgenic cotton plant of claim 11, wherein the fatty acid of the seed oil comprises 66.0% oleic acid.

13. The transgenic cotton plant of claim 12, wherein the fatty acid of the seed oil comprises 68.9% oleic acid.

14. The transgenic cotton plant of claim 11, wherein the seed oil has a decreased palmitic acid content relative to the seed oil from an isogenic non-transformed plant.

15. A transgenic cotton seed of the plant of claim 10.

16. A transgenic cotton seed of the plant of claim 11.

17. A transgenic cotton seed of the plant of claim 12.

18. A transgenic cotton seed of the plant of claim 14.

19. A process for producing cotton seed oil wherein the fatty acid of the oil comprises 58.5% oleic acid, the process comprising the steps of:
   (A) obtaining a transgenic cotton plant comprising a gene construct encoding a ribonucleotide molecule which reduces expression of the endogenous cotton ghFAD2-1 gene in the seed of the cotton plant; and
   (B) growing the transgenic cotton plant for a time and under conditions sufficient for the production of cotton seed by the cotton plant, wherein the fatty acid of the oil of the cotton seed comprises 58.5% oleic acid; and
   (C) extracting the oil from the cotton seed, thereby producing the cotton seed oil.

20. The process of claim 19, wherein the fatty acid of the cotton seed oil comprises 66% oleic acid.

21. The process of claim 20, wherein the fatty acid of the cotton seed oil comprises 68.9% oleic acid.

22. The process of claim 19, wherein the cotton seed oil has a decreased palmitic acid content relative to seed oil from an isogenic non-transformed plant.

23. The process of claim 19, wherein the ribonucleotide molecule comprises nucleotides, encoded by a sequence, in the sense or antisense orientation, selected from the group consisting of:
   (A) the nucleotide sequence set forth in SEQ ID NO: 3 or SEQ ID NO: 7; and
   (B) a nucleotide sequence which encodes the amino acid sequence set forth in SEQ ID NO: 4.

24. The process of claim 19, wherein the ribonucleotide molecule comprises an inverted repeat comprising nucleotides having a sequence corresponding to at a sequence of nucleotides of the endogenous cotton ghFAD2-1 gene transcript linked to nucleotides having a sequence which is complementary to the sequence of nucleotides.

25. The process according to claim 24, wherein the sequence of nucleotides is from the 5'-untranslated region of SEQ ID NO: 3.

26. The process of claim 24, wherein the sequence of nucleotides is from the 5'-untranslated region of the ghFAD2-1 gene set forth in SEQ ID NO: 7.

27. The process of claim 19, wherein the gene construct comprises a promoter selected from the group consisting of the soybean lectin promoter sequence and the ghFAD2-1 gene promoter.

28. A gene construct for increasing the oleic acid content of cottonseed oil, comprising nucleotides having a sequence encoding a ribonucleotide molecule which reduces expression of the endogenous cotton ghFAD2-1 gene in the seed of the cotton plant, wherein the sequence is selected from the group consisting of:
   A) an inverted repeat sequence comprising a sequence of nucleotides from the 5'-untranslated region of SEQ ID NO: 3 linked to a nucleotide sequence which is complementary to the sequence of nucleotides; and
   (B) an inverted repeat sequence comprising a sequence of nucleotides from the 5'-untranslated region of the ghFAD2-1 gene set forth in SEQ ID NO: 7 linked to a nucleotide sequence which is complementary to the sequence of nucleotides.

29. The gene construct of claim 28, comprising a promoter sequence selected from the group consisting of a soybean lectin gene promoter sequence and the ghFAD2-1 gene promoter.

30. The gene construct of claim 28, wherein the inverted repeat sequence comprises an intervening sequence between the sequence of nucleotides and the sequence complementary thereto.

* * * * *